(12) United States Patent
Mentzel et al.

(10) Patent No.: US 7,241,770 B2
(45) Date of Patent: Jul. 10, 2007

(54) HYDRONOPOL DERIVATIVES AS AGONISTS ON HUMAN ORL1 RECEPTORS

(75) Inventors: Matthias Mentzel, Hannover (DE); Dania B. Reiche, Hannover (DE); Reinhard Brückner, Hannover (DE); Samuel David, Hannover (DE); Bartholomeus J. Van Steen, Hannover (DE); Uwe Schön, Hannover (DE); Daniel Jasserand, Hannover (DE); Ulf Preuschoff, Hannover (DE)

(73) Assignee: Solvay Pharmaceuticals GmbH, Hanover (DE)

( * ) Notice: Subject to any disclaimer, the term of this patent is extended or adjusted under 35 U.S.C. 154(b) by 156 days.

(21) Appl. No.: 11/007,255

(22) Filed: Dec. 9, 2004

(65) Prior Publication Data

US 2005/0131004 A1 Jun. 16, 2005

Related U.S. Application Data

(60) Provisional application No. 60/528,701, filed on Dec. 12, 2003.

(51) Int. Cl.
*A61K 31/438* (2006.01)
*C07D 471/10* (2006.01)

(52) U.S. Cl. ........................................ 514/278; 546/20
(58) Field of Classification Search ................ 514/278; 546/20
See application file for complete search history.

(56) References Cited

U.S. PATENT DOCUMENTS

2001/0041711 A1 11/2001 Kyle et al.
2003/0109539 A1 6/2003 Jordan et al.

FOREIGN PATENT DOCUMENTS

| EP | 0 997 464 A1 | 5/2000 |
|---|---|---|
| JP | 2000169476 | 6/2000 |
| WO | WO 01/07050 A1 | 2/2001 |
| WO | WO 2004/022558 A2 | 3/2004 |

OTHER PUBLICATIONS

Bundgaard, "Novel Chemical Approaches in Prodrug Design," *Drugs of the Future* 16(5): 443-458 (1991).

*Primary Examiner*—Charanjit S. Aulakh
(74) *Attorney, Agent, or Firm*—Finnegan, Henderson, Farabow, Garrett & Dunner, L.L.P.

(57) ABSTRACT

The invention relates to a group of hydronopol derivatives which are agonists on human ORL1 (nociceptin) receptors. The invention also relates to the preparation of these compounds, to pharmaceutical compositions containing a pharmacologically active amount of at least one of these novel hydronopol derivatives as an active ingredient, as well as to the use of these pharmaceutical compositions for the treatment of disorders in which ORL1 receptors are involved.

The invention relates to compounds of the general formula (1)

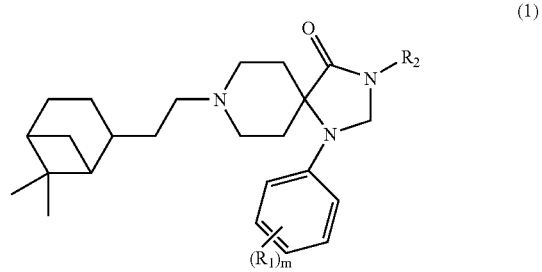

wherein the symbols have the meanings as given in the description.

7 Claims, No Drawings

HYDRONOPOL DERIVATIVES AS AGONISTS ON HUMAN ORL1 RECEPTORS

CROSS REFERENCE TO RELATED APPLICATIONS

This application claims the priority of European Patent Application No. 03104662.6, filed on Dec. 12, 2003, and the benefit of U.S. Provisional Application No. 60/528,701, filed on Dec. 12, 2003, the contents of all of which are incorporated herein by reference.

The present invention relates to a group of hydronopol derivatives which are agonists on human ORL1 (nociceptin) receptors. The invention also relates to the preparation of these compounds, to pharmaceutical compositions containing a pharmacologically active amount of at least one of these novel hydronopol derivatives as an active ingredient, as well as to the use of these pharmaceutical compositions for the treatment of disorders in which ORL1 receptors are involved.

The 'Opioid Receptor-Like 1' (ORL1) receptor was identified from a human cDNA library. It was established that this 'orphan receptor' has a close homology with μ-, κ- and δ-opioid receptors (Mollereau et al., *FEBS Lett.*, 341, 33-38, 1994; Bunzow et al., *FEBS Lett.*, 347, 284-288, 1994). Despite its close sequential and structural resemblance with opioid receptors, classical opioid receptor ligands do not interact with ORL1 receptors. In 1995 a 17-amino acid neuropeptide was purified from brain extracts, and subsequently shown to be the natural ligand of the G protein-coupled ORL1 receptor (Reinscheid et al., *Science*, 270, 792-794, 1995; Meunier et al., *Nature*, 377, 532-535, 1995). This peptide was named orphanin FQ or nociceptin and it does not bind to the three traditional opioid receptors. These findings triggered substantial research into the functional role of, and novel ligands for, the ORL1 receptor. That resulted in several hundreds of publications, including several reviews (see e.g. Grond et al., *Anaesthesist*, 51, 996-1005, 2002), and dozens of patent applications, describing both peptide and non-peptide ligands, varying in potency and selectivity (ORL-1 versus μ-opiate). As μ-opiate receptors are widely distributed throughout the body, a lack of selectivity might lead to a range of undesired opiate-like side-effects e.g. sedation, respiratory depression, constipation, tolerance and dependence (*Drug News Perspect*, 14, 335, 2001).

1,3,8-triazaspiro[4,5]decan-4-one derivatives are described in JP-A-2000/169476, published on Jun. 20, 2000; in WO 01/07050 A1, published on Feb. 1, 2001 and in US 2003/0109539 A1, published on Jun. 12, 2003. However, in none of the applications cited above μ-opiate receptors are mentioned. In EP 0 997 464 A1, published on May 3, 2000, 1,3,8-triazaspiro[4,5]decanone compounds as ORL-1 receptor agonists are said to possess selective affinity for ORL1-receptors, but actual information on μ-opiate receptor affinity was limited to the statement that: "particularly preferred compounds demonstrated higher affinity for ORL-1 receptors than for mu-receptors (i.e. $IC_{50}$ for ORL1-receptors/$IC_{50}$ for mu-receptors were less than 1.0". More specific is US 2001/0041711, published on Nov. 15, 2001. This patent application describes triazospiro compounds having nociceptin receptor affinity. The compounds were also tested on μ-, κ-, and δ-opiate receptors but with a few exceptions only, found to be more potent on μ-opiate receptors than on ORL-1 receptors. The exceptions were ORL-1 selective by less than a factor 2. Thus the closest prior art does not teach how to design potent ORL-1 ligands with an unambiguous selectivity over μ-opiate receptors, that is a selectivity of at least a factor 10, let alone such compounds which also have a good bioavailability. Finally, hydroxy alkyl substituted 1,3,8-triazaspiro[4,5]decan-4-one derivatives useful for the treatment of ORL-1 receptor mediated disorders were published on Mar. 18, 2004 in WO 2004/022558, filed on Sep. 5, 2003.

Surprisingly, it has now been found that in a series of hydronopol derivatives, a group of compounds was shown to have a very high affinity for human ORL1 receptors. Moreover, these compounds show a good selectivity for ORL1 receptors relative to μ-opiate receptors, and are readily available after oral administration.

The invention relates to compounds of the general formula (1)

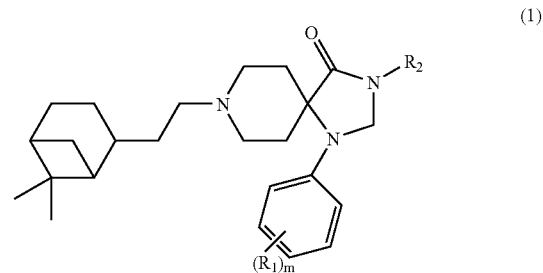

(1)

wherein:

$R_1$ represents hydrogen, halogen, $CF_3$, alkyl(1-6C), cycloalkyl(3-6C), phenyl, amino alkyl(1-3C)amino, dialkyl(1-3C)amino, hydroxy, hydroxyalkyl(1-3C), (1-3C)alkoxy, $OCF_3$, carboxyl, aminocarbonyl or (1-3C)alkylsulphonyl, m is an integer from 1-4, with the proviso that when m is 2, 3 or 4, the $R_1$ substituents may be either the same or different, $R_2$ represents hydrogen, optionally substituted alkyl(1-6C), cycloalkyl(3-6C), $—CH_2OH$, $—CH_2OCH_3$, carboxyl, acetyl, optionally substituted benzyl or a group Q of the following structure (2):

(2)

wherein:

$[\ ]_n$ symbolizes $—(CH_2)_n—$ wherein n is an integer from 0-7;

$R_3$ represents hydrogen or alkyl(1-3C), $R_4$ represents hydrogen, optionally substituted alkyl(1-6C), a saturated, unsaturated or partially saturated mono-, di- or tricyclic optionally substituted ring, or an alkyl(1-3C) group substituted with a saturated, unsaturated or partially saturated optionally substituted five or six-membered ring which optionally contains one or more heteroatoms, or $(R_3+R_4)$ together with the nitrogen atom to which they are bonded, represent a saturated, unsaturated or partially saturated mono-, di- or tricyclic optionally substituted ring, and pharmacologically acceptable salts and prodrugs thereof.

In the description of the substituents the abbreviation '$C_{1-3}$-alkyl' means 'methyl, ethyl, n-propyl or isopropyl'. 'Optionally substituted' means that a group may or may not be further substituted by one or more groups selected from alkyl, alkenyl, alkynyl, aryl, fluoro, chloro, bromo, hydroxyl, alkyloxy, alkenyloxy, aryloxy, acyloxy, amino, alkylamino, dialkylamino, arylamino, thio, alkylthio, arylthio, cyano, oxo, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulphur. Within the context of the explanation of 'optionally substituted', 'alkyl' means $C_{1-3}$-alkyl, 'alkenyl' means $C_{1-3}$-alkenyl, 'alkynyl' means $C_{1-3}$-alkynyl, 'acyl' means $C_{1-3}$-acyl and 'aryl' means furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 1,3,5-triazynyl, phenyl, indazolyi, indolyl, indolizinyl, isoindolyl, benzi[b]furanyl, benzo[b]thiophenyl, benz-imidazolyl, benzthiazolyl, purinyl, quinolynyl, isochinolyl, chinolyl, phtalazinyl, quinazolinyl, quinoxalinyl, 1,8-naphthyridinyl, pteridinyl, naphthyl or azulenyl, preferably phenyl, pyridyl or naphthyl. Optional substituents may themselves bear additional optional substituents. Preferred optional substituents include $C_{1-3}$ alkyl such as for example methyl, ethyl, and trifluoromethyl, fluoro, chloro, bromo, hydroxyl, $C_{1-3}$ alkyloxy such as for example methoxy, ethoxy and trifluoromethoxy, and amino. 'Heteroatom' means an atom such as N, O or S. 'Five- or six-membered rings' are for example: furan, thiophene, pyrrole, oxazole, thiazole, imidazole, pyrazole, isoxazole, isothiazole, 1,2,3-oxadiazole, 1,2,3-triazole, 1,3,4-thiadiazole, pyridine, pyridazine, pyrimidine or pyrazine rings.

To the invention belong all compounds having formula (1), racemates, mixtures of diastereomers and the individual stereoisomers. Thus compounds in which the substituents on potentially asymmetrical carbon atoms are in either the R-configuration or the S-configuration belong to the invention.

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", Expert Opin. Ther. Patents, 14(3), 277-280, 2004; P. Ettrmayer et al., "Lessons learned from marketed and investigational pro-drugs", J. Med. Chem., 47, 2393-2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

The invention particularly relates to compounds having formula (1) wherein: $R_1$ represents hydrogen, halogen, $CF_3$, alkyl(1-6C), hydroxy, (1-3C)alkoxy or $OCF_3$, m=1, and all other symbols have the meanings as given above.

More particular, the invention relates to compounds having formula (1) wherein: $R_1$ represents hydrogen, halogen, $CF_3$, alkyl(1-6C), hydroxy, (1-3C)alkoxy or $OCF_3$, m=1, $R_2$ represents a group Q having general formula (2), and all other symbols have the meanings as given above.

Even more particular, the invention relates to compounds having formula (1) wherein: $R_1$ represents hydrogen, halogen, $CF_3$, alkyl(1-6C), hydroxy, (1-3C)alkoxy or $OCF_3$, m=1, $R_2$ represents a group Q having general formula (2), $R_3$ represents a methyl group, $R_4$ represents an alkyl(1-3C) group substituted with a saturated, optionally substituted six-membered ring which optionally contains one or more heteroatoms, and $[\ ]_n$ has the meanings as given above.

The most preferred compounds of the invention are those having formula (1) wherein: $R_1$ represents hydrogen, halogen, $CF_3$, alkyl(1-6C), hydroxy, (1-3C)alkoxy or $OCF_3$, m=1, $R_2$ represents a group Q having general formula (2), $R_3$ represents a methyl group, $R_4$ represents a methylene group substituted with an optionally substituted piperidine ring, and $[\ ]_n$ has the meanings as given above.

Pharmaceutically acceptable salts may be obtained using standard procedures well known in the art, for example by mixing a compound of the present invention with a suitable acid, for instance an inorganic acid such as hydrochloric acid, or with an organic acid.

The compounds of the invention of the general formula (1), as well as the salts thereof, have ORL1 agonistic activity. They are useful in the treatment of disorders in which ORL1 receptors are involved, or which can be treated via manipulation of those receptors especially, but not limited to, acute and chronic pain conditions, metabolic disorders like anorexia nervosa and bulimia nervosa, obesity; gastro-intestinal disorders in particular irritable bowel syndrome, inflammatory bowel disease (Crohn's disease and ulcerative colitis), diarrhoea, constipation, visceral pain, urinary tract inflammation, renal disorders characterized by imbalances of water retention/excretion or salt excretion; cardiovascular disorders such as myocardial infarction, arrhythmias, hypertension, thrombosis, anaemia, arteriosclerosis, angina pectoris, opthalmological disorders like glaucoma; respiratory disorders including chronic obstructive pulmonary disease, bronchitis and cystic fibrosis; diseases of the immune system, and viral infections.

The in vitro and in vivo ORL1 receptor agonistic properties of the compounds of the invention were determined using the methods outlined below.

Affinity for Human ORL1 Receptors

Affinity of the compounds for human ORL1 receptors was determined using the in vitro receptor binding assay described by Ardati et al., Mol. Pharmacol., 51, 816, 1997. Briefly, membrane preparations were obtained from CHO (Chinese Hamster Ovary)-cells in which the human ORL1 receptor was stably expressed. Membranes were incubated with [$^3$H]-nociceptin in the absence or presence of test-compounds in different concentrations, diluted in a suitable buffer. Non specific binding was defined as binding remaining in the presence of $10^{-6}$ M nociceptin. Separation of bound radioactivity from free was done by filtration through Packard GF/B glass fiber filters with several washings with ice-cold buffer using a Packard cell harvester. Bound radioactivity was measured with a scintillation counter (Top-count, Packard) using a liquid scintillation cocktail (Microscint 0, Packard). Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_1$ values were calculated by correcting the $IC_{50}$ values for radioligand concentration and its affinity for the human ORL1 receptor according to the Cheng-Prusoff equation:

$$pK_1 = -\log(IC_{50}/(1+S/K_d))$$

in which the $IC_{50}$ is as described above, S is the concentration [$^3$H]-nociceptin used in the assay expressed in mol/l (typically 0.2 nM), and $K_d$ is the equilibrium dissociation constant of [$^3$H]-nociceptin for human ORL1 receptors (0.4 nM).

The compounds of the invention have a high affinity for ORL1 receptors in the binding assay described above. This property makes them useful in the treatment of disorders in which ORL1 receptors are involved, or that can be treated via manipulation of these receptors.

Affinity for μ-Opiate Receptors

Affinity of the compounds for μ-opiate receptors was determined using the in vitro receptor binding assay described by Wang et al., *FEBS Letters*, 338, 217, 1994. Briefly, membrane preparations were obtained from CHO-cells in which the human μ-opiate receptor was stably expressed, and were incubated with the μ-opiate specific ligand [$^3$H]-DAMGO (D-Ala$^2$, N-Me-Phe$^4$, glycinol$^5$-Enkephalin) in the absence or presence of test-compounds in different concentrations, diluted in a suitable buffer. Non specific binding was defined as binding remaining in the presence of $10^{-6}$ M naloxone. Separation of bound radioactivity from free was done as described above, and the affinity of the compounds was calculated in a similar way.

The compounds of the invention have a low affinity for μ-opiate receptors in the binding assay described above. Thus they are unlikely to evoke the unwanted side effects known to occur with opiates like morphine.

In vitro ORL1 Receptor Agonism

Activation of the G protein-coupled ORL1 receptor inhibits adenylate cyclase activity and reduces the intracellular concentration of the second messenger cAMP. Using an assay as described by Jenck et al., *Proc. Natl. Acad. Sci USA*, 97, 4938-4943, 2000, the activity of the compounds on ORL1 receptors was measured. They were demonstrated to be potent agonists with $pEC_{50}$-values matching their $pK_1$ values.

Castor Oil Induced Diarrhoea in Conscious Mice

The compounds of the invention were shown to be able to reduce the castor oil induced diarrhea in mice, as was the peptide nociceptin after subcutaneous administration. Since a peripherally administered peptide does not penetrate the blood brain barrier, it is indicated that the ORL1 mediated reduction in diarrhea is peripherally mediated.

Animals used: male NMRI mice were used for this model in the model of castor oil-induced diarrhoea. In all experiments, a group consisted of 10 to 12 animals.

Experimental procedures: on the day of the experiment, the mice received either compound or vehicle (bi-weekly intervals). Castor oil (8 ml/kg body weight) was administered orally 30 min later and the animals were placed individually in cages with free access to water. The feces were collected after a period of 5 h. During this time the quality of the feces was determined every 20 min by visual inspection. This diarrhoea score ranged from 0=no output, 1=normal output, 2=slight diarrhoea, 3=moderate diarrhoea to 4=severe diarrhoea. Thus, this score reflects the onset and intensity of diarrhoea. In these experiments the mean diarrhoea score and the dry weight of the feces were determined.

Data analysis: the effects of the compounds are given as relative numbers (percent of control values). The original data registered in the experiments were compared to controls (without compound) in the same animals by paired two sided t-tests or to a control group by a non paired t-test. Values of p<0.05 were taken as statistically significant.

Colon Transit in Conscious Rats

The compounds of the invention were shown to not influence the normal colon transit in rats. This was also the case for the peptide Nociceptin after subcutaneous administration. Since a peripherally administered peptide does not penetrate the blood brain barrier, it is indicated that peripheral ORL1 receptor activation does not impair the normal gastrointestinal transit. In contrast peripheral μ-opiate receptor activation is able to strongly impair the transit in this model. Thus, this test shows the selectivity of the compounds of the invention for the ORL1 receptor.

Animals used: for the experiments male Sprague Dawley rats were used. In all experiments, a group consisted of 10 to 12 animals.

Experimental procedures: prior to the experiments the rats were equipped with a chronic titanium cecal fistula under general anesthesia. The animals were allowed to recover from surgery and were trained to a feeding regimen of free access to the chow during 3 h per day. On the day of the experiments after the feeding period, a marker substance (2 ml of a suspension containing 80% barium sulfate) was injected via the fistula into the caecum and the animals received either compound or vehicle. Subsequently they were placed in metabolic cages and fecal pellets were collected at hourly intervals for a 21 h period using an automated collection system. During this time the animals had free access to water. The barium sulfate content in the feces was analyzed radiographically and the feces were weighed. The function of the marker content in feces versus time and amount of feces enabled the analysis of the mean retention time of barium sulfate, i.e. the colon transit time. The mean retention time of the $BaSO_4$ containing pellets and the total fecal output were determined.

Data analysis: the effects of the compounds are given as relative numbers (percent of control values). The original data registered in the experiments were compared to controls (without compound) in the same animals by paired two sided t-tests. Values of p<0.05 were taken as statistically significant. In the colon transit model, the control data represent the mean of two control experiments (before and after compound, weekly intervals).

Acetic Acid Induced Visceral Hypersensitivity in Conscious Rats

The compounds of the invention were shown to be able to reduce the visceral hypersensitivity in rats, as was the peptide Nociceptin after subcutaneous administration. Since a peripherally administered peptide does not penetrate the blood brain barrier, it is indicated that the ORL1 mediated reduction in visceral hypersensitivity is peripherally mediated.

Animals used: adult female Sprague Dawley rats, body weight: in the range of 200-250 g. A group consists of 5 to 10 animals.

Experimental Procedure: animals were fasted for 24 hours prior to the experiments with free access to water. Acetic acid (0.6%, 1.5 ml) was injected into the colon (10 cm proximal to the anus). After 50 minutes a rubber balloon of 5 cm length (6-7 ml volume) was inserted rectally into the distal colon and secured by taping the attached tubing to the rat's tail. Colorectal distension was performed by setting the balloon pressure to 100 mbar for 10 minutes. During this time the number of abdominal constrictions were monitored by visual inspection. The experiments were continued only in animals which responded to the chlorectal distension with more than 10 abdominal constrictions. These animals received a single dose of substance or vehicle and colorectal distension protocol was repeated at 30, 60, 90 and 120 minutes after administration.

Data analysis: results are given as mean±SD. The number of abdominal constrictions at 30, 60, 90 and 120 minutes after administration of substance or vehicle as well as the mean values (30-120 min) was compared to prevalues by paired two sided t-tests. Relative numbers of abdominal constrictions (% of prevalues) at 30, 60, 90 and 120 minutes and the relative mean values (30-120 min) were compared between substance and vehicle by unpaired two sided t-tests. Values of $p<0.05$ were taken as statistically significant.

In vivo ORL1 Receptor Agonism: Lack of CNS-penetration

Most of the compounds of the invention were shown to be devoid of activity in the Adult stress-induced ultrasonic vocalisation (AUV) procedure as described by Van der Poel et al., *Psychopharmacology*, 97, 147-148, 1989. This demonstrates that the compounds do not penetrate the blood-brain-barrier. The peptide nociceptin is also active in this assay, but in order to demonstrate its effect, it needs to be administered directly into the brain (by intracerebroventricular injection).

EXAMPLES OF SYNTHESES OF
INTERMEDIATES AND END PRODUCTS (−)-trans-2-(6,6-Dimethyl-bicyclo[3.1.1]hept-2-yl)-ethanol (5)

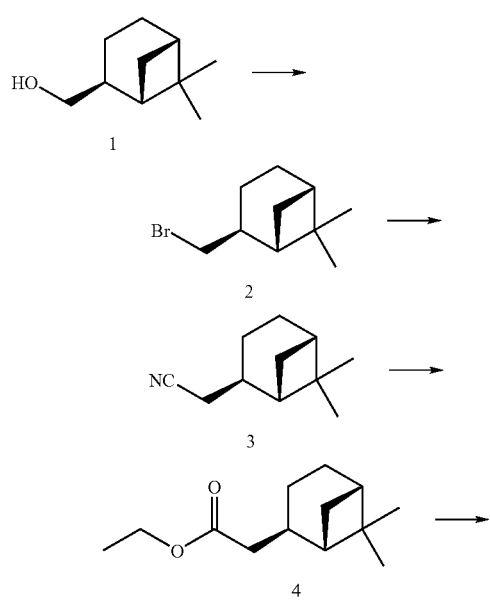

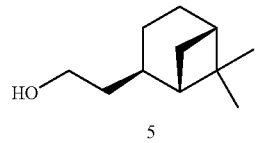

Myrtanyl Bromide (2)

Triphenyl phosphine (116 g, 0.44 mol) was dissolved in acetonitrile (1 l) and cooled in an ice bath under $N_2$ atmosphere. Bromine (22.5 ml, 0.44 mol) was added drop wise. The temperature of the exothermic reaction was maintained below 10° C. After complete addition the ice bath was removed and (−)-trans-myrtanol (1) (2,686 g, 0.44 mol) dissolved in acetonitrile (250 ml) was added slowly. After complete addition the light yellow solution was refluxed for 3 h using a Dean-Stark equipment. During the reaction, the solvent in the water trap was removed 20 times (ca. 200 ml of solvents in total). GC analysis revealed complete conversion of the starting material. The mixture was evaporated to dryness. The crude mixture was purified over silica column. (eluent: dichloromethane/diethyl ether 1/1, v/v). This resulted in 87.8 g of bromide 3 (91%) as light yellow oil.

Myrtanyl Cyanide (3)

Myrtanyl bromide (2) (87.8 g, 0.41 mol) was dissolved in dimethylformamide (1 l). Sodium cyanide (40 g, 0.81 mol) was added and the mixture was stirred at reflux for 5 h. GC analysis revealed complete conversion. The mixture was diluted with water (3 l) and extracted with tert.-butyl methyl ether (TBME, 3×1.5 l). The organic layer was washed with brine, dried over $Na_2SO_4$ and concentrated to dryness. The crude mixture was purified over silica column (eluent: heptane/dichloromethane, 1/1, v/v) to give 52.4 g (80%) of cyanide (3) as colorless liquid.

Ethyl Ester (4)

Ethanol (500 ml) was cooled in an ice bath. Sulfuric acid (190 ml) was added drop wise. Cyanide (3) (52.4 g, 0.32 mol) dissolved in ethanol (100 ml) was added and the mixture was stirred at reflux overnight. GC analysis revealed complete addition. The mixture was cooled and water (1.5 l) was added. The mixture was extracted with TBME (3×1.5 l). The organic layer was washed with $NaHCO_3$ (sat. 1 l), dried over $Na_2SO_4$ and concentrated. Yield: 54.2 g of ester 5 (80%) as near colorless liquid. Crude (4) was used in the next reaction without purification.

(−)-trans-2-(6,6-Dimethyl-bicyclo[3.1.1]hept-2-yl)-ethanol (5)

To a suspension of lithium aluminum hydride (20 g, 0.52 mol) in tetrahydrofuran (1 l) was added ester (4) (54.2 g, 0.26 mol) dissolved in tetrahydrofuran (500 ml). After complete addition the mixture was refluxed for 1 h. GC analysis revealed complete conversion of starting material. The mixture was cooled in an ice bath and HCl (1M, 1 l) was added carefully. After complete addition, the mixture was diluted with water (1 l) and extracted with TBME (3×1.5 l). The organic layer was washed with brine, dried over $Na_2SO_4$ and concentrated to dryness. The crude mixture was purified by Kugelrohr distillation (b.p. 85° C., 3.10$^{-2}$ mbar). Yield: 35.9 g of compound 1 (65%) as colorless oil.

(+)-trans-2-(6,6-Dimethyl-bicyclo[3.1.1]hept-2-yl)-ethanol (10)

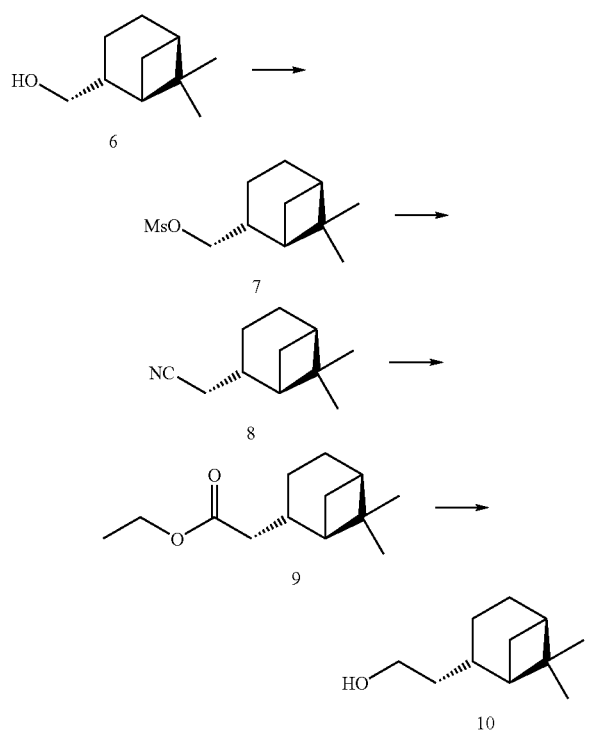

Myrtanyl Mesylate (7)

18.1 g (0.12 mol) of (+)-trans-myrtanol (6) was added to a solution of 18.5 ml mesyl chloride (2 eq., 0.24 mol, 27.5 g) and 49 ml pyridine (5 eq., 0.60 mol, 47.5 g) in 400 ml DCM. The reaction mixture was stirred overnight at room temperature. Water was added and the reaction mixture was stirred for 1 h. The organic layer was extracted and the water layer was extracted two more times. The combined organic layers were washed (saturated NaHCO$_3$, water, brine), dried (Na$_2$SO$_4$) and evaporated in vacuo to give 25.9 g (91%) of mesylate (7) as a colourless oil.

Myrtanyl Cyanide (8)

Myrtanyl mesylate (7) (25.9 g, 0.11 mol) was dissolved in DMSO (250 ml). Potassium cyanide (4 eq, 29.2 g, 0.45 mol) was added and the mixture was stirred at 70° C. for 2 days. GC analysis revealed complete conversion. The mixture was diluted with water (750 ml) and extracted with TBME (3×300 ml). The organic layer was washed with brine, dried over Na$_2$SO$_4$ and concentrated to dryness to give 17.7 g (quantitative yield) of cyanide (8) as a colourless oil.

Ethyl Ester (9)

Ethanol (200 ml) was cooled in an ice bath. Sulphuric acid (80 ml) was added dropwise. Cyanide (8) (17.7 g, 0.11 mol) dissolved in ethanol (40 ml) was added and the mixture was stirred at reflux overnight. GC analysis revealed complete addition. The mixture was cooled and water (1 l) was added. The mixture was extracted with TBME (3×500 ml). The organic layer was washed with NaHCO$_3$ (sat., 500 ml), dried over Na$_2$SO$_4$ and concentrated. Yield: 20.4 g of ester (9) (88%) as a yellow oil. Crude (9) was used in the next reaction without purification.

(+)-trans-Dihydronopol (10)

To a suspension of lithium aluminium hydride (7.4 g, 0.19 mol) in tetrahydrofuran (350 ml) was added ester (9) (20.1 g, 0.09 mol) dissolved in tetrahydrofuran (200 ml). After complete addition the mixture was refluxed for 2 h. The mixture was cooled in an ice bath and HCl (1M, 1 l) was added carefully. After complete addition, the mixture was diluted with water (300 ml) and extracted with TBME (3×500 ml). The organic layer was washed with brine, dried over Na$_2$SO$_4$ and concentrated to dryness. The crude mixture was purified by Kugelrohr distillation (b.p. 85° C., 8.10$^{-2}$ mbar). Yield: 9.2 g of compound (10) (61%) as colourless oil.

(−)-cis-2-(6,6-Dimethyl-bicyclo[3.1.1]hept-2-yl)-ethanol (11)

The synthesis of the cis analog with (−)-β-pinene as starting material is described in *J. Amer. Chem. Soc.* 68, 638, 1946 and U.S. Pat. Nos. 2,427,343, 2,427,344 and 2,427,345.

(+)-cis-2-(6,6-dimethyl-bicyclo[3.1.1)hept-2-yl)-ethanol (18)

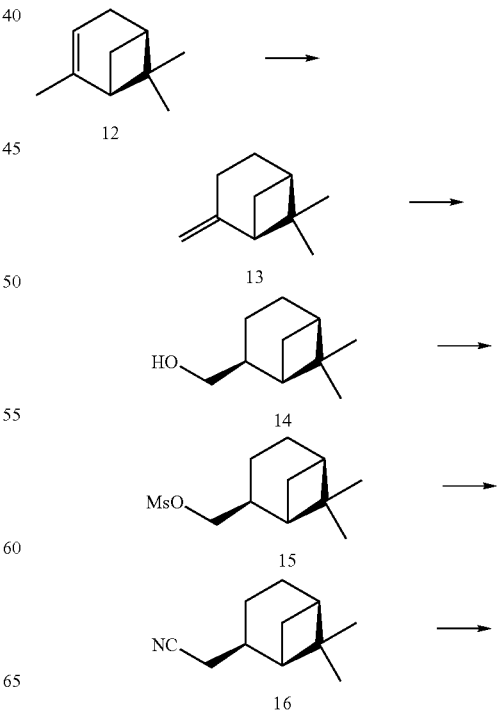

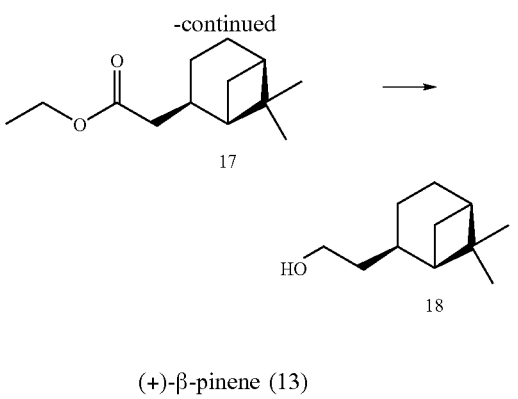

(+)-β-pinene (13)

In dried glassware, potassium t-butyl oxide (KOt-Bu, 49.4 g; 0.44 mol) was added to n-BuLi (176 ml; 2.5 M in hexane). The suspension was cooled to −78° C. The (+)-α-pinene (12) (50 g; 0.37 mol) was added drop wise. The reaction mixture was allowed to warm to room temperature and was stirred for 45 h. The reaction mixture was cooled to −78° C. and B(OMe)$_3$ (137 ml; 1.20 mol) was added drop wise. The reaction mixture was allowed to warm to room temperature (exothermic!). 10% HCl (aqueous, 250 ml) was added drop wise and the reaction mixture was stirred for 1 h. The layers were separated and the water layer was extracted with heptane (2×200 ml). The combined organic layers were dried over Na$_2$SO$_4$ and evaporated to dryness to give 36.7 g of yellow oil. The raw product was purified using Kugelrohr distillation (8-12 mbar; 50-60° C.) to give 36.6 g (0.27 mol, yield=73%, 88% pure) of (+)-β-pinene (13) as a colourless oil.

Myrtanol (14)

(+)-β-pinene (113) (36.6 g; 0.27 mol) was dissolved in THF (100 ml) and cooled down to 0° C. BH$_3$.DMS in THF (2 M; 47.3 ml) was added drop wise. The reaction mixture was stirred for 0.5 h. Ethanol (90 ml) was added. 1 M NaOH (aq) (95 ml) was added. The reaction mixture was cooled to 0° C. 33 ml 30% H$_2$O$_2$ was added drop wise while the temperature was not allowed to rise above 35° C. The reaction mixture was refluxed for 1 h and poured into water (1 l). The solution was extracted with TBME. The combined organic layers were washed with water and brine, dried over Na$_2$SO$_4$ and evaporated to dryness. Remaining α-pinene was distilled off using Kugelrohr distillation (8-12 mbar; 50-60° C.), giving 38.6 g (0.25 mol, yield=93%) of (+)-cis-myrtanol (14) as a colourless oil.

Myrtanyl Mesylate (15)

15.0 g (0.10 mol) of (+)-cis-myrtanol (14) was added to a solution of 15 ml mesyl chloride (2 eq., 0.20 mol) and 40 ml pyridine (5 eq., 0.50 mol) in 300 ml DCM. The reaction mixture was stirred overnight at room temperature. Water was added and the reaction mixture was stirred for 1 h. The organic layer was extracted and the water layer was extracted two more times. The combined organic layers were washed (saturated NaHCO$_3$, water, brine), dried (Na$_2$SO$_4$) and evaporated in vacuo to give 21.6 g (yield=93%) of mesylate (15) as a colourless oil.

Myrtanyl Cyanide (16)

Myrtanyl mesylate (15) (21.6 g, 0.093 mol) was dissolved in DMSO (230 ml). Potassium cyanide (4 eq, 24.2 g, 0.37 mol) was added and the mixture was stirred at 70° C. for 8 days. GC analysis revealed complete conversion. The mixture was diluted with water and extracted with heptane. The organic layer was washed with brine, dried over Na$_2$SO$_4$ and concentrated to dryness to give 15.8 g (quant.) of cyanide (16) as a colourless oil.

Ethyl Ester (17)

Ethanol (150 mL) was cooled in an ice bath. Sulphuric acid (60 ml) was added drop wise. Cyanide (16) (16 g) dissolved in ethanol (30 ml) was added and the mixture was stirred at reflux overnight. GC analysis revealed complete conversion. The mixture was cooled and water (1 l) was added. The mixture was extracted with TBME (3×500 ml). The organic layer was washed with saturated NaHCO$_3$ (aqueous, 500 ml), dried over Na$_2$SO$_4$ and evaporated to dryness. Yield: 20.6 g of ester (17) (quant.) as a yellow oil. Crude (17) was used in the next reaction without purification.

(+)-cis-Dihydronopol (18)

To a suspension of lithium aluminium hydride (8.3 g, 0.22 mol) in tetrahydrofuran (400 ml) was added ester (17) (23.6 g, 0.11 mol) dissolved in tetrahydrofuran (200 ml). After complete addition the mixture was refluxed for 2 h. The mixture was cooled in an ice bath and HCl (1 M, 1 l) was added carefully. After complete addition, the mixture was diluted with water (300 ml) and extracted with TBME (3×500 ml). The organic layer was washed with brine, dried over Na$_2$SO$_4$ and concentrated to dryness, giving a yellow oil (13.4 g). The crude mixture was purified by Kugelrohr distillation (b.p. 85° C., 8×10$^{-2}$ mbar). Yield: 8.7 g (51 mmol; y=47%) of compound (18) as colourless oil.

1-Mesyl-2-(6,6-dimethyl-bicyclo[3.1.1]hept-2-yl)-ethanol (20) (for all stereo isomers of dihydronopol)

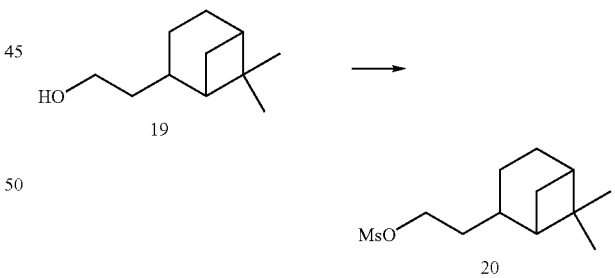

To a suspension of 67 g (0.4 mol) (−)-cis-2-(6,6-Dimethyl-bicyclo[3.1.1]hept-2-yl)-ethanol (19) in 300 ml CH$_2$Cl$_2$ at 0° C. was added 139 ml (1 mol) of triethylamine. To this mixture 55.2 g (0.48 mol) of mesyl chloride in 100 ml dichloromethane was added drop wise. After 5 h at room temperature the reaction was completed and 300 ml 1N aqueous HCl solution was added. After separation the aqueous layer was washed with dichloromethane twice and the combined organic layers were washed with water, dried over magnesium sulphate and concentrated in vacuum yielding 91.6 g (0.37 mol 91%) of a crude orange oily product. This raw material was used for the next step without further purification.

8-[2-(6,6-Dimethyl-bicyclo[3.1.1]hept-2-yl)-ethyl]-3-(3-methylamino-propyl)-1-phenyl-1,3,8-triaza-spiro[4.5]decan-4-one (24)

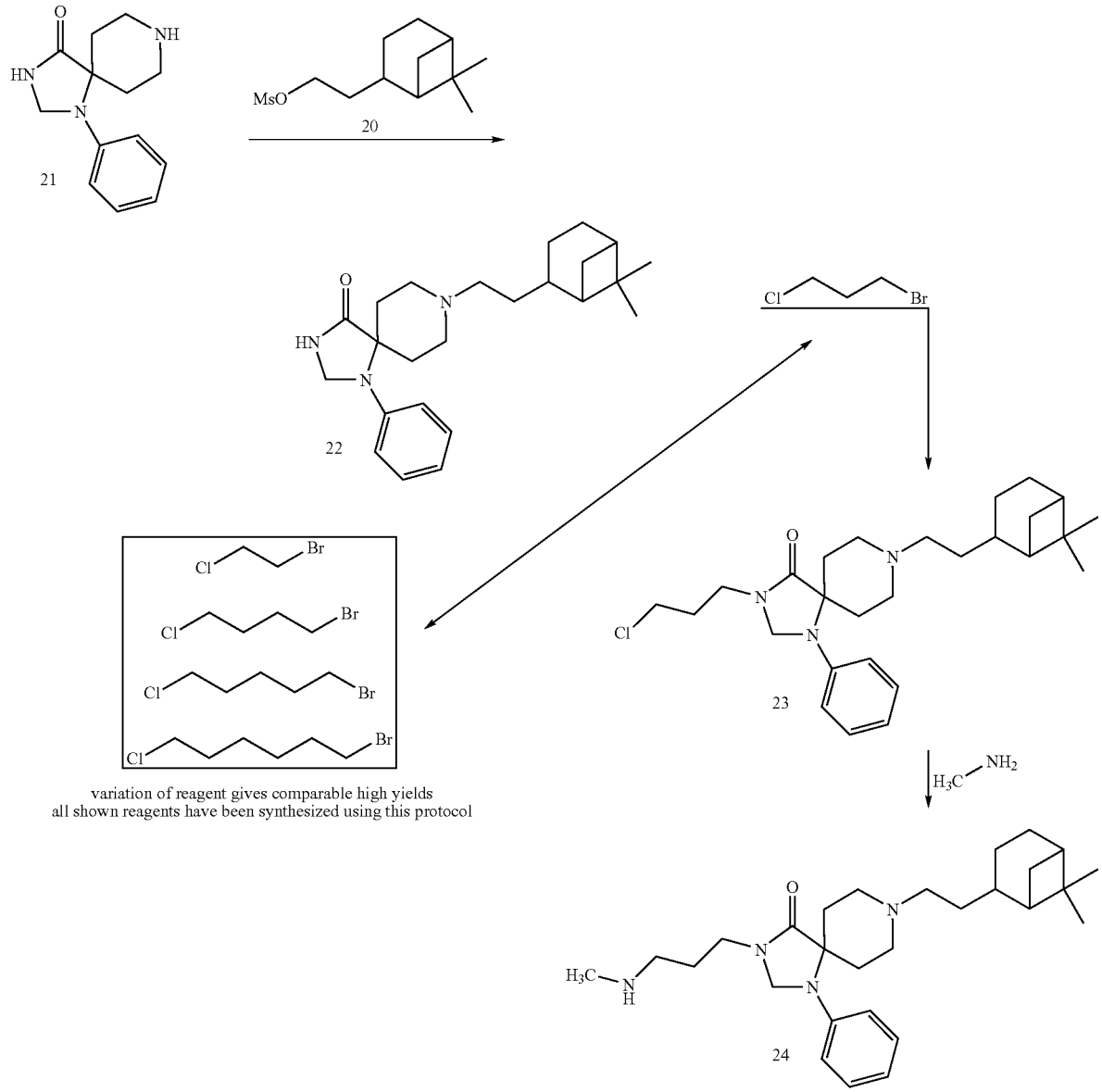

8-[2-(6,6-Dimethyl-bicyclo[3.1.1]hept-2-yl)-ethyl]-1-phenyl-1,3,8-triaza-spiro[4.5]decan-4-one (22) [example nr. 1 in tables below]

The spiro compound (21) (310 g; 1.34 mol) and (di) hydroponol mesylate (20) (371 g; 1.51 mol) were dissolved in methyl ethyl ketone (MEK, 15 l). Potassium carbonate (735 g; 5.33 mol) and sodium iodide (226 g; 1.51 mol) were added and the mixture was refluxed overnight. After cooling the reaction mixture the solvent was evaporated. The residue was taken up in $CH_2Cl_2$ (5 l) and shaken with water (4 l). The layers were separated, the organic layer dried on $Na_2SO_4$, and the solvent evaporated. The remaining solid was washed with $Et_2O$ (3 l) and filtered off. The filtrate was evaporated and washed with $Et_2O$ (300 ml). The solid was filtered off. (466.3 g; 1.22 mol; 91%).

3-(3-Chloro-propyl)-8-[2-(6,6-dimethyl-bicyclo[3.1.1]hept-2-yl)-ethyl]-1-phenyl-1,3,8-triaza-spiro[4.5]decan-4-one (23)

THF (1500 ml) was cooled in an ice/water bath. The spiro compound (22) (150.8 g; 0.40 mol) and potassium tert-butoxide (49 g; 0.44 mol) were added and the resulting mixture was stirred at 0° C. for 30 minutes. The mixture became clear. 1-bromo-3-chloropropane (43 ml; 0.44 mol) in THF (150 ml) was added drop wise to the solution at 0° C. After complete addition the cooling was removed and the solution was stirred at 50° C. for 4 hours. After cooling the mixture was poured into saturated $KHSO_4$ (aqueous, 1000 ml) and diluted with EtOAc (500 ml). The layers were separated and the aqueous layer extracted with EtOAc (3×750 ml). The combined organic layers were washed with water and brine (1×500 ml each). After drying on Na$_2$SO$_4$ the solvent was evaporated to yield a yellow oil (205.6 g; 0.45 mol; quantitative yield).

Variation of the substitution pattern of the phenyl ring in the spiro core 8-[2-(6,6-Dimethyl-bicyclo[3.1.1]hept-2-yl)-ethyl]-1-phenyl-1,3,8-triaza-spiro[4.5]decan-4-one (22)

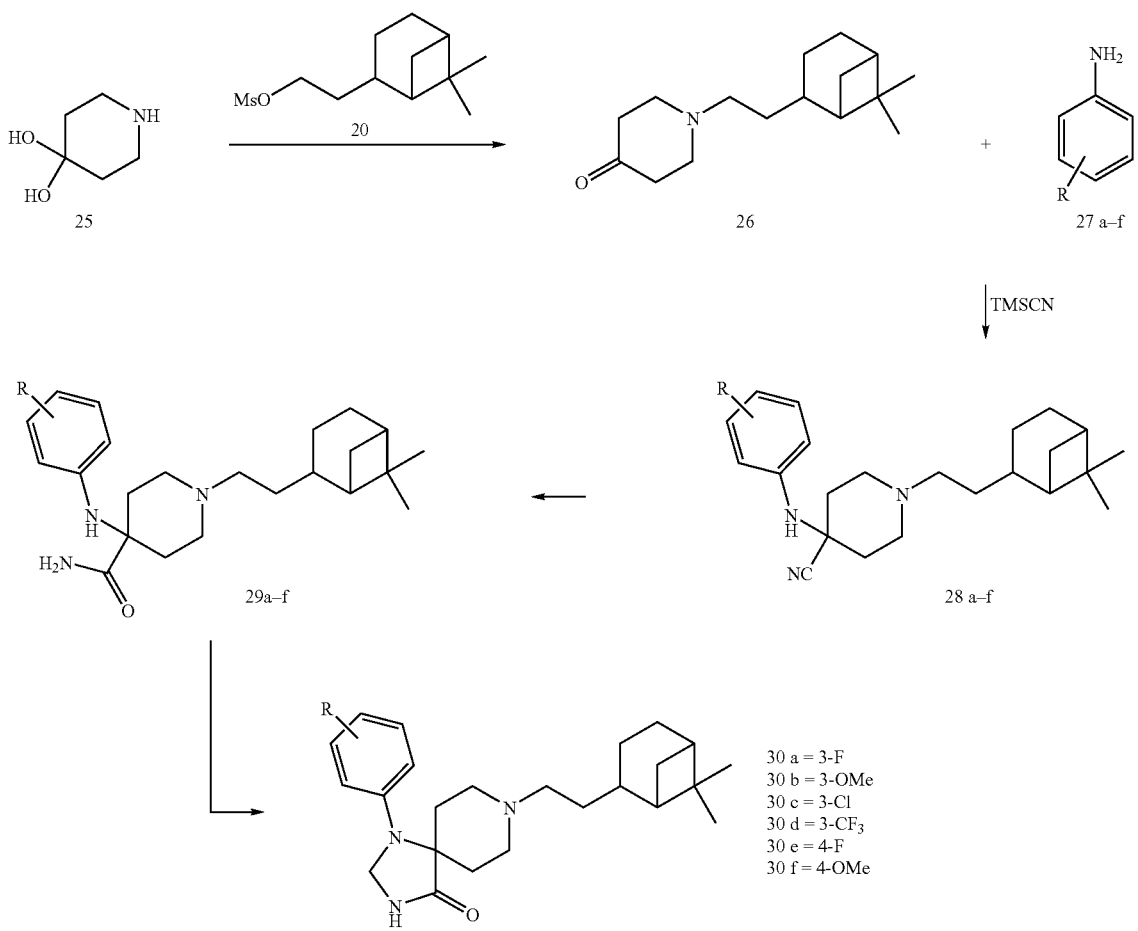

30 a = 3-F
30 b = 3-OMe
30 c = 3-Cl
30 d = 3-CF$_3$
30 e = 4-F
30 f = 4-OMe (In the scheme above TMSCN = trimethylsilylcyanide)

8-[2-(6,6-Dimethyl-bicyclo[3.1.1]hept-2-yl)-ethyl]-3-(3-methylamino-propyl)-1-phenyl-1,3,8-triaza-spiro[4.5]decan-4-one (24) [example nr. 13 in tables below]

The crude spiro compound (23) (162.8 g; 0.36 mol) was dissolved in methylamine/EtOH solution (Fluka, 8M; 1154 ml; 9.23 mol). Sodium iodide (2.16 g; 0.014 mol) was added and the solution was stirred at 70° C. under N$_2$-atmosphere for 3 days. After cooling the reaction mixture was diluted with water and EtOAc (500 ml each). The aqueous layer was extracted with EtOAc (3×800 ml). The organic layer was washed with brine (500 ml). After drying on Na$_2$SO$_4$ the solvent was evaporated to yield a yellow oil. This oil was purified by column chromatography (SiO$_2$; CH$_2$Cl$_2$/MeOH 90:10; containing 1% 7N NH$_3$/MeOH) to yield 30 g of (24) with a purity of 93% (according to HPLC/MS) and 85 g of (24) with a purity of 96% (115 g; 0.25 mol; 70%).

1-[2-(6,6-Dimethyl-bicyclo[3.1.1]hept-2-yl)-ethyl]-piperidin-4-one (26):

A mixture of 61.1 g (0.40 mol) of piperidone hydrate hydrochloride (25), 112.8 g (0.46 mol) of dihydronopol mesylate (20), 69.0 g (0.46 mol) of NaI, 273 g (1.97 mol) of K$_2$CO$_3$ and 4.3 l of MEK was refluxed overnight. The mixture was cooled to room temperature and concentrated in vacuo. The residue was dissolved in dichloromethane (1.5 l) and water (1.5 l) and the layers were separated. The organic layer was washed with water (1 l) and dried over Na$_2$SO$_4$. The layer was concentrated in vacuo to give 113 g of crude product, which was purified by column chromatography (SiO$_2$, heptane:EtOAc, 6:1→1:1) to yield 77.7 g (0.31 mol, 78%) of compound (26) as an orange oil.

1-[2-(6,6-Dimethyl-bicyclo[3.1.1]hept-2-yl)-ethyl]-4-(3-fluoro-phenylamino)-piperidine-4-carbonitrile (28a)

A solution of 20.0 g (80.2 mmol) of (26) and 8.4 ml (87 mmol) of 3-fluoroaniline (27a) in 65 ml of acetic acid was cooled with a cold water bath. 10.7 ml (80.2 mmol) of trimethylsilylcyanide were added dropwise over a period of 10 min. maintaining the temperature below 40° C. The mixture was stirred for 2 h at room temperature and poured into a mixture of aqueous ammonia (80 ml) and ice (80 g). The pH was adjusted to 10 with concentrated $NH_3$. The mixture was extracted with chloroform (3×200 ml). The combined organic layers were dried over $Na_2SO_4$ and concentrated in vacuo to give 40.0 g of crude product, which was purified by column chromatography ($SiO_2$, heptane: EtOAc, 1:1) to give 28.7 g (77.7 mmol, 97%) of (28a). It is also possible to use crude product in the next step without purification.

1-[2-(6,6-Dimethyl-bicyclo[3.1.1]hept-2-yl)-ethyl]-4-(3-fluoro-phenylamino)-piperidine-4-carboxylic Acid Amide (29a)

A mixture of 28.7 g (78 mmol) (28a), 135 ml of formic acid and 135 ml of acetic anhydride was stirred at room temperature for 1 day. The reaction was monitored by $^1$H-NMR and MS. After completed reaction the reaction mixture was poured into ice-water (800 ml). The pH was adjusted to 10 by the addition of 33% NaOH (aq). The aqueous layer was extracted with DCM (3×1 l). The combined organic layers were dried over $Na_2SO_4$ and concentrated in vacuo. The residue was dissolved in 550 ml tert.-butylalcohol, 45 ml water and 45 ml concentrated aqueous ammonia. The 90 ml of 35% hydrogen peroxide were added drop wise at room temperature. The mixture was stirred overnight. The reaction was monitored by TLC. 900 ml of water were added and the mixture was extracted with DCM (3×500 ml). The combined organic layers were dried over $Na_2SO_4$ and concentrated in vacuo to give 29.3 g (76 mmol, 98%) of (29a) as a yellow solid, which was used in the next step without purification.

8-[2-(6,6-Dimethyl-bicyclo[3.1.1]hept-2-yl)-ethyl]-1-(3-fluoro-phenyl)-1,3,8-triaza-spiro[4.5]decan-4-one (30a): [Example Nr. 9 in Tables Below]

A solution of 29.3 g (76 mmol) of (29a) in 400 ml formamide was heated for 2 h at 200° C. The solution turned from yellow to black. The reaction was monitored by $^1$H-NMR. After completed reaction the mixture was cooled to room temperature and poured into ice-water (800 g). The mixture was extracted with DCM (6×1 l). The combined organic layers were dried over $Na_2SO_4$ and concentrated in vacuo. The residue was dissolved in 1.2 l of methanol and 4.3 g (114 mmol) of sodiumborohydride were added portion wise. The mixture was stirred for 1 h at room temperature and another hour at 60° C. The reaction mixture was cooled to room temperature and quenched with 25 ml of water. The solvent was evaporated in vacuo. The residue was dissolved in 750 ml of ammonia and extracted with DCM (7×1.5 l). The combined organic layers were dried over $Na_2SO_4$ and concentrated in vacuo to give 24.8 g of crude product, which was purified by column chromatography ($SiO_2$, heptane: EtOAc, 1:1→1:3). Trituration with $Et_2O$ of the eluated product yielded 3.44 g (8.6 mmol, 11.3% from compound (26)) of compound (30a) as a white solid.

8-[2-(6,6-Dimethyl-bicyclo[3.1.1]hept-2-yl)-ethyl]-1-(3-methoxy-phenyl)-1,3,8-triaza-spiro[4.5]decan-4-one (30b): [example nr. 8 in tables below]

The sequence was repeated starting from 68.0 g (0.27 mol) of (26); Compound (30b) was purified by column chromatography and trituration with diethylether to yield 13.9 g (34 mmol, 12% yield from (26)) as an off-white solid.

8-[2-(6,6-Dimethyl-bicyclo[3.1.1]hept-2-yl)-ethyl]-1-(3-chloro-phenyl)-1,3,8-triaza-spiro[4.5]decan-4-one (30c): [example nr. 7 in tables below]

The sequence was repeated starting from 67.4 g (0.27 mol) of (26); Compound (30c) was purified by column chromatography and trituration with diethylether to yield 7.42 g (17.8 mmol, 6.6% yield from (26)) as an off-white solid.

8-[2-(6,6-Dimethyl-bicyclo[3.1.1]hept-2-yl)-ethyl]-1-(3-trifluoromethyl-phenyl)-1,3,8-triaza-spiro[4.5]decan-4-one (30d): [example nr. 10 in tables below]

For compound (30d) the same sequence was performed, but instead of the desired product, compound (29d) was isolated. Therefore the sequence was partially repeated. The compound was formylated with formic acid and acetic anhydride, heated in formamide and finally reduced with sodiumborohydride. The crude product was purified by column chromatography ($SiO_2$, EtOAc) and subsequently triturated with diethylether to yield 7.39 g (6.6% overall yield from (26)) as a white solid.

8-[2-(6,6-Dimethyl-bicyclo[3.1.1]hept-2-yl)-ethyl]-1-(4-fluoro-phenyl)-1,3,8-triaza-spiro[4.5]decan-4-one (30e): [example nr. 5 in tables below]

The sequence was repeated starting from 45.0 g (0.18 mol) of (26); Compound (30e) was purified by column chromatography and trituration with diethylether to yield 9.82 g (24.5 mmol, 13.6% yield from (26)) as a grey solid.

8-[2-(6,6-Dimethyl-bicyclo[3.1.1]hept-2-yl)-ethyl]-1-(4-methoxy-phenyl)-1,3,8-triaza-spiro[4.5]decan-4-one (30f): [example nr. 6 in tables below]

The sequence was repeated starting from 45.0 g (0.18 mol) of (26); Compound (30f) was purified by column chromatography and trituration with diethylether to yield 8.94 g (21.7 mmol, 12.1% yield from (26)) as a white solid.

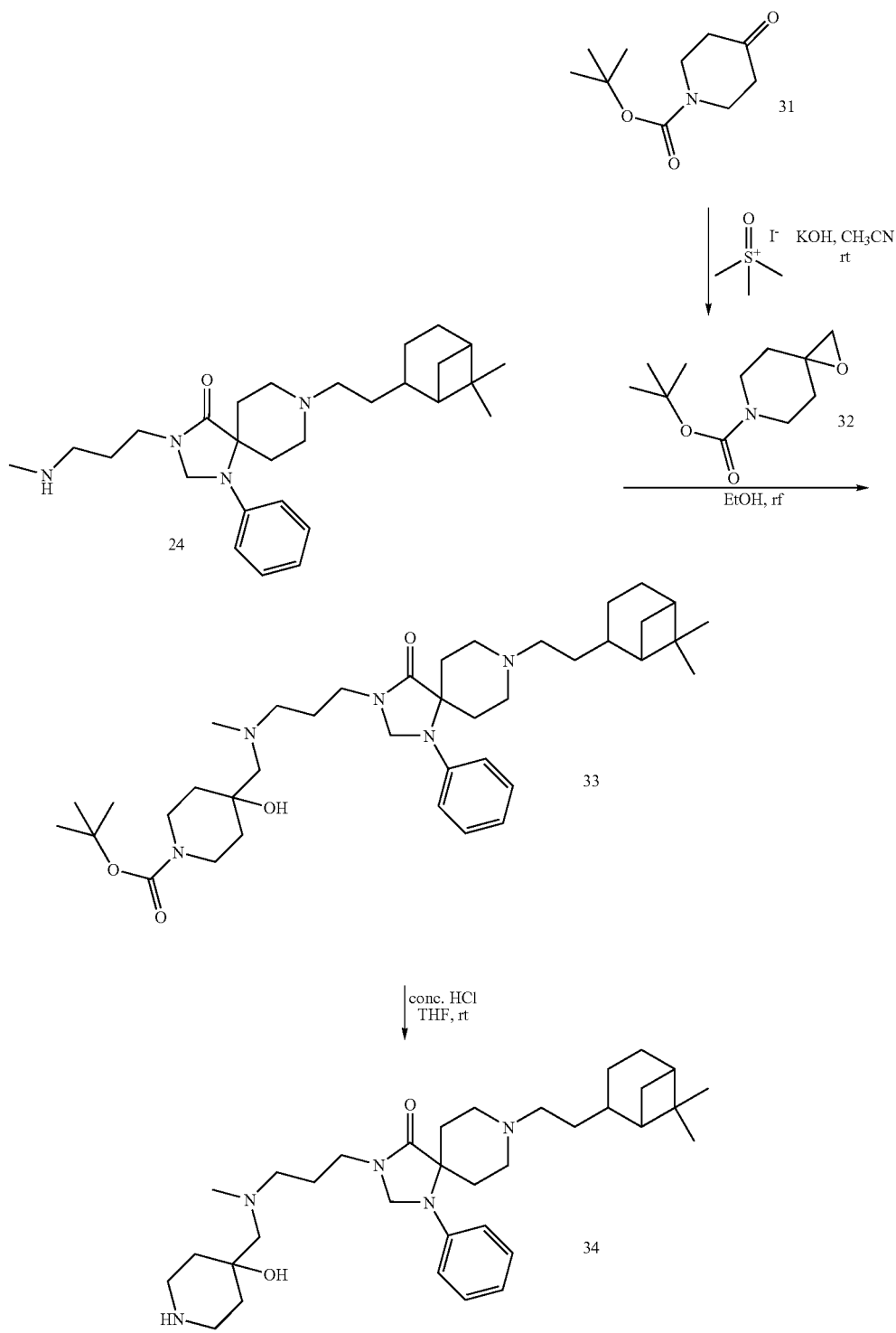

1-Oxa-6-aza-spiro[2,5]octane-6-carboxylic acid tert-butyl ester (32)

To a solution of 44.9 g (0.225 mol) of 4-oxo-piperidine-1-carboxylic acid tert-butyl ester (31) in 500 ml acetonitrile was added successively 59.5 g (0.27 mol) trimethyl sulphoxonium iodide and 18.9 g (0.338 mol) fine crushed potassium hydroxide. The reaction mixture was vigorously stirred for two days under a nitrogen atmosphere at room temperature. After complete conversion the solvent was evaporated in vacuo and the residue was taken up in dichloromethane. The organic layer was washed with aqueous citric acid solution (6×), dried over sodium sulphate and concentrated in vacuo. This crude product was used without further purification for the next step (43.5 g, 0.204 mol, 90.6% yield).

4-{[(3-{8-[2-(6,6-Dimethyl-bicyclo(3.1.1]hept-2-yl)-ethyl]-4-oxo-1-phenyl-1,3,8-triaza-spiro[4.5]dec-3-yl} propyl)-methyl-amino]-methyl}-4-hydroxy-piperidine-1-carboxylic acid tert-butyl ester (33): [example nr. 35 in tables below]

2.6 g (5.74 mmol) of compound (24) was placed in a flask and diluted with 20 ml ethanol. To this solution was added 1.88 g (8.81 mmol) of the epoxide (32) and the mixture was heated to reflux until TLC showed complete conversion. For work-up the solvent was evaporated and the residue was taken up with ethyl acetate. After washing with aqueous potassium carbonate solution drying over sodium sulphate and concentration in vacuo the raw material was purified via flash column chromatography yielding a light yellow viscous oil (3.51 g, 5.15 mmol, 89.8% yield).

8-[2-(6,6-Dimethyl-bicyclo[3.1.1]hept-2-yl)-ethyl]-3-{3-[(4-hydroxy-piperidin-4-ylmethyl)-methyl-amino]-propyl}-1-phenyl-1,3,8-triaza-spiro[4.5]decan-4-one (34): [example nr. 37 in tables below]

The Boc-derivative (33) (2.79 g, 4.19 mmol) was dissolved in tetrahydrofurane (25 ml). To this solution was added 2 ml of concentrated aqueous HCl solution and the resulting mixture was stirred at room temperature over night. After TLC analysis indicated complete conversion the solvent was removed under reduced pressure and the resulting residue was dissolved in ethyl acetate. Washing with potassium carbonate solution, drying of the organic layer with sodium sulphate and concentration in vacuo provided the pure title compound as a light yellow viscous oil (2.37 g, 3.8 mmol, 90.7% yield).

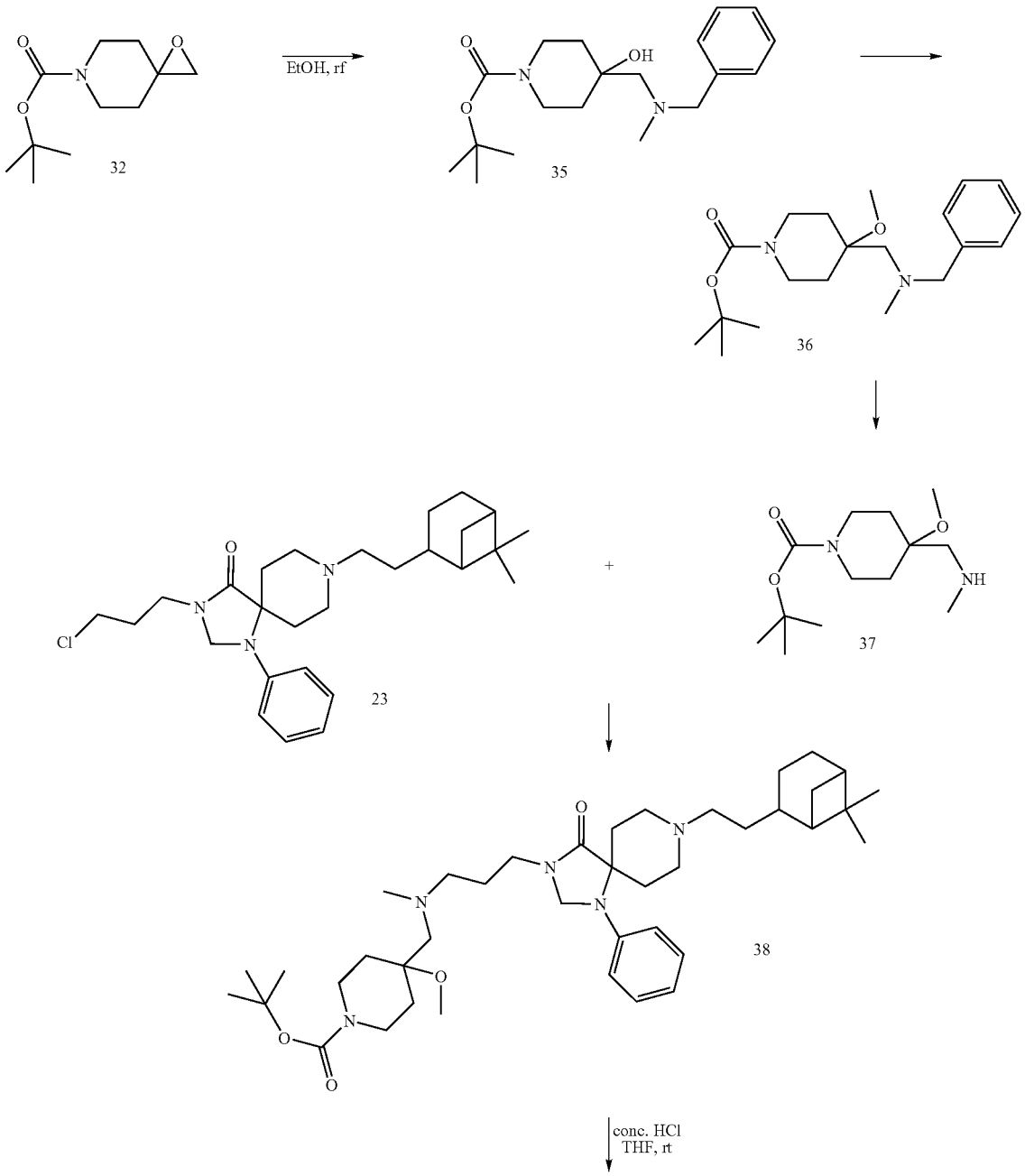

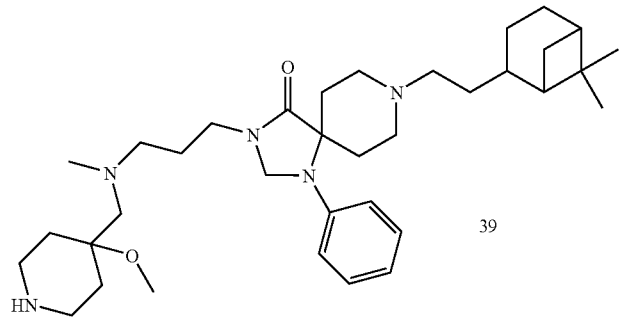

4-[(Benzyl-methyl-amino)-methyl]-4-hydroxy-piperidine-1-carboxylic acid tert-butyl ester (35)

Epoxide (32) (46 g, 216 mmol) was dissolved in dioxane (300 ml). Benzyl methylamine (75 ml, 583 mmol) was added and the mixture was stirred at reflux for 90 h. TLC analysis revealed complete conversion. The mixture was evaporated to dryness. The excess of benzyl methylamine was removed by evaporation in vacuo (0.05 mbar, 80° C.). Yield: 69.3 g of aminoalcohol (35) (96%) as an orange oil.

4-[(Benzyl-methyl-amino)-methyl]-4-methoxy-piperidine-1-carboxylic acid tert-butyl ester (36)

Alcohol (35)-(69.3 g, 200 mmol) was dissolved in dimethyl formamide (500 ml). NaH (9.2 g 230 mmol), washed with pentane, was added in 5 portions over 30 min. After complete addition the mixture was stirred at ambient temperature for 45 min. Methyl iodide (14.8 ml, 240 mmol) was added over 1.5 min. The mixture was stirred for 1.5 h at ambient temperature. TLC analysis revealed ca. 80-90% conversion. Extra NaH, 0.8 g, 20 mmol) and methyl iodide (1.2 ml, 20 mmol) was added and the mixture was stirred for another 2 h at ambient temperature. The excess of NaH was destroyed with water (100 ml) and the mixture was further diluted with water (3.5 l). The mixture was extracted with ethyl acetate (2×1 l, 500 ml). The organic layer was washed with brine (1 l), dried over $Na_2SO_4$ and concentrated to dryness. The traces of dimethyl formamide were removed by evaporation in vacuo (0.4 mbar, 80° C.). The remaining mixture was purified over silica (eluent: heptane/ethyl acetate, 4/1 to 3/1 v/v). Yield: 55.2 g of amine (36) (80%) as light yellow oil.

4-Methoxy-4-methylaminomethyl-piperidine-1-carboxylic acid tert-butyl ester (37)

Amine (36) (55 g, 158 mmol) was dissolved in ethyl acetate (500 ml). Pd—C (10%, wet, 5 g) was added and the mixture was stirred for 23 h under hydrogen atmosphere (1 bar). TLC analysis revealed incomplete conversion. Extra Pd—C (2.5 g) was added and the mixture was stirred under $H_2$ (1 bar) for 110 h. NMR analysis revealed complete conversion. The mixture was filtrated over Celite, the Celite crop was washed with ethyl acetate and the filtrate was evaporated to dryness. The residue was purified by distillation (bulb to bulb, 0.04 mbar, 130° C.) giving 35 g of compound (37) (86%) as colorless oil.

The synthesis of 8-[2-(6,6-Dimethyl-bicyclo[3.1.1]hept-2-yl)-ethyl]-3-{3-[(4-methoxy-piperidin-4-ylmethyl)-methyl-amino]-propyl}-1-phenyl-1,3,8-triaza-spiro[4.5]decan-4-one 39 [example nr. 45 in tables below] starting with chlorine. (23) and amine (36) was performed like described below (general methods).

Library Design with 8-[2-(6,6-Dimethyl-bicyclo[3.1.1]hept-2-yl)-ethyl]-3-(2-methylamino-ethyl)-1-phenyl 1,3,8-triaza spiro[4.5]decan-4-one as starting material

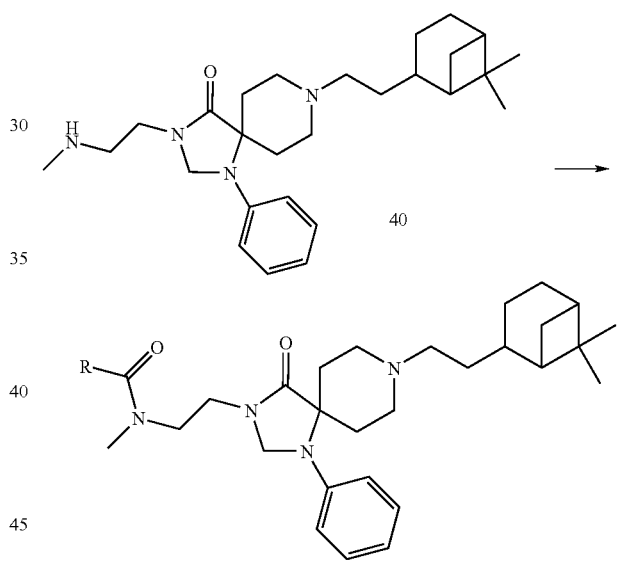

Amide Library, Method I:

The N-methyl amine (40) (1.832 g, 4.24 mmol) was dissolved in 170 ml dichloro-methane. This core solution was used to produce amides with various acid chloride solutions in the following manner: 2 ml of the core solution (0.05 mmol of (40)) was treated with polymer bound morpholine (0.162 mmol). After stirring for 20 min. at room temperature a solution of the corresponding acid chloride (0.06 mmol) in 2 ml dichloromethane was added and stirring was continued for 1 day at room temperature. The reaction was monitored by TLC analysis. To get rid of remaining acid chloride and N-methyl amine derivative polymer bound trisamine and isocyanate reagents (both are used as scavengers) were added, respectively. Again stirring was continued at room temperature over night before the polymers were removed by filtration. The filtrates were concentrated under reduced pressure. Using this protocol 69 compounds have been synthesized. The affinity of each synthesized amide to the human ORL1 receptor was measured in the in vitro binding assay.

Amide Library, Method II:

To 200 μl of the stock solutions of the cores (0.25M in THF) was added 200 μl of the stock solutions of the acid chlorides (0.25M in THF), followed by 50 μl of the triethylamine solution (1.0M in THF). After shaking overnight (17 hrs) at 30° C. the solvent was evaporated and the crude products were taken up in DMSO for analysis. (Remark: insoluble reagents were added by hand). Using this protocol 26 compounds have been synthesized. The affinity of each synthesized amide to the human ORL1 receptor was measured in the in vitro receptor binding assay.

Epoxide Opening Library:

The N-methyl amine (40) (1.316 g, 3.0 mmol) was dissolved in 120 ml isopropyl alcohol. This core solution was used to produce amino alcohols with various epoxide solutions in the following manner: to 2 ml of the core solution (0.05 mmol of (40)) was added a solution of the corresponding epoxide (0.075 mmol) in 2 ml isopropyl alcohol. This mixture was heated to 80° C. for 2 days. TLC analysis was used to monitor the reactions. For work-up polymer bound trisamine and isocyanate reagents (both are used as scavengers) were added, respectively. Again stirring was continued at room temperature for two days before the polymers were removed by simple filtration. The filtrates were concentrated under reduced pressure. Using this protocol 27 compounds have been synthesized. The affinity of each synthesized amide to the human ORL1 receptor was measured in the in vitro receptor binding assay.

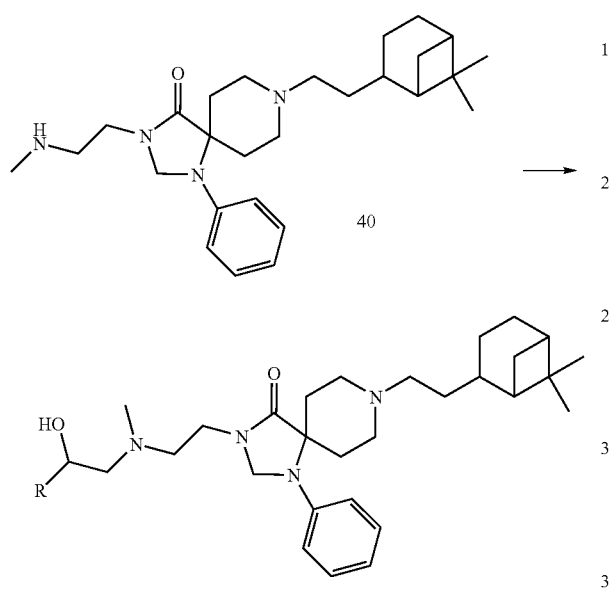

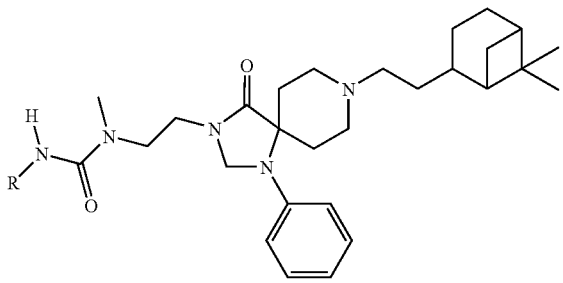

Urea Library:

To 200 μl of the stock solutions of the cores (0.25M in THF) was added 200 μl of the stock solutions of the isocyanides (0.25M) in THF. The vials were capped and after shaking overnight (17 hrs) at 30° C. the solvent was evaporated and the crude products were taken up in DMSO for analysis. Using this protocol 71 compounds have been synthesized.

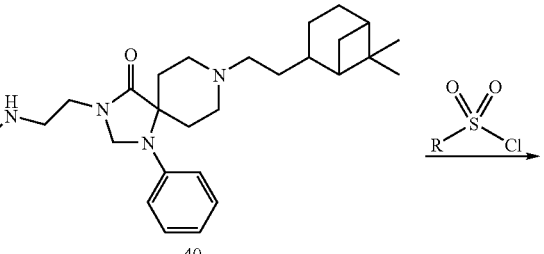

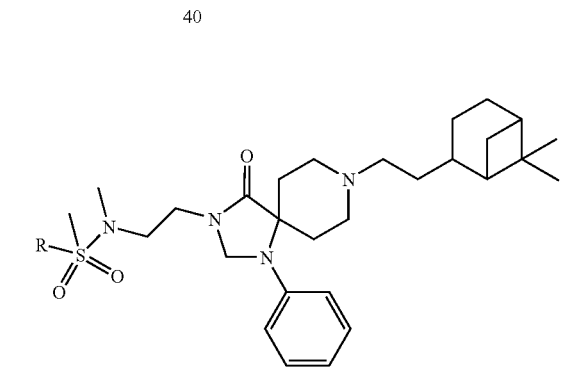

Sulfonamide Library:

Stock solutions prepared of the cores (0.25M) in THF and of the sulfonylchlorides (0.25M) in THF. To 200 μl of the core solution was added 200 μl of the sulfonylchlorides, followed by 50 μl of a 1.0M DIPEA solution in THF. Vials were capped and heated at 30° C. for 16 hours. Products were purified by means of cat-ion exchange Solid Phase Extraction. Solvent was evaporated and the crude products were taken up in DMSO for analysis. Using this protocol 69 compounds have been synthesized.

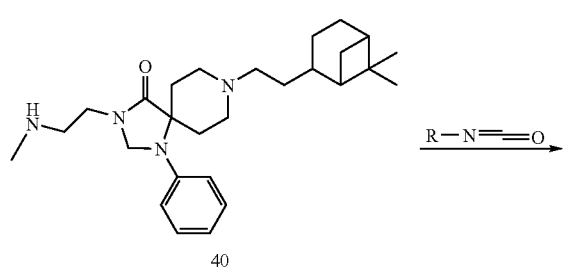

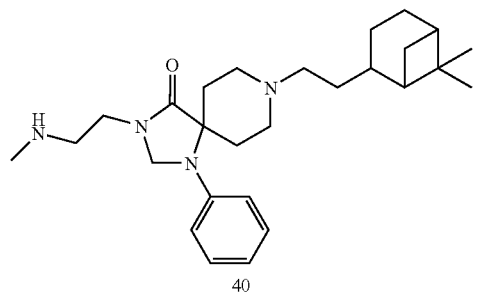

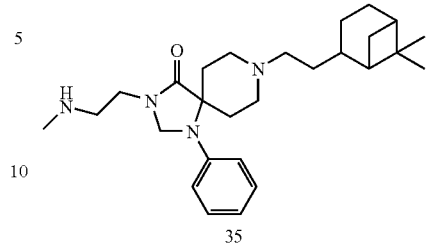

for analysis. Using this protocol 61 compounds have been synthesized.

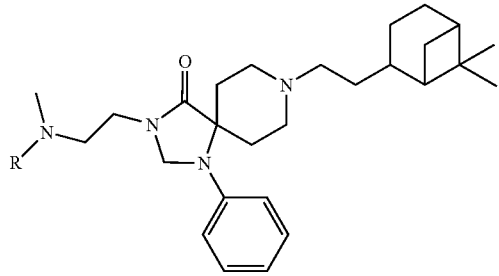

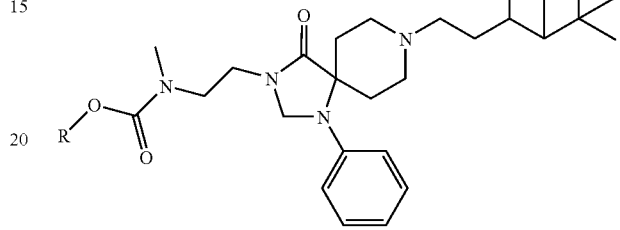

Alkylation Library:

Stock solutions were prepared of the cores (0.25M) in DMF and of the halides (0.25M) in DMF. To 200 μl core solution was added 200 μl of the halide solution including 1 equivalent of KI, followed by 50 μl of a diisopropylethylamine solution (1.0 M). Vials were capped and heated for 17 hours. Specific modifications: alpha-halo ketones at 30° C.; the others at 60° C. Products were purified by means of cat-ion exchange Solid Phase Extraction. The solvent was evaporated and the crude products were taken up in DMSO Carbamate Library:

To a solution of cores (200 μL, 0.25M) in tetrahydrofuran was added a solution of diisopropylethylamine (50 μL, 2M) in THF followed by a stock solution of chloroformate (200 μL, 0.25M) in THF. The vials were capped and shaken for 24 h at 30 degrees. Products were purified by means of cat-ion exchange Solid Phase Extraction. The solvent was evaporated and the crude products were taken up in DMSO for analysis. Using this protocol 21 compounds have been synthesized.

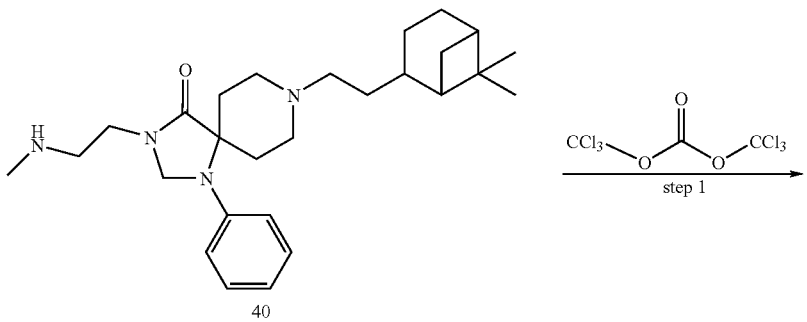

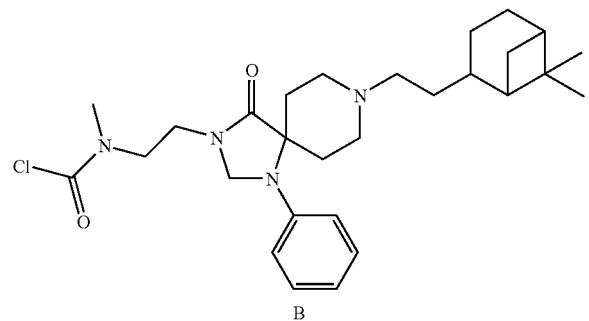

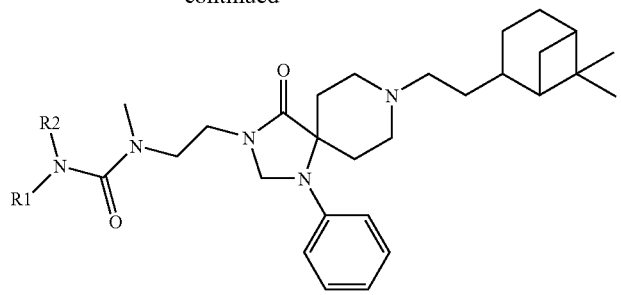

Tert.-Urea Library:

Procedure:

This procedure was followed for the reaction of the carbamoylchloride and 2×75 secondary amines. All vials and flasks have to been dried at 100° C. under vacuum. All the solvents have to been dried (mol sieves for $CH_2Cl_2$ and $K_2CO_3$ for $CH_3CN$).

Step 1

9.2 mmol of the core was dissolved in 92 ml of $CH_2Cl_2$ (mol. sieve 4 Å)=0.1 M solution. To this solution was added 5.68 ml of DIPEA (3.5 eq.). The mixture was cooled to 0° C. (ice-bath) and a solution of 2.728 g (4.6 mmol) of triphosgene in 36.8 ml of $CH_2Cl_2$ was added at once. The ice-bath was removed and the mixture was stirred for 30 minutes. The reaction was monitored by TLC and LC-MS. The reaction mixture was concentrated under reduced pressure for 1 hr at 40° C. and 20 mbar. The crude product was dissolved in 36.8 ml of $CH_3CN$ (dried on $K_2CO_3$) and 1.92 ml of DIPEA was added, obtaining a 0.25M solution of carbamoylchloride (B).

Step 2

To 200 µl (0.25M) of secondary amines in $CH_3CN$ was added 200 µl (0.25M) carbamoylchloride (B) in $CH_3CN$, followed by 1 equivalent of siisopropylamine. The vials were capped and shaken for 17 hours at 30° C. Reaction mixtures were concentrated, dissolved in EtOAc and washed with 5% $NaHCO_3$-solution. The solvent was evaporated and the crude products were taken up in DMSO for analysis. Using this protocol 49 compounds have been synthesized.

Syntheses of Individual Compounds

Synthons Used for the Preparation of the Described Examples:

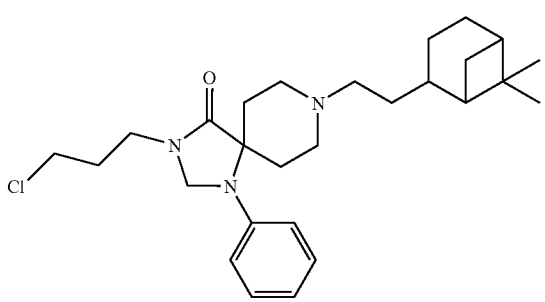

23

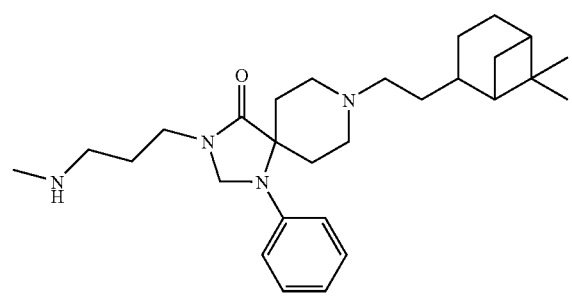

24

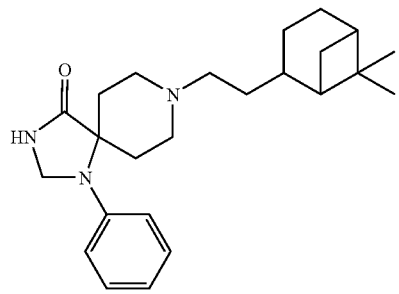

22

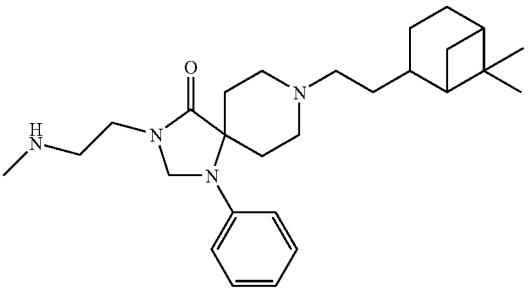

40

Alkylation Reactions with Compounds (24)/(40): General Procedure:

The methyl amine compound was dissolved in THF and 1.1 equivalent of diisopropyl ethyl amine was added. To this mixture was added the appropriate alkylation reagent (1 equivalent) and the solution was heated to reflux and was monitored by TLC. After complete conversion the solution was concentrated and the residue was taken up with aqueous sodium carbonate solution. The aqueous layer was extracted several times with dichloromethane. The combined organic layers were dried over sodium sulphate, concentrated and the raw product was further purified via column chromatography (SiO$_2$, ethyl acetate or CH$_2$Cl$_2$/MeOH as eluents).

3-{3-[(2,4-Difluoro-benzyl)-methyl-amino]-propyl}-8-[2-(6,6-dimethyl-bicyclo[3.1.1]hept-2-yl)-ethyl]-1-phenyl-1,3,8-triaza-spiro[4.5]decan-4-one yield: 52% [example nr. 23 in tables below]

8-[2-(6,6-Dimethyl-bicyclo[3.1.1]hept-2-yl)-ethyl]-3-[3-(methyl-pyridin-4-ylmethyl-amino)-propyl]-1-phenyl-1,3,8-triaza-spiro[4.5]decan-4-one yield: 32% [example nr. 25 in tables below]

8-[2-(6,6-Dimethyl-bicyclo[3.1.1]hept-2-yl)-ethyl]-3-[3-(methyl-pyridin-3-ylmethyl-amino)-propyl]-1-phenyl-1,3,8-triaza-spiro[4.5]decan-4-one, yield: 15% [example nr. 26 in tables below]

Variation:

8-[2-(6,6-Dimethyl-bicyclo[3.1.1]hept-2-yl)-ethyl]-3-[3-(methyl-pyridin-2-yl-amino)-propyl]-1-phenyl-1,3,8-triaza-spiro[4.5]decan-4-one 1.7 g of the methyl amine compound 24 was dissolved in 4 ml of 2-Fluoropyridin and refluxed at 150° C. After complete conversion the reaction mixture was poured into water and the aqueous layer was extracted with ethyl acetate for several times. The combined organic layers were dried over sodium sulphate, concentrated in vacuo and purified via column chromatography (SiO$_2$; ethyl acetate). yield: 60% [example nr. 83 in tables below].

Epoxide Opening Reactions with Compound (24)/(40):

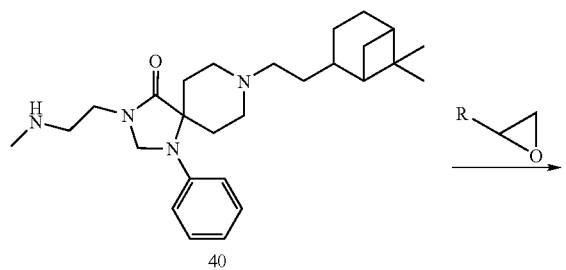

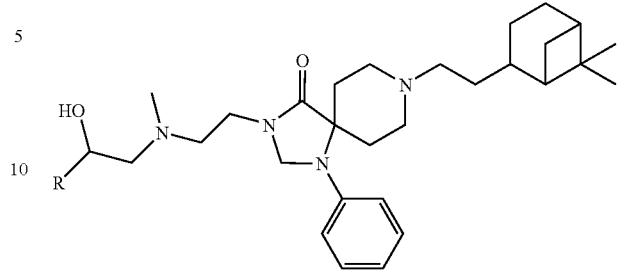

General Procedure:

The methylamine compound was dissolved in EtOH/H$_2$O (v/v=10/1, 2 mmol/ml). After addition of the epoxide (1.5 eq) the mixture was heated to reflux and the reaction was monitored by TLC. After complete conversion the solution was concentrated and the residue was taken up with aqueous potassium carbonate solution. The aqueous layer was extracted several times with ethyl acetate. The combined organic layers were dried over sodium sulphate, concentrated and the raw product was further purified via column chromatography (SiO$_2$, CH$_2$Cl$_2$/MeOH as eluents).

3-{3-[(2,3-Dihydroxy-propyl)-methyl-amino]-propyl}-8-[2-(6,6-dimethyl-bicyclo[3.1.1]hept-2-yl)-ethyl]-1-phenyl-1,3,8-triaza-spiro[4.5]decan-4-one yield: 31% [example nr. 92 in tables below]

3-{2-[(2,3-Dihydroxy-propyl)-methyl-amino]-ethyl}-8-[2-(6,6-dimethyl-bicyclo[3.1.1]hept-2-yl)-ethyl]-1-phenyl-1,3,8-triaza-spiro[4.5]decan-4-one yield: 46% [example nr. 178 in tables below]

8-[2-(6,6-Dimethyl-bicyclo[3.1.1]hept-2-yl)-ethyl]-3-{3-[(2-hydroxy-cyclohexyl)-methyl-amino]-propyl}-1-phenyl-1,3,8-triaza-spiro[4.5]decan-4-one [example nr. 29 in tables below] yield: 80% (remark: potassium carbonate as additional base (2.5 eq) was used in the synthesis)

8-[2-(6,6-Dimethyl-bicyclo[3.1.1]hept-2-yl)-ethyl]-3-{3-[(2-hydroxy-3-morpholin-4-yl-propyl)-methyl-amino]-propyl}-1-phenyl-1,3,8-triaza-spiro[4.5]decan-4-one [example nr. 93 in tables below] yield: 65%

Substitution Reactions with Compound (23):

Generally, substitutions were performed in an aprotic polar solvent (e.g. acetonitrile, dimethylsulphoxide or N-dimethyl formamide) in the following manner:

The starting material was dissolved in the appropriate solvent. 0.1 eq of sodium iodine and 2 eq of a base (e.g. potassium carbonate or diisopropyl ethyl amine) were placed into the reaction flask before the corresponding amine (2 to 4 eq) was added to this solution. The reaction mixture was heated and monitored by TLC analysis. After standard aqueous work-up procedures the residues were further purified via column chromatography (SiO$_2$, CH$_2$Cl$_2$/MeOH as eluents).

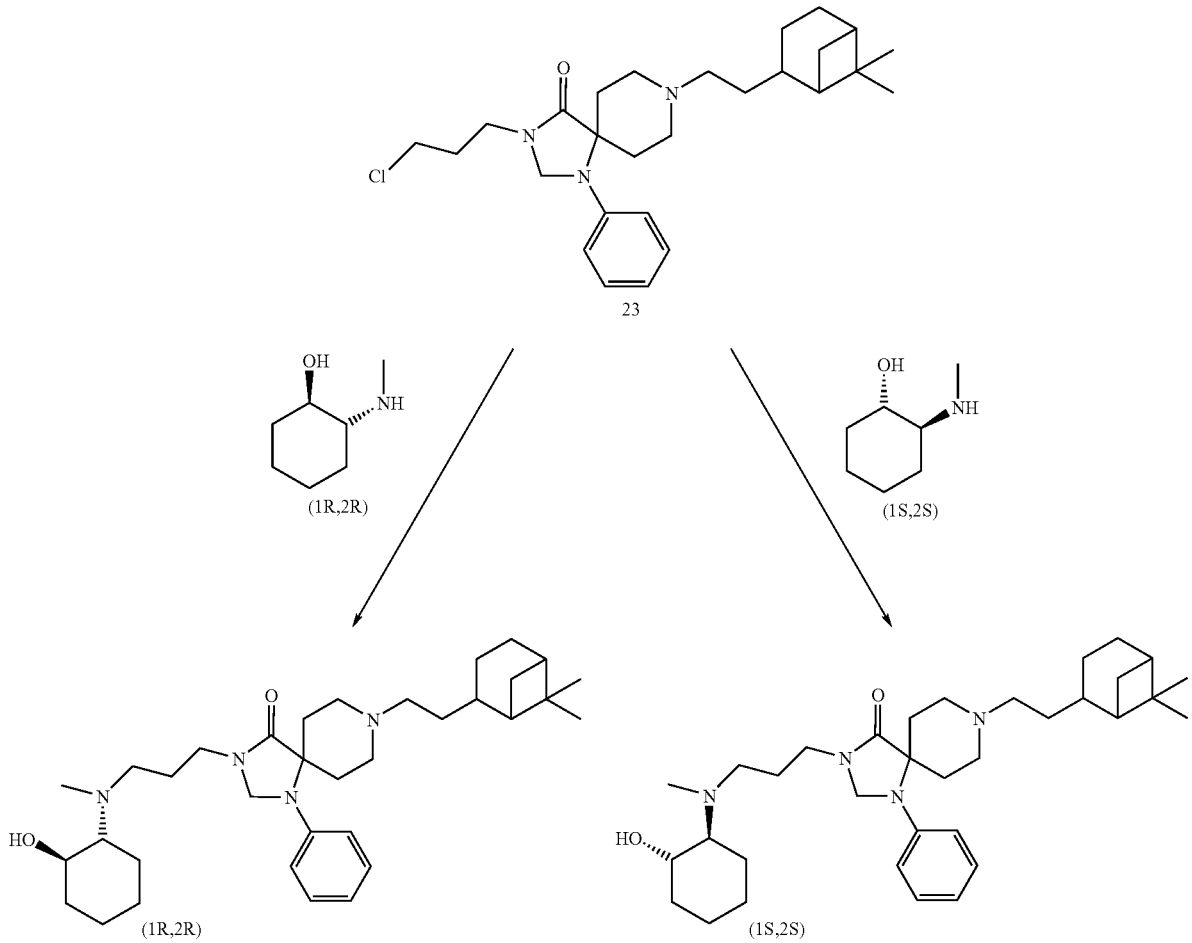

Preparation of Optically Pure Starting Materials According to Literature procedures [*J. Prakt. Chem.* 329, 235 (1987)]

2-Methylamino-cyclohexanol

Cyclohexene oxide (147 g, 1.5 mol) was dissolved in a ethanolic 8 M methylamine solution (750 ml) and stirred at 40° C. for 16 h. The reaction mixture was concentrated in vacuo to give racemic 2-methylaminocyclohexanol as a slightly brown oil (195 g, 100%). According to GC-analysis this product was 99+% pure and used without further purification.

(1R,2R)-2-methylamino-cyclohexanol (R)-mandelic Acid Salt and (1S, 2S)-2-methylamino cyclohexanol (S)-mandelic Acid Racemic 2-methylamino-cyclohexanol (195 g, max 1.5 mol) and (R)-(−)-mandelic acid (228 g, 1.5 mol) were added to 2-propanol (1.2 l) and heated to reflux temperature. The solution was allowed to cool slowly to room temperature and was stirred overnight. The formed precipitate was collected by filtration, washed with 2-butanone and dried on air giving a white solid (160 g, enantiomeric excess (e.e.)=92%). The motherliquor was concentrated giving a brown oil (275 g) which solidified on standing. The white solid was heated for 10 min at reflux temperature in 2-butanone (1.7 l). The mixture was allowed to cool to room temperature under stirring and stirred at room temperature for 16 hours. The precipitate was collected by filtration and dried on air giving (1R,2R)-2-methylamino cyclohexanol (R)-mandelic acid salt (151.5 g, 538 mmol, 36%) as a white solid with an e.e. of 99%.

The first motherliquor (275 g, 0.98 mol) was added to a solution of NaOH (200 g, 5 mol) in water (800 ml) and brine (800 ml). Dichloromethane (400 ml) was added and the layers were separated after stirring for 15 min. The aqueous layer was again extracted with dichloromethane (3×400 ml). The combined dichloromethane layers were dried (Na$_2$SO$_4$) and concentrated to give a brown oil (118.5 g, 93.5% yield). This oil was Kugelrohr distilled (p=0.3 mbar, T=70-80° C.) to give (1S, 2S)-2-methylamino cyclohexanol (105 g, 813 mmol, 83% yield) with an e.e. of 66%. This enriched material was dissolved in 2-propanol (700 mL). (S)-(+)-mandelic acid (124 g, 815 mmol) was added and the mixture was heated to reflux temperature. The resulting solution was allowed to cool slowly to room temperature and stirred for 16 h at that temperature. The formed precipitate was collected by filtration, washed with 2-butanone and dried in air to give a white solid (172 g). This first salt was heated to reflux for 15 min in 2-butanone (2.0 l). The mixture (no clear solution was formed) was allowed to cool slowly to room temperature and stirred 16 h. The precipitate was collected by filtration and dried to give (1S, 2S)-2-methylamino cyclohexanol (S)-mandelic acid salt (160 g, 569 mmol, 38%) as a white solid with an e.e.>99%.

(1R,2R)-(–)-2-Methylamino-cyclohexanol [For configuration/rotation relationship see *J. Prakt. Chem.* 329, 235 (1987), and *Tetrahedron Asymm.*, 10, 4619 (1999)]

NaOH (108 g, 2.69 mol) was dissolved in water (350 ml). Brine (400 ml) was added and cooled to room temperature. Dichloromethane (300 ml) and (1R, 2R)-2-methylamino cyclohexanol (R)-mandelic acid salt (151.5 g, 538 mmol) were added and the mixture was stirred vigorously for 10 min. The layers were separated and the aqueous layer was again extracted with dichloromethane (3×200 ml). (separation of the layers is a time consuming process). The combined dichloromethane layers were dried ($Na_2SO_4$) and concentrated to give an oil (67.7 g, 97% yield). This oil was combined with two other batches of 2.3 g and 6.4 g (both with e.e.=99+%) and purified by Kugelrohr distillation (p=0.5 mbar, T=80-90° C.) giving a colorless oil (72.0 g, 92%) with 94% purity according to GC. This oil was again Kugelrohr distilled (p=0.3 mbar) giving two product containing fractions:
Fraction 1; T=40-60° C. 11.6 g with 89% purity according to GC,
Fraction 2; T=60-65° C.: 60.1 g G10302-1 as a colorless oil with 99% purity and an e.e. of 99.5%. $[\alpha]_{670}$=–51.5 (c=0.14, methanol).

(1S,2S)-(+)-2-Methylamino-cyclohexanol [For configuration/rotation relationship see *J. Prakt. Chem.* 329, 235 (1987), and *Tetrahedron Asymm.*, 10, 4619 (1999)]

NaOH (108 g, 2.69 mol) was dissolved in water (400 ml). Brine (400 ml) was added and cooled to room temperature. Chloroform (300 ml) and (1S, 2S)-2-methylamino cyclohexanol (S)-mandelic acid salt (160 g, 569 mmol) were added and the mixture was stirred vigorously for 5 min. The layers were separated and the aqueous layer was again extracted with chloroform (3×350 ml). The combined chloroform layers were dried ($Na_2SO_4$) and concentrated to give an oil (68 g, 93% yield). This oil was purified by Kugelrohr distillation (p=0.1 mbar) giving two product containing fractions:
Fraction 1; T=40-55° C. 17.5 g as a colorless oil with 99% purity according to GC,
Fraction 2; T=55-60° C.: 48.8 g as a colorless oil with 99.9% purity according to GC.
Both fractions were combined giving 66.2 g (512 mmol, 90%) as a colorless oil with an e.e. of 99.9% $[\alpha]670$=+53.6 (c=0.14, methanol).

8-[2-(6,6-Dimethyl-bicyclo[3.1.1]hept-2-yl)-ethyl]-3-{3R-[(2R-hydroxy-cyclohexyl)-methyl-amino]-propyl}-1-phenyl-1,3,8-triaza-spiro[4.5]decan-4-one [example nr. 30 in tables below]

2.5 g of the bicyclic chloro-compound (23) was dissolved in 5 ml of acetonitrile. To this solution was successively added 1.5 g (2 eq) of potassium carbonate, 90 mg (0.1 eq) sodium iodine, 780 mg of 1R,2R)-(–)-2-Methylamino-cyclohexanol and finally 3 drops of $H_2O$. This mixture was heated to reflux for 8 hours. For work up the reaction mixture was diluted with ethyl acetate and washed first with aqueous citric acid and afterwards with aqueous sodium hydrogen carbonate solution. The organic layer was dried over sodium sulphate, concentrated and the residue was further purified via column chromatography ($SiO_2$, $CH_2Cl_2$/MeOH as eluent) yielding 1.75 g (58%) of a light yellow oil.

8-[2-(6,6-Dimethyl-bicyclo[3.1.1]hept-2-yl)-ethyl]-3-{3S-[(2S-hydroxy-cyclohexyl)-methyl-amino]-propyl}-1-phenyl-1,3,8-triaza-spiro[4.5]decan-4-one [example nr. 31 in tables below]

The compound was prepared according to the protocol given above for the stereoisomer. Yield: 48% as a light yellow oil.

Boronic-acid-Mannich-reactions:

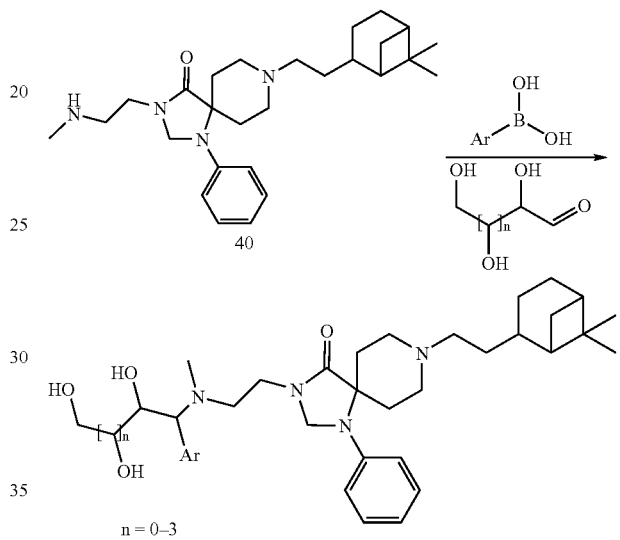

n = 0–3

The following experimental protocol was used to synthesize several compounds in the same manner starting with compound (40) and compound (24), respectively.

8-[2-(6,6-Dimethyl-bicyclo[3.1.1]hept-2-yl)-ethyl]-3-{3-[(1-furan-2-yl-2,3,4,5-tetrahydroxy-pentyl)-methyl-amino]-propyl}-1-phenyl-1,3,8-triaza-spiro[4.5]decan-4-one [example nr. 52 in tables below]

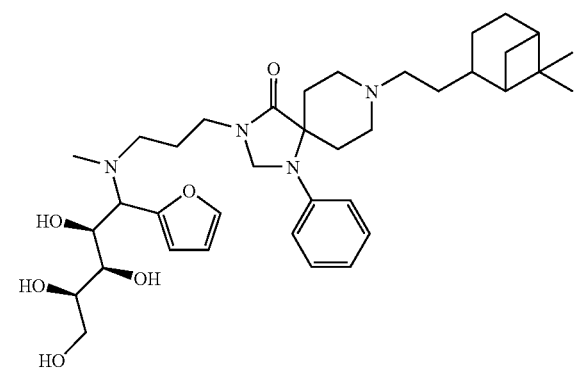

A solution of the amine (24) (2.66 g, 5.876 mmol) and 2-furanyl boronic acid (920 mg, 8.22 mmol) in 30 ml EtOH and 0.5 ml $H_2O$ is heated to 40° C. under vigorous stirring.

To this solution was added 1.06 g, (7.05 mmol) of D-(+)-xylose in small portions within 15 min at 40° C.

After 2.5 hours the reaction mixture was poured into aqueous $NaHCO_3$ solution and the aqueous layer was extracted 3 times with dichloromethane. The combined organic layers were concentrated and taken up in ethyl acetate. This organic layer was washed with aqueous citric acid (10%) several times. The combined aqueous layers were then neutralized with aqueous $NaHCO_3$ solution and the neutral aqueous layer was extracted with $CH_2Cl_2$. The combined organic extracts were dried over sodium sulphate and concentrated in vacuo to provide a crude yellow oil which was purified by column chromatography ($SiO_2$, ethyl acetate/methanol: 20/1 to 10/1). The purification yielded the title compound as an amorphous white solid (1.40 g, 2.14 mmol, 37%).

Alternative work-up procedure: After complete conversion (TLC) the reaction mixture was cooled to room temperature, 1 ml of trifluoroacetic acid was added and the remaining solution was stirred for 10 min at room temperature. Concentration in vacuo was followed by further purification of the raw product via column chromatography.

Using the same procedure as described above, the following examples were synthesized:

8-[2-(6,6-Dimethyl-bicyclo[3.1.1]hept-2-yl)-ethyl]-3-{3-[methyl-(2,3,4,5-tetrahydroxy-1-thiophen-2-yl-pentyl)-amino]-propyl}-1-phenyl-1,3,8-triaza-spiro[4.5]decan-4-one [example nr. 59 in tables below] yield: 80% (D-xylose and 2-thiophenyl boronic acid as starting materials)

8-[2-(6,6-Dimethyl-bicyclo[3.1.1]hept-2-yl)-ethyl]-3-{2-[methyl-(2,3,4,5-tetrahydroxy-1-thiophen-2-yl-pentyl)-amino]-ethyl}-1-phenyl-1,3,8-triaza-spiro[4.5]decan-4-one [example nr. 58 in tables below] yield: 13% (D-xylose and 2-thiophenyl boronic acid as starting materials)

8-[2-(6,6-Dimethyl-bicyclo[3.1.1]hept-2-yl)-ethyl]-3-{2-[(1-furan-2-yl-2,3,4,5,6-pentahydroxy-hexyl)-methyl-amino]-ethyl}-1-phenyl-1,3,8-triaza-spiro[4.5]decan-4-one [example nr. 55 in tables below] yield: 75% (D-glucose and 2-furanyl boronic acid as starting materials)

8-[2-(6,6-Dimethyl-bicyclo[3.1.1]hept-2-yl)-ethyl]-3-{2-[(1-furan-2-yl-2,3,4,5-tetrahydroxy-pentyl)-methyl-amino]-ethyl}-1-phenyl-1,3,8-triaza-spiro[4.5]decan-4-one [example nr. 53 in tables below] yield: 42% (D-xylose and 2-furanyl boronic acid as starting materials)

8-[2-(6,6-Dimethyl-bicyclo[3.1.1]hept-2-yl)-ethyl]-3-{2-[(1-furan-2-yl-2, 3, 4, 5-tetrahydroxy-pentyl)-methyl-amino]-ethyl}-1-phenyl-1,3,8-triaza-spiro[4.5]decan-4-one [example nr. 52 in tables below] yield: 60% (L-xylose and 2-furanyl boronic acid as starting materials)

8-[2-(6,6-Dimethyl-bicyclo[3.1.1]hept-2-yl)-ethyl]-3-{2-[(1-furan-2-yl-2,3-dihydroxy-propyl)-methyl-amino]-ethyl}-1-phenyl-1,3,8-triaza-spiro[4.5]decan-4-one [example nr. 49 in tables below] yield: 66% (D,L-glycerin aldehyde and 2-furanyl boronic acid as starting materials)

3-{2-[(2,3-Dihydroxy-1-thiophen-3-yl-propyl)-methyl-amino]-ethyl}-8-[2-(6,6-dimethyl-bicyclo[3.1.1]hept-2-yl)-ethyl]-1-phenyl-1,3,8-triaza-spiro[4.5]decan-4-one [example nr. 47 in tables below] yield: 39% (D,L-glycerin aldehyde and 3-thiophenyl boronic acid as starting materials)

8-[2-(6,6-Dimethyl-bicyclo[3.1.1]hept-2-yl)-ethyl]-3-{2-[methyl-(2,3,4,5-tetrahydroxy-1-thiophen-3-yl-pentyl)-amino]-ethyl}-1-phenyl-1,3,8-triaza-spiro[4.5]decan-4-one [example nr. 48 in tables below] yield: 28% (L-arabinose and 3-thiophenyl boronic acid as starting materials)

8-[2-(6,6-Dimethyl-bicyclo[3.1.1]hept-2-yl)-ethyl]-3-{2-[methyl-(2,3,4,5-tetrahydroxy-1-thiophen-3-yl-pentyl)-amino]-ethyl}-1-phenyl-1,3,8-triaza-spiro[4.5]decan-4-one [example nr. 55 in tables below] yield: 21% (L-xylose and 3-thiophenyl boronic acid as starting materials)

8-[2-(6,6-Dimethyl-bicyclo[3.1.1]hept-2-yl)-ethyl]-3-{2-[methyl-(2,3,4,5,6-pentahydroxy-1-thiophen-3-yl-hexyl)-amino]-ethyl}-1-phenyl-1,3,8-triaza-spiro[4.5]decan-4-one [example nr. 54 in tables below] yield: 16% (D-glucose and 3-thiophenyl boronic acid as starting materials)

The invention is further illustrated by means of the following specific examples (only intended to further illustrate the invention in more detail, and therefore are not deemed to restrict the scope of the invention in any way) listed in the table below and represented by the general formulae (1), (2) and (3):

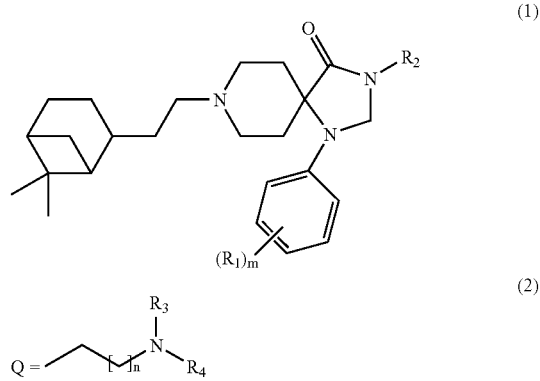

Where in the table below under the heading "stereochemistry" the name of a compound is given (e.g. (−)-cis-hydronopol or D-xylose), that means that the compound in question was used in the final reaction step.

| Ex. | $R_1$ | m | $R_2$ | n | $R_3$ | $R_4$ | stereochemistry |
|---|---|---|---|---|---|---|---|
| 1 | H | 1 | H | — | — | — | (−)cis-hydronopol |
| 2 | H | 1 | H | — | — | — | (−)trans-hydronopol |
| 3 | H | 1 | H | — | — | — | (+)cis-hydronopol |
| 4 | H | 1 | H | — | — | — | (+)trans-hydronopol |
| 5 | 4-F | 1 | H | — | — | — | |
| 6 | 4-$OCH_3$ | 1 | H | — | — | — | |
| 7 | 3-Cl | 1 | H | — | — | — | |
| 8 | 3-$OCH_3$ | 1 | H | — | — | — | |
| 9 | 3-F | 1 | H | — | — | — | |
| 10 | 3-$CF_3$ | 1 | H | — | — | — | |

-continued

| Ex. | R₁ | m | R₂ | n | R₃ | R₄ | stereochemistry |
|---|---|---|---|---|---|---|---|
| 11 | H | 1 | (1)* | — | — | — | |
| 12 | H | 1 | Q | 1 | H | CH₃ | |
| 13 | H | 1 | Q | 2 | H | CH₃ | |
| 14 | H | 1 | Q | 3 | H | CH₃ | |
| 15 | H | 1 | Q | 4 | H | CH₃ | |
| 16 | H | 1 | Q | 5 | H | CH₃ | |
| 17 | H | 1 | Q | 1 | CH₃ | Benzyl | |
| 18 | H | 1 | Q | 1 | CH₃ | 2-Morpholin-4-yl-ethyl | |
| 19 | H | 1 | Q | 2 | H | 3,4-Methylendioxybenzyl | |
| 20 | H | 1 | Q | 2 | H | 4-Sulfamoyl-benzyl | |
| 21 | H | 1 | Q | 2 | CH₃ | CH₃ | (−)-cis |
| 22 | H | 1 | Q | 2 | CH₃ | CH₃ | (−)-trans |
| 23 | H | 1 | Q | 2 | CH₃ | 2,4-Difluorbenzyl | |
| 24 | H | 1 | Q | 2 | CH₃ | 1-Methyl-pyridinium-2yl | |
| 25 | H | 1 | Q | 2 | CH₃ | Pyridin-4-yl-methyl | |
| 26 | H | 1 | Q | 2 | CH₃ | Pyridin-3-yl-methyl | |
| 27 | H | 1 | Q | 2 | CH(CH₃)₂ | 3,4-(Dimethoxy-phenyl)-ethyl | |
| 28 | H | 1 | Q | 1 | CH₃ | 2-OH-cyclohexyl | Racemic |
| 29 | H | 1 | Q | 2 | CH₃ | 2-OH-cyclohexyl | racemic |
| 30 | H | 1 | Q | 2 | CH₃ | 2-OH-cyclohexyl | trans-diastereomer-1 |
| 31 | H | 1 | Q | 2 | CH₃ | 2-OH-cyclohexyl | trans-diastereomer-2 |
| 32 | H | 1 | Q | 3 | CH₃ | 2-OH-cyclohexyl | racemic |
| 33 | H | 1 | Q | 4 | CH₃ | 2-OH-cyclohexyl | racemic |
| 34 | H | 1 | Q | 5 | CH₃ | 2-OH-cyclohexyl | racemic |
| 35 | H | 1 | Q | 2 | CH₃ | 4-Hydroxy-(1-tert.butoxypiperidin)-4-ylmethyl | |
| 36 | H | 1 | Q | 1 | CH₃ | 4-Hydroxy-piperidin-4-ylmethyl | |
| 37 | H | 1 | Q | 2 | CH₃ | 4-Hydroxy-piperidin-4-ylmethyl | |
| 38 | H | 1 | Q | 3 | CH₃ | 4-Hydroxy-piperidin-4-ylmethyl | |
| 39 | H | 1 | Q | 4 | CH₃ | 4-Hydroxy-piperidin-4-yl methyl | |
| 40 | H | 1 | Q | 2 | CH₃ | 4-Hydroxy-(1-naphthalen-2-ylmethyl)-piperidine-4-ylmethyl | |
| 41 | H | 1 | Q | 2 | CH₃ | 4-Hydroxy-1-isopropyl-piperidine-4-yl methyl | |
| 42 | H | 1 | Q | 2 | CH₃ | 4-Hydroxy-(1-(3-methoxybenzyl)-piperidine-4-ylmethyl | |
| 43 | H | 1 | Q | 2 | CH₃ | (4-Hydroxy-4-methyl-piperidin-1-yl)-acetic acid ethyl ester | |
| 44 | H | 1 | Q | 2 | CH₃ | (4-Hydroxy-4-methyl-piperidin-1-yl)-acetic acid | |
| 45 | H | 1 | Q | 2 | CH₃ | 4-Methoxy-piperidin-4-ylmethyl | |
| 46 | H | 1 | Q | 2 | CH₃ | 4-Methyl-4-hydroxy-piperidine-1-carboxamidine | |
| 47 | H | 1 | Q | 2 | CH₃ | 1-Acetyl-4-hydroxy-piperidin-4-ylmethyl | |
| 48 | H | 1 | Q | 2 | CH₃ | (1-Dimethylcarbamoyl-4-hydroxy-piperidin-4-yl) | |
| 49 | H | 1 | Q | 1 | CH₃ | 2,3-Dihydroxy-1-thiophen-3-yl-propyl | racemic |
| 50 | H | 1 | Q | 1 | CH₃ | 2,3,4,5-Tetrahydroxy-1-thiophen-3-yl-pentyl | L-arabinose |
| 51 | H | 1 | Q | 1 | CH₃ | 1-Furan-2-yl-2,3-dihydroxy-propyl | racemic |
| 52 | H | 1 | Q | 2 | CH₃ | 1-Furan-2-yl-2,3,4,5-tetrahydroxy-pentyl | D-xylose |
| 53 | H | 1 | Q | 1 | CH₃ | 1-Furan-2-yl-2,3,4,5-tetrahydroxy-pentyl | D-xylose |
| 54 | H | 1 | Q | 1 | CH₃ | 1-Furan-2-yl-2,3,4,5-tetrahydroxy-pentyl | L-xylose |
| 55 | H | 1 | Q | 1 | CH₃ | 1-Furan-2-yl-2,3,4,5,6-pentahydroxy-hexyl | D-glucose |
| 56 | H | 1 | Q | 1 | CH₃ | 2,3,4,5,6-Pentahydroxy-1-thiophen-3-yl-hexyl | D-glucose |
| 57 | H | 1 | Q | 1 | CH₃ | (2,3,4,5-tetrahydroxy-1-thiophen-3-yl-pentyl | L-xylose |
| 58 | H | 1 | Q | 1 | CH₃ | (2,3,4,5-tetrahydroxy-1-thiophen-2-yl-pentyl | D-xylose |
| 59 | H | 1 | Q | 2 | CH₃ | (2,3,4,5-tetrahydroxy-1-thiophen-2-yl-pentyl | D-xylose |
| 60 | H | 1 | Q | 2 | CH₃ | 3-[3-(4-hydroxy-4-phenyl-piperidin-1-yl | racemic |
| 61 | H | 1 | Q | 1 | CH₃ | 3-{2-[4-(4-Chloro-3-trifluoromethyl-phenyl)-4-hydroxy-piperidin | |
| 62 | H | 1 | Q | 2 | | 4-Phenyl-3,6-dihydro-2H-pyridin-1-yl) | |
| 63 | H | 1 | Q | 2 | | 4-(3-Chloro-phenyl)-piperazin-1-yl | |
| 64 | H | 1 | Q | 2 | | 4-(Phenyl)-piperazin-1-yl | |
| 65 | H | 1 | Q | 2 | | 4-(3-Fluorophenyl)-piperazin-1-yl | |
| 66 | H | 1 | Q | 2 | | 3-Hydroxymethyl-piperidin-1-yl | |
| 67 | H | 1 | Q | 2 | | 4-carboxylic acid amide piperidine-1yl | |
| 68 | H | 1 | (2)* | — | — | | |
| 69 | H | 1 | (3)* | — | — | | |
| 70 | H | 1 | (4)* | — | — | | |
| 71 | H | 1 | Q | 1 | CH₃ | 3-(4-Ethyl-piperazin-1-yl)-2-hydroxy-propyl | racemic |

-continued

| Ex. | R₁ | m | R₂ | n | R₃ | R₄ | stereochemistry |
|---|---|---|---|---|---|---|---|
| 72 | H | 1 | Q | 1 | CH₃ | 4-((4-Chloro-phenyl)-piperazin-1-yl)-2-hydroxy-propyl | racemic |
| 73 | H | 1 | Q | 1 | CH₃ | 2-Hydroxy-3-(4-pyridin-2-yl-piperazin-1-yl)-propyl | racemic |
| 74 | H | 1 | Q | 1 | CH₃ | 4-(Benzyl-piperazin-1-yl)-2-hydroxy-propyl | racemic |
| 75 | H | 1 | Q | 1 | CH₃ | 3-(4-Phenyl-piperazin-1-yl)-2-hydroxy-propyl | racemic |
| 76 | H | 1 | Q | 1 | CH₃ | 2-Hydroxy-3-(4-isopropyl-piperazin-1-yl)-propyl | racemic |
| 77 | H | 1 | Q | 2 | CH₃ | 3-(4-Ethyi-piperazin-1-yl)-2-hydroxy-propyl | racemic |
| 78 | H | 1 | Q | 2 | CH₃ | 4-((4-Chloro-phenyl)-piperazin-1-yl)-2-hydroxy-propyl | racemic |
| 79 | H | 1 | Q | 2 | CH₃ | 2-Hydroxy-3-(4-pyridin-2-yl-piperazin-1-yl)-propyl | racemic |
| 80 | H | 1 | Q | 2 | CH₃ | 4-(Benzyl-piperazin-1-yl)-2-hydroxy-propyl | racemic |
| 81 | H | 1 | Q | 2 | CH₃ | 3-(4-Phenyl-piperazin-1-yl)-2-hydroxy-propyl | racemic |
| 82 | H | 1 | Q | 2 | CH₃ | 2-Hydroxy-3-(4-isopropyl-piperazin-1-yl)-propyl | racemic |
| 83 | H | 1 | Q | 2 | CH₃ | Pyridin-2yl | |
| 84 | H | 1 | Q | 2 | H | Benzyl | |
| 85 | H | 1 | (5)* | — | — | — | |
| 86 | H | 1 | (6)* | — | — | — | |
| 87 | H | 1 | (7)* | — | — | — | |
| 88 | H | 1 | Q | 1 | CH₃ | 2-Cyclohexyl-2-hydroxy-acetyl | |
| 89 | H | 1 | Q | 1 | CH₃ | 2-Benzyl-2-hydroxy-acetyl | |
| 90 | H | 1 | Q | 1 | CH₃ | 3,4,5-Trimethoxybenzoyl | |
| 91 | H | 1 | Q | 2 | CH₃ | 2,3,4,5,6-Pentahydroxy-hexyl | (+)-D-Glucosamine |
| 92 | H | 1 | Q | 2 | CH₃ | 2,3-Dihydroxy-propyl | racemic |
| 93 | H | 1 | Q | 2 | CH₃ | 2-Hydroxy-3-morpholin-4-yl-propyl | racemic |
| 94 | H | 1 | Q | 2 | CH₃ | 2-Hydroxy-3-isopropoxy-propyl | |
| 95 | H | 1 | Q | 1 | CH₃ | 2-Methoxy-acetyl | |
| 96 | H | 1 | Q | 1 | CH₃ | Benzo[1,3]dioxole-5-carboxyl | |
| 97 | H | 1 | Q | 1 | CH₃ | 3,5-Bis-trifluoromethyl-benzoyl | |
| 98 | H | 1 | Q | 1 | CH₃ | Benzoyl | |
| 99 | H | 1 | Q | 1 | CH₃ | 2-Bromobenzoyl | |
| 100 | H | 1 | Q | 1 | CH₃ | 2,3,4,5,6-Pentafluorobenzoyl | |
| 101 | H | 1 | Q | 1 | CH₃ | 2,4-Dichlorobenzoyl | |
| 102 | H | 1 | Q | 1 | CH₃ | 2-Methoxybenzoyl | |
| 103 | H | 1 | Q | 1 | CH₃ | 2-Trifluoromethyl-benzoyl | |
| 104 | H | 1 | Q | 1 | CH₃ | 2-Methylbenzoyl | |
| 105 | H | 1 | Q | 1 | CH₃ | 3-Fluorobenzoyl | |
| 106 | H | 1 | Q | 1 | CH₃ | 3-Chlorobenzoyl | |
| 107 | H | 1 | Q | 1 | CH₃ | 3,4-Dichlorobenzoyl | |
| 108 | H | 1 | Q | 1 | CH₃ | 3-Methoxybenzoyl | |
| 109 | H | 1 | Q | 1 | CH₃ | 4-Fluorobenzoyl | |
| 110 | H | 1 | Q | 1 | CH₃ | 4-Chlorobenzoyl | |
| 111 | H | 1 | Q | 1 | CH₃ | 4-Methoxybenzoyl | |
| 112 | H | 1 | Q | 1 | CH₃ | 4-Hexyloxybenzoyl | |
| 113 | H | 1 | Q | 1 | CH₃ | 4-Trifluoromethyl-benzoyl | |
| 114 | H | 1 | Q | 1 | CH₃ | 4-tert.-Butylbenzoyl | |
| 115 | H | 1 | Q | 1 | CH₃ | 4-Methylbenzoyl | |
| 116 | H | 1 | Q | 1 | CH₃ | N-oxalamic acid methyl ester | |
| 117 | H | 1 | Q | 1 | CH₃ | 2-Acetoxy-2-methyl-propionyl | |
| 118 | H | 1 | Q | 1 | CH₃ | 2,2-Dimethylpropionyl | |
| 119 | H | 1 | Q | 1 | CH₃ | 2-Acetoxy-2-phenylacetyl | racemic |
| 120 | H | 1 | Q | 1 | CH₃ | 2-Phenoxyacetyl | |
| 121 | H | 1 | Q | 1 | CH₃ | 2-Phenylacetyl | |
| 122 | H | 1 | Q | 1 | CH₃ | 2,6-Dimethoxybenzoyl | |
| 123 | H | 1 | Q | 1 | CH₃ | 3,5-Dichlorobenzoyl | |
| 124 | H | 1 | Q | 1 | CH₃ | 2,6-Difluorobenzoyl | |
| 125 | H | 1 | Q | 1 | CH₃ | 2,6-Dichlorobenzoyl | |
| 126 | H | 1 | Q | 1 | CH₃ | 3-Methylbenzoyl | |
| 127 | H | 1 | Q | 1 | CH₃ | 2-Ethyl-hexanoyl | racemic |
| 128 | H | 1 | Q | 1 | CH₃ | Cyclobutanecarboxyl | |
| 129 | H | 1 | Q | 1 | CH₃ | 3-Nitrobenzoyl | |
| 130 | H | 1 | Q | 1 | CH₃ | 3-Cyanobenzoyl | |
| 131 | H | 1 | Q | 1 | CH₃ | (3-Methoxy-phenyl)-acetyl | |
| 132 | H | 1 | Q | 1 | CH₃ | 2-Ethylsulfanyl-pyridine-3-carboxyl | |
| 133 | H | 1 | Q | 1 | CH₃ | 3,5-Difluorobenzoyl | |
| 134 | H | 1 | Q | 1 | CH₃ | 3,4-Difluorobenzoyl | |
| 135 | H | 1 | Q | 1 | CH₃ | 2,4-Difluorobenzoyl | |
| 136 | H | 1 | Q | 1 | CH₃ | 3-Methyl-but-2-enoyl | |
| 137 | H | 1 | Q | 1 | CH₃ | 3,3-Dimethylbutyryl | |

-continued

| Ex. | R₁ | m | R₂ | n | R₃ | R₄ | stereochemistry |
|---|---|---|---|---|---|---|---|
| 138 | H | 1 | Q | 1 | CH₃ | Propionyl | |
| 139 | H | 1 | Q | 1 | CH₃ | 2-Benzylacetyl | |
| 140 | H | 1 | Q | 1 | CH₃ | 2,2,2-Trichloroacetyl | |
| 141 | H | 1 | Q | 1 | CH₃ | 2,2-Dichloroacetyl | |
| 142 | H | 1 | Q | 1 | CH₃ | 2-Phenyl-cyclopropanecarboxyl | |
| 143 | H | 1 | Q | 1 | CH₃ | 3-Cyclopentylpropionyl | |
| 144 | H | 1 | Q | 1 | CH₃ | Cyclohexylcarboxyl | |
| 145 | H | 1 | Q | 1 | CH₃ | Furan-2yl-carboxyl | |
| 146 | H | 1 | Q | 1 | CH₃ | Thiophen-2yl-carboxyl | |
| 147 | H | 1 | Q | 1 | CH₃ | 9-Oxo-9H-fluorene-4-carboxyl | |
| 148 | H | 1 | Q | 1 | CH₃ | 2-Benzyloxyacetyl | |
| 149 | H | 1 | Q | 1 | CH₃ | 2-Acetoxyacetyl | |
| 150 | H | 1 | Q | 1 | CH₃ | Pyridin-4yl-carboxyl | |
| 151 | H | 1 | Q | 1 | CH₃ | 2,2-Diphenylacetyl | |
| 152 | H | 1 | Q | 1 | CH₃ | 3-Oxo-propionic acid methyl ester | |
| 153 | H | 1 | Q | 1 | CH₃ | 2-Chlorobutyryl | racemic |
| 154 | H | 1 | Q | 1 | CH₃ | 6-Chlorohexanoyl | |
| 155 | H | 1 | Q | 1 | CH₃ | 2-[2-(4-Chloro-phenyl)-cyclopentyl]-acetyl | |
| 156 | H | 1 | Q | 1 | CH₃ | 2-Phenoxybutyryl | racemic |
| 157 | H | 1 | Q | 1 | CH₃ | Benzo[b]thiophen-2-yl-carboxyl | |
| 158 | H | 1 | Q | 1 | CH₃ | 2-(Trifluormethoxy)-benzoyl | |
| 159 | H | 1 | Q | 1 | CH₃ | (5-Methyl-2-phenyl-2H-[1,2,3]triazol-4-yl)-carboxyl | |
| 160 | H | 1 | Q | 1 | CH₃ | 2,6-Dichloropyridin-4yl-carboxyl | |
| 161 | H | 1 | Q | 1 | CH₃ | 2-(Propylsulfanyl)pyridin-3yl-carboxyl | |
| 162 | H | 1 | Q | 1 | CH₃ | 2,3-Dichloropyridin-5yl-carboxyl | |
| 163 | H | 1 | Q | 1 | CH₃ | 3-(2-Chloro-6-fluoro-phenyl)-5-methyl-isoxazole-4-carboxyl | |
| 164 | H | 1 | Q | 1 | CH₃ | 2,4,5-Trifluorobenzoyl | |
| 165 | H | 1 | Q | 1 | CH₃ | 3,3,3-Trifluoro-2-methoxy-2-phenyl-propionyl | |
| 166 | H | 1 | Q | 1 | CH₃ | 2-p-Tolylsulfanyl-pyridin-3-yl-carboxyl | |
| 167 | H | 1 | Q | 1 | CH₃ | 2-(4-Chloro-phenoxy)-pyridin-3-yl-carboxyl | |
| 168 | H | 1 | Q | 1 | CH₃ | 2-Chlor-3-methoxy-thiophen-4yl-carboxy | |
| 169 | H | 1 | Q | 1 | CH₃ | 1-Phenyl-5-trifluoromethyl-1H-pyrazole-4-carboxyl | |
| 170 | H | 1 | Q | 1 | CH₃ | Adamantane-1-carboxyl | |
| 171 | H | 1 | Q | 1 | CH₃ | 3-(3-Trifluoromethyl-phenyl)-propenoyl | E-isomer |
| 172 | H | 1 | Q | 1 | CH₃ | 2-tert-Butyl-5-methyl-2H-pyrazole-3-carboxyl | |
| 173 | H | 1 | Q | 1 | CH₃ | 5-tert-Butyl-2-methyl-2H-pyrazole-3-carboxyl | |
| 174 | H | 1 | Q | 1 | CH₃ | 2-Chloro-6-methoxy-pyridin-4yl-carboxyl | |
| 175 | H | 1 | Q | 1 | CH₃ | (2-p-Chlorophenoxy)-2-methyl-propionyl | |
| 176 | H | 1 | Q | 1 | CH₃ | 4R,7,7-Trimethyl-3-oxo-2-oxa-bicyclo[2.2.1]heptane-1-carboxyl | |
| 177 | H | 1 | Q | 1 | CH₃ | 3-Phenyl-2S-(toluene-4-sulfonylamino)-propionyl | |
| 178 | H | 1 | Q | 1 | CH₃ | 2,3-Dihydroxy-propyl | racemic |
| 179 | H | 1 | Q | 1 | CH₃ | 2-Hydroxy-2-phenyl-ethyl | racemic |
| 180 | H | 1 | Q | 1 | CH₃ | 2-hydroxy-propyl | racemic |
| 181 | H | 1 | Q | 1 | CH₃ | (3-Fluoro-2-hydroxy-propyl) | racemic |
| 182 | H | 1 | Q | 1 | CH₃ | 4-(Chloro-phenoxy)-2-hydroxy-propyl | racemic |
| 183 | H | 1 | Q | 1 | CH₃ | 3-(4-Methoxy-phenoxy)-2-hydroxy-propyl | racemic |
| 184 | H | 1 | Q | 1 | CH₃ | 3-(4-tert.-Butyl-phenoxy)-2-hydroxy-propyl | racemic |
| 185 | H | 1 | Q | 1 | CH₃ | 3-(iso-Propoxy)-2-hydroxy-propyl | racemic |
| 186 | H | 1 | Q | 1 | CH₃ | 3-(2-Ethyl-hexyloxy)-2-hydroxy-propyl | racemic |
| 187 | H | 1 | Q | 1 | CH₃ | 3-Allyloxy-2-hydroxy-propyl | racemic |
| 188 | H | 1 | Q | 1 | CH₃ | 3-Butoxy-2-hydroxy-propyl | racemic |
| 189 | H | 1 | Q | 1 | CH₃ | 2-Hydroxy-but-3-enyl | racemic |
| 190 | H | 1 | Q | 1 | CH₃ | 2-Hydroxy-but-4-yl | racemic |
| 191 | H | 1 | Q | 1 | CH₃ | 2-Hydroxy-oct-7-en-1yl | racemic |
| 192 | H | 1 | Q | 1 | CH₃ | 2-Hydroxy-oct-1yl | racemic |
| 193 | H | 1 | Q | 1 | CH₃ | 3-(1,3-Dioxo-1,3-dihydro-isoindol-2-yl)-2-hydroxy-propyl | racemic |
| 194 | H | 1 | Q | 1 | CH₃ | 3-tert.-Butoxy-2-hydroxy-propyl | racemic |
| 195 | H | 1 | Q | 1 | CH₃ | 2-Hydroxy-hex-5-enyl | racemic |
| 196 | H | 1 | Q | 1 | CH₃ | 2R-Hydroxy-3S-(4-methoxy-phenyl)-3yl-propionic acid methyl ester | |
| 197 | H | 1 | Q | 1 | CH₃ | 3-(Furan-2-ylmethoxy)-2-hydroxy-propyl | racemic |
| 198 | H | 1 | Q | 1 | CH₃ | 1-Trifluoromethyl-ethan-2yl-1ol | racemic |
| 199 | H | 1 | Q | 1 | CH₃ | 2-Hydroxy-3-(1,1,2,2-tetrafluoro-ethoxy)-propyl | racemic |
| 200 | H | 1 | Q | 1 | CH₃ | 2-Hydroxy-3-morpholin-4-yl-propyl | racemic |

-continued

| Ex. | R₁ | m | R₂ | n | R₃ | R₄ | stereochemistry |
|---|---|---|---|---|---|---|---|
| 201 | H | 1 | Q | 1 | CH₃ | 2-Hydroxy-dec-9-en-1yl | racemic |
| 202 | H | 1 | Q | 1 | CH₃ | 2-Hydroxy-3-phenyl-propyl | racemic |
| 203 | H | 1 | Q | 1 | CH₃ | 2-Hydroxy-2-methyl-but-3-enyl | racemic |
| 204 | H | 1 | Q | 1 | CH₃ | 2-Hydroxy-2-methyl-3yl-propionic acid methyl ester | racemic |
| 205 | H | 1 | Q | 1 | CH₃ | {3-[4-(4-Chloro-benzyl)-piperazin-1-yl]-2-hydroxy-propyl} | racemic |
| 206 | H | 1 | Q | 1 | CH₃ | 2-Hydroxy-hexyl | racemic |
| 207 | H | 1 | Q | 1 | CH₃ | 3-Hydroxy-3-phenyl-2yl-propionic acid ethyl ester | racemic |
| 208 | H | 1 | Q | 1 | CH₃ | 2(R),3-Dihydroxy-propyl | chiral |
| 209 | H | 1 | Q | 1 | CH₃ | 2-Hydroxy-dodecyl | racemic |
| 210 | H | 1 | Q | 1 | CH₃ | 2-Hydroxy-tetradecyl | racemic |
| 211 | H | 1 | Q | 1 | CH₃ | 2-Hydroxy-3-methoxy-propyl | racemic |
| 212 | H | 1 | Q | 1 | CH₃ | 2-Hydroxy-hexadecyl | racemic |
| 213 | H | 1 | Q | 1 | CH₃ | 2-Hydroxy-octadecyl | racemic |
| 214 | H | 1 | Q | 1 | CH₃ | 2-Hydroxy-cyclopentyl | racemic |
| 215 | H | 1 | Q | 1 | CH₃ | 3-Hydroxy-3-(4-methoxy-phenyl)-2yl-propionic acid methyl ester | racemic |
| 216 | H | 1 | Q | 1 | CH₃ | 2-Hydroxy-4-vinyl-cyclohexyl | racemic |
| 217 | H | 1 | Q | 1 | CH₃ | 2(S)-Hydroxy-1,2-diphenyl-ethyl | |
| 218 | H | 1 | Q | 1 | CH₃ | Biphenyl-4-ylmethyl | |
| 219 | H | 1 | Q | 1 | CH₃ | Naphthalen-2-ylmethyl | |
| 220 | H | 1 | Q | 1 | CH₃ | 3-Phenoxy-benzyl | |
| 221 | H | 1 | Q | 1 | CH₃ | Biphenyl-2-ylmethyl | |
| 222 | H | 1 | Q | 1 | CH₃ | Naphthalen-1-ylmethyl | |
| 223 | H | 1 | Q | 1 | CH₃ | (1H-Indol-3-yl)-ethyl | |
| 224 | H | 1 | Q | 1 | CH₃ | Pyridin-2-ylmethyl | |
| 225 | H | 1 | Q | 1 | CH₃ | 4-Trifluoromethyl-benzyl | |
| 226 | H | 1 | Q | 1 | CH₃ | Pyridin-3-ylmethyl | |
| 227 | H | 1 | Q | 1 | CH₃ | Cyclopropylmethyl | |
| 228 | H | 1 | Q | 1 | CH₃ | 6-Chloro-benzo[1,3]dioxol-5-ylmethyl | |
| 229 | H | 1 | Q | 1 | CH₃ | 4-Trifluoromethoxy-benzyl | |
| 230 | H | 1 | Q | 1 | CH₃ | 3-Oxo-3-phenyl-propyl | |
| 231 | H | 1 | Q | 1 | CH₃ | 2-Cyclohexyl-ethyl | |
| 232 | H | 1 | Q | 1 | CH₃ | 4-tert-Butyl-benzyl | |
| 233 | H | 1 | Q | 1 | CH₃ | 2-Phenoxy-ethyl | |
| 234 | H | 1 | Q | 1 | CH₃ | 4-Cyanobenzyl | |
| 235 | H | 1 | Q | 1 | CH₃ | 3,5-Dimethyl-isoxazol-4-ylmethyl | |
| 236 | H | 1 | Q | 1 | CH₃ | 2-Benzenesulfonyl-ethyl | |
| 237 | H | 1 | Q | 1 | CH₃ | Phenethyl | |
| 238 | H | 1 | Q | 1 | CH₃ | 2,4-Dioxo-1,4-dihydro-2H-quinazolin-3-yl-ethyl | |
| 239 | H | 1 | Q | 1 | CH₃ | 3-Fluorobenzyl | |
| 240 | H | 1 | Q | 1 | CH₃ | 4-Benzyloxybenzyl | |
| 241 | H | 1 | Q | 1 | CH₃ | 4-Chlorobenzyl | |
| 242 | H | 1 | Q | 1 | CH₃ | 3,4-Dibenzyloxybenzyl | |
| 243 | H | 1 | Q | 1 | CH₃ | 3-Trifluoromethoxybenzyl | |
| 244 | H | 1 | Q | 1 | CH₃ | Pentyl | |
| 245 | H | 1 | Q | 1 | CH₃ | 3-Phenyl-propyl | |
| 246 | H | 1 | Q | 1 | CH₃ | Propionamide-3yl | |
| 247 | H | 1 | Q | 1 | CH₃ | 2,6-Dioxo-1,2,3,6-tetrahydro-pyrimidin-4-yl | |
| 248 | H | 1 | Q | 1 | CH₃ | 3-Benzyloxy-propyl | |
| 249 | H | 1 | Q | 1 | CH₃ | 5-Chloro-thiophen-2-ylmethyl | |
| 250 | H | 1 | Q | 1 | CH₃ | propionic acid methyl ester-3yl | |
| 251 | H | 1 | Q | 1 | CH₃ | 3,5-Dimethylbenzyl | |
| 252 | H | 1 | Q | 1 | CH₃ | Cyanomethyl | |
| 253 | H | 1 | Q | 1 | CH₃ | 2-Fluorobenzyl | |
| 254 | H | 1 | Q | 1 | CH₃ | 3-Trifluoromethylbenzyl | |
| 255 | H | 1 | Q | 1 | CH₃ | 2-Cyanobenzyl | |
| 256 | H | 1 | Q | 1 | CH₃ | 3-Methyl-butyl | |
| 257 | H | 1 | Q | 1 | CH₃ | 2-Hydroxy-ethyl | |
| 258 | H | 1 | Q | 1 | CH₃ | 3-Chlorobenzyl | |
| 259 | H | 1 | Q | 1 | CH₃ | Anthracen-9-ylmethyl | |
| 260 | H | 1 | Q | 1 | CH₃ | 2-Methylbenzyl | |
| 261 | H | 1 | Q | 1 | CH₃ | 4-Bromobenzyl | |
| 262 | H | 1 | Q | 1 | CH₃ | 4-Methylbenzyl | |
| 263 | H | 1 | Q | 1 | CH₃ | 3-Cyanobenzyl | |
| 264 | H | 1 | Q | 1 | CH₃ | 2-Oxo-2-phenyl-ethyl | |
| 265 | H | 1 | Q | 1 | CH₃ | Acetamide-2yl | |
| 266 | H | 1 | Q | 1 | CH₃ | 2-(2,5-Dimethoxyphenyl)-2-oxo-ethyl | |
| 267 | H | 1 | Q | 1 | CH₃ | 2-Adamantan-1-yl-2-oxo-ethyl | |
| 268 | H | 1 | Q | 1 | CH₃ | 2-(3,4-Dihydro-2H-benzo[b][1,4]dioxepin-7-yl)-2-oxo-ethyl | |
| 269 | H | 1 | Q | 1 | CH₃ | 2-Oxo-1,2-diphenyl-ethyl | racemic |
| 270 | H | 1 | Q | 1 | CH₃ | Isobutyl | |
| 271 | H | 1 | Q | 1 | CH₃ | 4-Styryl-benzyl | E-isomer |

-continued

| Ex. | R₁ | m | R₂ | n | R₃ | R₄ | stereochemistry |
|---|---|---|---|---|---|---|---|
| 272 | H | 1 | Q | 1 | CH₃ | 3-Phenoxypropyl | |
| 273 | H | 1 | Q | 1 | CH₃ | 4-Fluorobenzyl | |
| 274 | H | 1 | Q | 1 | CH₃ | 3-Methoxybenzyl | |
| 275 | H | 1 | Q | 1 | CH₃ | Pyridin-4-ylmethyl | |
| 276 | H | 1 | Q | 1 | CH₃ | 2-Methoxybenzyl | |
| 277 | H | 1 | Q | 1 | CH₃ | N-(4-Phenoxy-phenyl)-formamidyl | |
| 278 | H | 1 | Q | 1 | CH₃ | N-Benzyl-formamidyl | |
| 279 | H | 1 | Q | 1 | CH₃ | N-Biphenyl-4-yl-formamidyl | |
| 280 | H | 1 | Q | 1 | CH₃ | N-Biphenyl-2-yl-formamidyl | |
| 281 | H | 1 | Q | 1 | CH₃ | N-(2-Methoxyphenyl)-formamidyl | |
| 282 | H | 1 | Q | 1 | CH₃ | N-(4-Fluorophenyl)-formamidyl | |
| 283 | H | 1 | Q | 1 | CH₃ | N-(4-Cyanophenyl)-formamidyl | |
| 284 | H | 1 | Q | 1 | CH₃ | N-(Adamantan-1-yl)-formamidyl | |
| 285 | H | 1 | Q | 1 | CH₃ | N-(2-Fluorophenyl)-formamidyl | |
| 286 | H | 1 | Q | 1 | CH₃ | N-(4-Methoxyphenyl)-formamidyl | |
| 287 | H | 1 | Q | 1 | CH₃ | N-(3-Cyanophenyl)-formamidyl | |
| 288 | H | 1 | Q | 1 | CH₃ | 3-(Formylamino)-benzoic acid ethyl ester | |
| 289 | H | 1 | Q | 1 | CH₃ | N-(2-Phenethyl)-formamidyl | |
| 290 | H | 1 | Q | 1 | CH₃ | N-(1-Naphthalen-1-yl-ethyl)-formamidyl | racemic |
| 291 | H | 1 | Q | 1 | CH₃ | N-(2,6-Dichlorophenyl)-formamidyl | |
| 292 | H | 1 | Q | 1 | CH₃ | N-(3-Chlorophenyl)-formamidyl | |
| 293 | H | 1 | Q | 1 | CH₃ | N-(4-Chlorophenyl)-formamidyl | |
| 294 | H | 1 | Q | 1 | CH₃ | N-(tert.-Butyl)-formamidyl | |
| 295 | H | 1 | Q | 1 | CH₃ | N-(1-Phenethyl)-formamidyl | R-isomer |
| 296 | H | 1 | Q | 1 | CH₃ | N-Butyl-formamidyl | |
| 297 | H | 1 | Q | 1 | CH₃ | N-(3,4,5-Trimethoxyphenyl)-formamidyl | |
| 298 | H | 1 | Q | 1 | CH₃ | N-(2,4-Dimethoxyphenyl)-formamidyl | |
| 299 | H | 1 | Q | 1 | CH₃ | N-Benzoyl-formamidyl | |
| 300 | H | 1 | Q | 1 | CH₃ | N-(iso-Propyl)-formamidyl | |
| 301 | H | 1 | Q | 1 | CH₃ | N-(4-Nitrophenyl)-formamidyl | |
| 302 | H | 1 | Q | 1 | CH₃ | N-(2-Methylsulfanyl-phenyl)-formamidyl | |
| 303 | H | 1 | Q | 1 | CH₃ | (Formylamino)-acetic acid ethyl ester | |
| 304 | H | 1 | Q | 1 | CH₃ | N-(4-Bromophenyl)-formamidyl | |
| 305 | H | 1 | Q | 1 | CH₃ | N-(4-Butylphenyl)-formamidyl | |
| 306 | H | 1 | Q | 1 | CH₃ | 2-Formylamino-3-phenyl-propionic acid methyl ester | S-isomer |
| 307 | H | 1 | Q | 1 | CH₃ | N-(2,5-Dimethoxyphenyl)-formamidyl | |
| 308 | H | 1 | Q | 1 | CH₃ | N-(2-Methylphenyl)-formamidyl | |
| 309 | H | 1 | Q | 1 | CH₃ | N-(2,6-Dimethylphenyl)-formamidyl | |
| 310 | H | 1 | Q | 1 | CH₃ | N-(3,4-Dichlorophenyl)-formamidyl | |
| 311 | H | 1 | Q | 1 | CH₃ | 4-(Formylamino)-benzoic acid ethyl ester | |
| 312 | H | 1 | Q | 1 | CH₃ | N-(3-Nitrophenyl)-formamidyl | |
| 313 | H | 1 | Q | 1 | CH₃ | N-(3,5-Di(trifluoromethyl)-phenyl)-formamidyl | |
| 314 | H | 1 | Q | 1 | CH₃ | N-(2,4,6-Trimethylphenyl)-formamidyl | |
| 315 | H | 1 | Q | 1 | CH₃ | 4-(Formylamino)-benzoic acid butyl ester | |
| 316 | H | 1 | Q | 1 | CH₃ | 3-(Formylamino)-propionic acid ethyl ester | |
| 317 | H | 1 | Q | 1 | CH₃ | N-(1,1,3,3-Tetramethyl-butyl)-formamidyl | |
| 318 | H | 1 | Q | 1 | CH₃ | N-(2,4-Difluorophenyl)-formamidyl | |
| 319 | H | 1 | Q | 1 | CH₃ | N-(2,4-Dichlorophenyl)-formamidyl | |
| 320 | H | 1 | Q | 1 | CH₃ | N-(3-Methylphenyl)-formamidyl | |
| 321 | H | 1 | Q | 1 | CH₃ | N-Allyl-formamidyl | |
| 322 | H | 1 | Q | 1 | CH₃ | 2-Formylamino-acetic acid butyl ester | |
| 323 | H | 1 | Q | 1 | CH₃ | 2-Formylamino-3-phenyl-propionic acid ethyl ester | racemic |
| 324 | H | 1 | Q | 1 | CH₃ | N-(2-Trifluoromethoxyphenyl)-formamidyl | |
| 325 | H | 1 | Q | 1 | CH₃ | N-Pentyl-formamidyl | |
| 326 | H | 1 | Q | 1 | CH₃ | 2-Formylamino-3-methyl-butyric acid methyl ester | S-isomer |
| 327 | H | 1 | Q | 1 | CH₃ | N-(2-Bromophenyl)-formamidyl | |
| 328 | H | 1 | Q | 1 | CH₃ | N-(2-Methoxyphenyl)-formamidyl | |
| 329 | H | 1 | Q | 1 | CH₃ | 2-(Formylamino)-benzoic acid ethyl ester | |
| 330 | H | 1 | Q | 1 | CH₃ | N-(4-Ethylphenyl)-formamidyl | |
| 331 | H | 1 | Q | 1 | CH₃ | N-(2,3-Dichlorophenyl)-formamidyl | |
| 332 | H | 1 | Q | 1 | CH₃ | N-(2,5-Dichlorophenyl)-formamidyl | |
| 333 | H | 1 | Q | 1 | CH₃ | N-(3-Bromophenyl)-formamidyl | |
| 334 | H | 1 | Q | 1 | CH₃ | N-(2,6-Di-(iso-propyl)-phenyl)-formamidyl | |
| 335 | H | 1 | Q | 1 | CH₃ | N-Formyl-carbamic acid ethyl ester | |
| 336 | H | 1 | Q | 1 | CH₃ | N-(2,4-Dimethylphenyl)-formamidyl | |
| 337 | H | 1 | Q | 1 | CH₃ | N-(5-Chloro-2-methoxyphenyl)-formamidyl | |
| 338 | H | 1 | Q | 1 | CH₃ | N-(4-Chloro-2-trifluoromethyl-phenyl)-formamidyl | |

-continued

| Ex. | $R_1$ | m | $R_2$ | n | $R_3$ | $R_4$ | stereochemistry |
|---|---|---|---|---|---|---|---|
| 339 | H | 1 | Q | 1 | $CH_3$ | N-(4-Chloro-3-trifluoromethyl-phenyl)-formamidyl | |
| 340 | H | 1 | Q | 1 | $CH_3$ | N-(4-Ethoxyphenyl)-formamidyl | |
| 341 | H | 1 | Q | 1 | $CH_3$ | N-(4-Chloro-2-nitro-phenyl)-formamidyl | |
| 342 | H | 1 | Q | 1 | $CH_3$ | N-(2,6-Diethylphenyl)-formamidyl | |
| 343 | H | 1 | Q | 1 | $CH_3$ | N-(6-Chloro-2-methyl-phenyl)-formamidyl | |
| 344 | H | 1 | Q | 1 | $CH_3$ | N-(4-Bromo-2,6-dimethyl-phenyl)-formamidyl | |
| 345 | H | 1 | Q | 1 | $CH_3$ | 6-Formylamino-hexanoic acid ethyl ester | |
| 346 | H | 1 | Q | 1 | $CH_3$ | 2-Formylamino-propionic acid ethyl ester | racemic |
| 347 | H | 1 | Q | 1 | $CH_3$ | N-(2,5-Dinitophenyl)-formamidyl | |
| 348 | H | 1 | Q | 1 | $CH_3$ | 4-Benzo[1,3]dioxol-5-ylmethyl-piperazine-1-carboxyl | |
| 349 | H | 1 | Q | 1 | $CH_3$ | 4-(2-Oxo-2,3-dihydro-benzoimidazol-1-yl)-piperidine-1-carboxyl | |
| 350 | H | 1 | Q | 1 | $CH_3$ | 3,4-Dihydro-1H-isoquinoline-2-carboxyl | |
| 351 | H | 1 | Q | 1 | $CH_3$ | 2,5-Dihydro-pyrrole-1-carboxyl | |
| 352 | H | 1 | Q | 1 | $CH_3$ | 4-Phenyl-piperazine-1-carboxyl | |
| 353 | H | 1 | Q | 1 | $CH_3$ | Morpholine-4-carboxyl | |
| 354 | H | 1 | Q | 1 | $CH_3$ | 4-Pyridin-2-yl-piperazine-1-carboxyl | |
| 355 | H | 1 | Q | 1 | $CH_3$ | N-Methyl-N-(2-pyridin-2-yl-ethyl)-formamidyl | |
| 356 | H | 1 | Q | 1 | $CH_3$ | Pyrrolidine-1-carboxyl | |
| 357 | H | 1 | Q | 1 | $CH_3$ | 1-Formyl-pyrrolidine-2-carboxylic acid benzyl ester | S-isomer (pyrrolidine) |
| 358 | H | 1 | Q | 1 | $CH_3$ | 4-(4-Fluoro-phenyl)-piperazine-1-carboxyl | |
| 359 | H | 1 | Q | 1 | $CH_3$ | 4-(2-Methoxy-phenyl)-piperazine-1-carboxyl | |
| 360 | H | 1 | Q | 1 | $CH_3$ | 4-(4-Chloro-phenyl)-4-hydroxy-piperidine-1-carboxyl | |
| 361 | H | 1 | Q | 1 | $CH_3$ | 4-(4-Trifluoromethyl-phenyl)-piperazine-1-carboxyl | |
| 362 | H | 1 | Q | 1 | $CH_3$ | 4-(4-Chloro-benzyl)-piperazine-1-carboxyl | |
| 363 | H | 1 | Q | 1 | $CH_3$ | Thiazolidine-3-carboxyl | |
| 364 | H | 1 | Q | 1 | $CH_3$ | 4-[2-(2-Hydroxy-ethoxy)-ethyl]-piperazine-1-carboxyl | |
| 365 | H | 1 | Q | 1 | $CH_3$ | N,N-Diethylformamidyl | |
| 366 | H | 1 | Q | 1 | $CH_3$ | 1,4-Dioxa-8-aza-spiro[4.5]decane-8-carboxyl | |
| 367 | H | 1 | Q | 1 | $CH_3$ | 1-Formyl-piperidine-4-carboxylic acid ethyl ester | |
| 368 | H | 1 | Q | 1 | $CH_3$ | 1,3,4,9-Tetrahydro-beta-carboline-2-carboxyl | |
| 369 | H | 1 | Q | 1 | $CH_3$ | 4-Hydroxy-4-phenyl-piperidine-1-carboxyl | |
| 370 | H | 1 | Q | 1 | $CH_3$ | N-Methyl-N-(naphthalen-1-ylmethyl)-formamidyl | |
| 371 | H | 1 | Q | 1 | $CH_3$ | 4-(4-Methoxy-phenyl)-piperazine-1-carboxyl | |
| 372 | H | 1 | Q | 1 | $CH_3$ | 2,3,5,6-Tetrahydro-[1,2']bipyrazinyl-4-carboxyl | |
| 373 | H | 1 | Q | 1 | $CH_3$ | 1-Formyl-piperidine-3-carboxylic acid amide | |
| 374 | H | 1 | Q | 1 | $CH_3$ | N-Benzyl-N-phenethyl-formamidyl | |
| 375 | H | 1 | Q | 1 | $CH_3$ | N,N-Bis-(2-methoxy-ethyl)-formamidyl | |
| 376 | H | 1 | Q | 1 | $CH_3$ | 4-(3-Trifluoromethyl-phenyl)-piperazine-1-carboxyl | |
| 377 | H | 1 | Q | 1 | $CH_3$ | 3-Hydroxy-pyrrolidine-1-carboxyl | racemic |
| 378 | H | 1 | Q | 1 | $CH_3$ | 2-Methoxymethyl-pyrrolidine-1-carboxyl | S-isomer |
| 379 | H | 1 | Q | 1 | $CH_3$ | 4-Oxo-1-phenyl-1,3,8-triaza-spiro[4.5]decane-8-carboxyl | |
| 380 | H | 1 | Q | 1 | $CH_3$ | 4-(2-Fluoro-phenyl)-piperazine-1-carboxyl | |
| 381 | .H | 1 | Q | 1 | $CH_3$ | 4-Pyridin-4-yl-piperazine-1-carboxyl | |
| 382 | H | 1 | Q | 1 | $CH_3$ | 4-Hydroxy-piperidine-1-carboxyl | racemic |
| 383 | H | 1 | Q | 1 | $CH_3$ | N-Ethyl-N-(2-hydroxy-ethyl)-formamidyl | |
| 384 | H | 1 | Q | 1 | $CH_3$ | 3-Hydroxy-piperidine-1-carboxyl | racemic |
| 385 | H | 1 | Q | 1 | $CH_3$ | N-Methyl-N-propyl-formamidyl | |
| 386 | H | 1 | Q | 1 | $CH_3$ | 2-(Formyl-methyl-amino)-benzoic acid methyl ester | |
| 387 | H | 1 | Q | 1 | $CH_3$ | N-(2-Dimethylamino-ethyl)-N-methyl-formamidyl | |
| 388 | H | 1 | Q | 1 | $CH_3$ | N-Methyl-N-phenethyl-formamidyl | |
| 389 | H | 1 | Q | 1 | $CH_3$ | N-Allyl-N-methyl-formamidyl | |

-continued

| Ex. | R₁ | m | R₂ | n | R₃ | R₄ | stereochemistry |
|---|---|---|---|---|---|---|---|
| 390 | H | 1 | Q | 1 | CH₃ | 3,6-Dihydro-2H-pyridine-1-carboxyl | |
| 391 | H | 1 | Q | 1 | CH₃ | Pyrrolidine-1-carboxyl-2-carboxylic acid amide | R-isomer |
| 392 | H | 1 | Q | 1 | CH₃ | 4-(2-Methoxy-phenyl)-piperazine-1-carboxyl | |
| 393 | H | 1 | Q | 1 | CH₃ | N-Methyl-N-ethyl-formamidyl | |
| 394 | H | 1 | Q | 1 | CH₃ | 4-Cyclohexyl-piperazine-1-carboxyl | |
| 395 | H | 1 | Q | 1 | CH₃ | N,N-Dimethyl-formamidyl | |
| 396 | H | 1 | Q | 1 | CH₃ | 4-Pyrrolidin-1-yl-piperidine-1-carboxyl | |
| 397 | H | 1 | Q | 1 | CH₃ | N,N-Diphenyl-formamidyl | |
| 398 | H | 1 | Q | 1 | CH₃ | N-Methyl-N-phenyl-formamidyl | |
| 399 | H | 1 | Q | 1 | CH₃ | Formic acid phenyl ester | |
| 400 | H | 1 | Q | 1 | CH₃ | Formic acid isobutyl ester | |
| 401 | H | 1 | Q | 1 | CH₃ | Formic acid methyl ester | |
| 402 | H | 1 | Q | 1 | CH₃ | Formic acid allyl ester | |
| 403 | H | 1 | Q | 1 | CH₃ | Formic acid (4-methoxyphenyl) ester | |
| 404 | H | 1 | Q | 1 | CH₃ | Formic acid (2-methoxyethyl) ester | |
| 405 | H | 1 | Q | 1 | CH₃ | Formic acid (2-ethylhexyl) ester | racemic |
| 406 | H | 1 | Q | 1 | CH₃ | Formic acid propyl ester | |
| 407 | H | 1 | Q | 1 | CH₃ | Formic acid (4-fluorophenyl) ester | |
| 408 | H | 1 | Q | 1 | CH₃ | Formic acid (4-chlorophenyl) ester | |
| 409 | H | 1 | Q | 1 | CH₃ | Formic acid (4-nitrobenzyl) ester | |
| 410 | H | 1 | Q | 1 | CH₃ | Formic acid 2-isopropyl-5-methyl-cyclohexyl ester | (−)-Menthol |
| 411 | H | 1 | Q | 1 | CH₃ | Formic acid (4-methylphenyl) ester | |
| 412 | H | 1 | Q | 1 | CH₃ | Formic acid butyl ester | |
| 413 | H | 1 | Q | 1 | CH₃ | Formic acid but-3-enyl ester | |
| 414 | H | 1 | Q | 1 | CH₃ | Formic acid ethyl ester | |
| 415 | H | 1 | Q | 1 | CH₃ | Formic acid prop-2-ynyl ester | |
| 416 | H | 1 | Q | 1 | CH₃ | Formic acid 2,2,2-trichloro-1,1-dimethyl-ethyl ester | |
| 417 | H | 1 | Q | 1 | CH₃ | Formic acid (2-nitrophenyl) ester | |
| 418 | H | 1 | Q | 1 | CH₃ | Formic acid 2,2,2-trichloro-ethyl ester | |
| 419 | H | 1 | Q | 1 | CH₃ | Formic acid 2-isopropyl-5-methyl-cyclohexyl ester | (+)-Menthol |
| 420 | H | 1 | Q | 1 | CH₃ | Naphthalene-1-sulfonyl | |
| 421 | H | 1 | Q | 1 | CH₃ | Thiophene-2-sulfonyl | |
| 422 | H | 1 | Q | 1 | CH₃ | Quinoline-8-sulfonyl | |
| 423 | H | 1 | Q | 1 | CH₃ | Biphenyl-4-sulfonyl | |
| 424 | H | 1 | Q | 1 | CH₃ | Naphthalene-2-sulfonyl | |
| 425 | H | 1 | Q | 1 | CH₃ | Benzenesulfonyl | |
| 426 | H | 1 | Q | 1 | CH₃ | 4-Fluoro-benzenesulfonyl | |
| 427 | H | 1 | Q | 1 | CH₃ | 4-iso-Propyl-benzenesulfonyl | |
| 428 | H | 1 | Q | 1 | CH₃ | 4-Methanesulfonyl-benzenesulfonyl | |
| 429 | H | 1 | Q | 1 | CH₃ | 4-Methoxy-benzenesulfonyl | |
| 430 | H | 1 | Q | 1 | CH₃ | 2-Fluoro-benzenesulfonyl | |
| 431 | H | 1 | Q | 1 | CH₃ | 3,4-Dimethoxy-benzenesulfonyl | |
| 432 | H | 1 | Q | 1 | CH₃ | 3-Trifluoromethyl-benzenesulfonyl | |
| 433 | H | 1 | Q | 1 | CH₃ | 2-Cyano-benzenesulfonyl | |
| 434 | H | 1 | Q | 1 | CH₃ | 4-tert-Butyl-benzenesulfonyl | |
| 435 | H | 1 | Q | 1 | CH₃ | 5-Dimethylamino-naphthalene-1-sulfonyl | |
| 436 | H | 1 | Q | 1 | CH₃ | 4-Chloro-benzenesulfonyl | |
| 437 | H | 1 | Q | 1 | CH₃ | 4-Acetylamino-benzenesulfonyl | |
| 438 | H | 1 | Q | 1 | CH₃ | 5-Chloro-thiophene-2-sulfonyl | |
| 439 | H | 1 | Q | 1 | CH₃ | 4-Trifluoromethyl-benzenesulfonyl | |
| 440 | H | 1 | Q | 1 | CH₃ | Benzo[1,2,5]thiadiazole-4-sulfonyl | |
| 441 | H | 1 | Q | 1 | CH₃ | 2-Acetylamino-4-methyl-thiazole-5-sulfonyl | |
| 442 | H | 1 | Q | 1 | CH₃ | 4-Benzenesulfonyl-thiophene-2-sulfonyl | |
| 443 | H | 1 | Q | 1 | CH₃ | 2,4,6-Trimethyl-benzenesulfonyl | |
| 444 | H | 1 | Q | 1 | CH₃ | 2-Phenyl-ethenesulfonyl | |
| 445 | H | 1 | Q | 1 | CH₃ | 2,5-Dimethoxy-benzenesulfonyl | |
| 446 | H | 1 | Q | 1 | CH₃ | 3,4-Dichloro-benzenesulfonyl | |
| 447 | H | 1 | Q | 1 | CH₃ | 2,4-Difluoro-benzenesulfonyl | |
| 448 | H | 1 | Q | 1 | CH₃ | 4-Methyl-benzenesulfonyl | |
| 449 | H | 1 | Q | 1 | CH₃ | 2-Chloro-benzenesulfonyl | |
| 450 | H | 1 | Q | 1 | CH₃ | 3-Chloro-benzenesulfonyl | |
| 451 | H | 1 | Q | 1 | CH₃ | 2,6-Dichloro-benzenesulfonyl | |
| 452 | H | 1 | Q | 1 | CH₃ | 2,5-Dichloro-benzenesulfonyl | |
| 453 | H | 1 | Q | 1 | CH₃ | 3-Nitro-benzenesulfonyl | |
| 454 | H | 1 | Q | 1 | CH₃ | Methanesulfonyl | |
| 455 | H | 1 | Q | 1 | CH₃ | 4-Trifluoromethoxy-benzenesulfonyl | |
| 456 | H | 1 | Q | 1 | CH₃ | 3-Methyl-benzenesulfonyl | |
| 457 | H | 1 | Q | 1 | CH₃ | 4-Nitro-benzenesulfonyl | |
| 458 | H | 1 | Q | 1 | CH₃ | 4-Propyl-benzenesulfonyl | |
| 459 | H | 1 | Q | 1 | CH₃ | 2-Trifluoromethyl-benzenesulfonyl | |
| 460 | H | 1 | Q | 1 | CH₃ | 4-Bromo-benzenesulfonyl | |

| Ex. | R₁ | m | R₂ | n | R₃ | R₄ | stereochemistry |
|---|---|---|---|---|---|---|---|
| 461 | H | 1 | Q | 1 | CH₃ | 5-Benzenesulfonyl-thiophene-2-sulfonyl | |
| 462 | H | 1 | Q | 1 | CH₃ | 2-Methanesulfonyl-benzenesulfonyl | |
| 463 | H | 1 | Q | 1 | CH₃ | 2-Bromo-benzenesulfonyl | |
| 464 | H | 1 | Q | 1 | CH₃ | 4-Sulfamoyl-benzoic acid | |
| 465 | H | 1 | Q | 1 | CH₃ | 2-Nitro-benzenesulfonyl | |
| 466 | H | 1 | Q | 1 | CH₃ | 3,5-Dichloro-benzenesulfonyl | |
| 467 | H | 1 | Q | 1 | CH₃ | 4,5-Dichloro-thiophene-2-sulfonyl | |
| 468 | H | 1 | Q | 1 | CH₃ | 3-Bromo-benzenesulfonyl | |
| 469 | H | 1 | Q | 1 | CH₃ | 4-Butoxy-benzenesulfonyl | |
| 470 | H | 1 | Q | 1 | CH₃ | 4-Methyl-benzenesulfonyl | |
| 471 | H | 1 | Q | 1 | CH₃ | 2,4-Dichloro-thiophene-2-sulfonyl | |
| 472 | H | 1 | Q | 1 | CH₃ | 4-(1,1-Dimethyl-propyl-benzenesulfonyl | |
| 473 | H | 1 | Q | 1 | CH₃ | 2-Methyl-5-nitro-benzenesulfonyl | |
| 474 | H | 1 | Q | 1 | CH₃ | 3,5-Bis-trifluoromethyl-benzenesulfonyl | |
| 475 | H | 1 | Q | 1 | CH₃ | 4-Ethyl-benzenesulfonyl | |
| 476 | H | 1 | Q | 1 | CH₃ | 2,5-Dichloro-thiophene-3-sulfonyl | |
| 477 | H | 1 | Q | 1 | CH₃ | 5-Bromo-2-methoxy-benzenesulfonyl | |
| 478 | H | 1 | Q | 1 | CH₃ | 2-Chloro-4-fluoro-benzenesulfonyl | |
| 479 | H | 1 | Q | 1 | CH₃ | 5-Fluoro-2-methyl-benzenesulfonyl | |
| 480 | H | 1 | Q | 1 | CH₃ | 4-(4-Dimethylamino-phenylazo)-benzenesulfonyl | |
| 481 | H | 1 | Q | 1 | CH₃ | 2,4-Dinitro-benzenesulfonyl | |
| 482 | H | 1 | Q | 1 | CH₃ | 4,5-Dibromo-thiophene-2-sulfonyl | |
| 483 | H | 1 | Q | 1 | CH₃ | 4-Bromo-2,5-dichloro-thiophene-3-sulfonyl | |
| 484 | H | 1 | Q | 1 | CH₃ | 2,3-Dichloro-benzenesulfonyl | |
| 485 | H | 1 | Q | 1 | CH₃ | 2,4,6-Trichloro-benzenesulfonyl | |
| 486 | H | 1 | Q | 1 | CH₃ | 2-Chloro-6-methyl-benzenesulfonyl | |
| 487 | H | 1 | Q | 1 | CH₃ | 2,4,6-Triisopropyl-benzenesulfonyl | |
| 488 | H | 1 | Q | 1 | CH₃ | 5-Chloro-3-methyl-benzo[b]thiophene-2-sulfonyl | |

(1)* R₂ = (2-methoxy-ethoxymethyl)
(2)* R₂ = 4-Hydroxy-piperidin-4-ylmethyl
(3)* R₂ = 1-Benzyl-piperidin-4-ylmethyl
(4)* R₂ = Piperidin-4-ylmethyl
(5)* R₂ = 4-benzyl-morpholin-2-ylmethyl
(6)* R₂ = acetyl
(7)* R₂ = 3-aminobenzyl Analytical data of the examples given in the table above, are given in the table below. Details of the analytical methods listed in this table, viz. "BASIS", "STANDARD", "CURVE 4", "AMAP 2" and "AMAP 3" are explained below.

| Ex | Mol Formula | Mol Wgt | Melting pt. | (MH⁺) | Ret. Time | Method |
|---|---|---|---|---|---|---|
| 1 | $C_{24}H_{35}N_3O$ | 381.560 | — | 382 | 7.630 | BASIS |
| 2 | $C_{24}H_{35}N_3O$ | 381.560 | 187–189° C. | — | | |
| 3 | $C_{24}H_{35}N_3O$ | 381.560 | 180.9° C. | — | — | — |
| 4 | $C_{24}H_{35}N_3O$ | 381.560 | 187.9° C. | — | — | — |
| 5 | $C_{24}H_{34}FN_3O$ | 399.551 | 189–191° C. | — | — | — |
| 6 | $C_{25}H_{37}N_3O_2$ | 411.586 | 156–157° C. | — | — | — |
| 7 | $C_{24}H_{34}Cl_1N_3O$ | 416.006 | 144–145° C. | — | — | — |
| 8 | $C_{25}H_{37}N_3O_2$ | 411.586 | 152–153° C. | — | — | — |
| 9 | $C_{24}H_{34}FN_3O$ | 399.551 | 198–199° C. | — | — | — |
| 10 | $C_{25}H_{34}F_3N_3O$ | 449.558 | 174–176° C. | — | — | — |
| 11 | $C_{28}H_{43}N_3O_3$ | 469.666 | — | 470 | 3.990 | CURVE 4 |
| 12 | $C_{27}H_{42}N_4O$ | 438.656 | | 439 | 6.500 | BASIS |
| 13 | $C_{28}H_{44}N_4O$ | 452.683 | | 453 | 3.340 | CURVE 4 |
| 14 | $C_{29}H_{46}N_4O$ | 466.709 | | 467 | 6.870 | BASIS |
| 15 | $C_{30}H_{48}N_4O$ | 480.736 | | 481 | 7.030 | BASIS |
| 16 | $C_{31}H_{50}N_4O$ | 494.763 | | 495 | 7.130 | BASIS |
| 17 | $C_{34}H_{48}N_4O$ | 528.780 | | 529 | 1.195 | AMAP 2 |
| 18 | $C_{33}H_{53}N_5O_2$ | 551.815 | | 552 | 1.135 | AMAP 2 |
| 19 | $C_{35}H_{48}N_4O_3$ | 572.789 | | 573 | 3.580 | CURVE 4 |
| 20 | $C_{34}H_{49}N_5O_3S$ | 607.859 | | 608 | 3.430 | STANDARD |
| 21 | $C_{29}H_{46}N_4O$ | 466.709 | | 467 | 6.730 | BASIS |
| 22 | $C_{29}H_{46}N_4O$ | 466.709 | | 467 | 3.310 | CURVE 4 |
| 23 | $C_{35}H_{48}F_2N_4O$ | 578.787 | | 579 | 9.530 | BASIS |

-continued

| Ex | Mol Formula | Mol Wgt | Melting pt. | (MH⁺) | Ret. Time | Method |
|---|---|---|---|---|---|---|
| 24 | C34 H50 N5 O | 544.803 | | 545 | 3.450 | CURVE 4 |
| 25 | C34 H49 N5 O | 543.795 | | 544 | 3.940 | CURVE 4 |
| 26 | C34 H49 N5 O | 543.795 | | 545 | 3.770 | STANDARD |
| 27 | C40 H60 N4 O3 | 644.939 | | 645 | 3.980 | CURVE 4 |
| 28 | C35 H54 N4 O3 | 578.837 | | 579 | 5.350 | STANDARD |
| 29 | C34 H54 N4 O2 | 550.827 | | 551 | 7.000 | BASIS |
| 30 | C34 H54 N4 O2 | 550.827 | | 551 | 7.000 | BASIS |
| 31 | C34 H54 N4 O2 | 550.827 | | 551 | 3.340 | CURVE 4 |
| 32 | C36 H58 N4 O2 | 564.853 | | 565 | 3.350 | CURVE 4 |
| 33 | C35 H56 N4 O2 | 578.889 | | 579 | 3.390 | CURVE 4 |
| 34 | C37 H60 N4 O2 | 592.907 | | 593 | 3.460 | CURVE 4 |
| 35 | C39 H63 N5 O4 | 665.958 | | 666 | 3.690 | CURVE 4 |
| 36 | C33 H53 N5 O2 | 551.815 | | 552 | 4.700 | CURVE 4 |
| 37 | C34 H55 N5 O2 | 565.841 | | 566 | 3.090 | CURVE 4 |
| 38 | C35 H57 N5 O2 | 579.868 | | 580 | 3.140 | CURVE 4 |
| 39 | C36 H59 N5 O2 | 593.895 | | 594 | 3.100 | CURVE 4 |
| 40 | C45 H63 N5 O2 | 706.026 | | 706 | 3.810 | CURVE 4 |
| 41 | C37 H61 N5 O2 | 607.922 | | 608 | 4.460 | STANDARD |
| 42 | C42 H63 N5 O3 | 685.992 | | 686 | 3.540 | CURVE 4 |
| 43 | C38 H61 N5 O4 | 651.931 | | 652 | 3.480 | CURVE 4 |
| 44 | C36 H57 N5 O4 | 623.877 | | 624 | 3.150 | CURVE 4 |
| 45 | C35 H57 N5 O2 | 579.868 | | 580 | 4.480 | STANDARD |
| 46 | C35 H57 N7 O2 | 607.882 | | 608 | 3.190 | CURVE 4 |
| 47 | C36 H57 N5 O3 | 607.878 | | 608 | 3.630 | CURVE 4 |
| 48 | C37 H60 N6 O3 | 636.920 | | 637 | 3.330 | CURVE 4 |
| 49 | C34 H50 N4 O3 S | 594.860 | | 595 | 8.230 | BASIS |
| 50 | C36 H54 N4 O5 S | 654.912 | | 655 | 3.690 | CURVE 4 |
| 51 | C34 H50 N4 O4 | 578.793 | | 579 | 8.200 | BASIS |
| 52 | C37 H56 N4 O6 | 652.871 | | 653 | 7.870 | BASIS |
| 53 | C36 H54 N4 O6 | 638.845 | | 639 | 7.870 | BASIS |
| 54 | C36 H54 N4 O6 | 638.845 | | 639 | 7.830 | BASIS |
| 55 | C37 H56 N4 O7 | 668.870 | | 669 | 3.530 | CURVE 4 |
| 56 | C37 H56 N4 O6 S | 684.937 | | 685 | 2.720 | CURVE 4 |
| 57 | C36 H54 N4 O5 S | 654.912 | | 655 | 2.740 | CURVE 4 |
| 58 | C36 H54 N4 O5 S | 654.912 | | 655 | 3.690 | CURVE 4 |
| 59 | C37 H56 N4 O5 S | 668.938 | | 669 | 7.370 | BASIS |
| 60 | C38 H54 N4 O2 | 598.871 | | 599 | 7.370 | BASIS |
| 61 | C38 H50 Cl1 F3 N4 O2 | 687.286 | | 687 | 4.600 | CURVE 4 |
| 62 | C38 H52 N4 O | 580.856 | | 581 | 8.700 | BASIS |
| 63 | C37 H52 Cl1 N5 O | 618.305 | | 618 | 4.820 | CURVE 4 |
| 64 | C37 H53 N5 O | 583.860 | | 584 | 4.340 | CURVE 4 |
| 65 | C37 H52 F1 N5 O | 601.850 | | 602 | 4.360 | CURVE 4 |
| 66 | C33 H52 N4 O2 | 536.800 | | 537 | 3.260 | CURVE 4 |
| 67 | C33 H51 N5 O2 | 549.799 | | 550 | 3.270 | CURVE 4 |
| 68 | C30 H46 N4 O2 | 494.719 | | 495 | 4.460 | STANDARD |
| 69 | C37 H52 N4 O | 568.845 | | 569 | 5.210 | STANDARD |
| 70 | C30 H46 N4 O | 478.720 | | 479 | 4.58 | STANDARD |
| 71 | C36 H60 N6 O2 | 608.910 | | 609 | 3.200 | CURVE 4 |
| 72 | C40 H59 Cl1 N6 O2 | 691.399 | | 691 | 4.350 | CURVE 4 |
| 73 | C39 H59 N7 O2 | 657.942 | | 658 | 3.630 | CURVE 4 |
| 74 | C41 H62 N6 O2 | 670.981 | | 671 | 3.560 | CURVE 4 |
| 75 | C40 H60 N6 O2 | 656.954 | | 657 | 3.930 | CURVE 4 |
| 76 | C37 H62 N6 O2 | 622.937 | | 623 | 3.180 | CURVE 4 |
| 77 | C37 H62 N6 O2 | 622.937 | | 623 | 3.010 | CURVE 4 |
| 78 | C41 H61 Cl1 N6 O2 | 705.426 | | 705 | 3.800 | CURVE 4 |
| 79 | C40 H61 N7 O2 | 671.969 | | 672 | 3.400 | CURVE 4 |
| 80 | C42 H64 N6 O2 | 685.008 | | 686 | 3.300 | CURVE 4 |
| 81 | C41 H62 N6 O2 | 670.981 | | 671 | 3.590 | CURVE 4 |
| 82 | C38 H64 N6 O2 | 636.964 | | 638 | 3.050 | CURVE 4 |
| 83 | C33 H47 N5 O | 529.768 | | 530 | 4.370 | CURVE 4 |
| 84 | C34 H48 N4 O | 528.780 | | 529 | 3.560 | CURVE 4 |
| 85 | C36 H50 N4 O2 | 570.817 | | 571 | 4.470 | CURVE 4 |
| 86 | C26 H37 N3 O3 | 439.596 | | 440 | 4.750 | STANDARD |
| 87 | C31 H42 N4 O | 486.700 | | 487 | 5.900 | CURVE 4 |
| 88 | C35 H54 N4 O3 | 578.837 | | 579 | 4.280 | CURVE 4 |
| 89 | C35 H48 N4 O3 | 572.789 | | 573 | 3.970 | CURVE 4 |
| 90 | C37 H52 N4 O5 | 632.841 | | 633 | 5.760 | STANDARD |
| 91 | C34 H56 N4 O6 | 616.838 | | 617 | 4.500 | STANDARD |
| 92 | C31 H50 N4 O3 | 526.761 | | 528 | 3.340 | STANDARD |
| 93 | C35 H57 N5 O3 | 595.867 | | 596 | 3.240 | CURVE 4 |
| 94 | C34 H56 N4 O3 | 568.841 | | 569 | 3.430 | CURVE 4 |
| 95 | C30 H46 N4 O3 | 510.723 | | 511 | 5.360 | STANDARD |
| 96 | C35 H46 N4 O4 | 586.772 | | 587 | 5.840 | CURVE 4 |
| 97 | C36 H44 F6 N4 O2 | 678.762 | | 679 | 7.060 | STANDARD |
| 98 | C34 H46 N4 O2 | 542.768 | | 543 | 6.000 | STANDARD |
| 99 | C34 H45 Br1 N4 O2 | 621.664 | | 621 | 6.290 | STANDARD |
| 100 | C34 H41 F5 N4 O2 | 632.718 | | 633 | 6.500 | STANDARD |

-continued

| Ex | Mol Formula | Mol Wgt | Melting pt. | (MH+) | Ret. Time | Method |
|---|---|---|---|---|---|---|
| 101 | C34 H44 Cl2 N4 O2 | 611.658 | | 611 | 6.610 | STANDARD |
| 102 | C35 H48 N4 O3 | 572.794 | | 573 | 5.960 | STANDARD |
| 103 | C35 H45 F3 N4 O2 | 610.765 | | 611 | 6.400 | STANDARD |
| 104 | C35 H48 N4 O2 | 556.795 | | 557 | 6.140 | STANDARD |
| 105 | C34 H45 F1 N4 O2 | 560.758 | | 561 | 6.100 | STANDARD |
| 106 | C34 H45 Cl1 N4 O2 | 577.213 | | 577 | 6.330 | STANDARD |
| 107 | C34 H44 Cl2 N4 O2 | 611.658 | | 611 | 6.690 | STANDARD |
| 108 | C35 H48 N4 O3 | 572.794 | | 573 | 6.070 | STANDARD |
| 109 | C35 H48 N4 O3 | 572.794 | | 573 | 6.020 | STANDARD |
| 110 | C34 H45 F1 N4 O2 | 560.758 | | 561 | 6.350 | STANDARD |
| 111 | C34 H45 Cl1 N4 O2 | 577.213 | | 577 | 5.980 | STANDARD |
| 112 | C35 H48 N4 O3 | 572.794 | | 573 | 7.680 | STANDARD |
| 113 | C40 H58 N4 O3 | 642.929 | | 643 | 6.490 | STANDARD |
| 114 | C35 H45 F3 N4 O2 | 610.765 | | 611 | 6.890 | STANDARD |
| 115 | C38 H54 N4 O2 | 598.876 | | 599 | 6.210 | STANDARD |
| 116 | C35 H48 N4 O2 | 556.795 | | 557 | 5.750 | STANDARD |
| 117 | C30 H44 N4 O4 | 524.706 | | 525 | 5.950 | STANDARD |
| 118 | C33 H50 N4 O4 | 566.787 | | 567 | 6.150 | STANDARD |
| 119 | C32 H50 N4 O2 | 522.778 | | 523 | 6.090 | STANDARD |
| 120 | C37 H50 N4 O4 | 614.831 | | 615 | 6.080 | STANDARD |
| 121 | C35 H48 N4 O2 | 556.795 | | 557 | 6.090 | STANDARD |
| 122 | C34 H45 Cl2 N5 O2 | 626.669 | | 626 | 1.606 | AMAP 2 |
| 123 | C31 H47 N5 O2 | 521.745 | | 522 | 1.403 | AMAP 2 |
| 124 | C34 H53 N5 O4 | 595.824 | | 596 | 1.460 | AMAP 2 |
| 125 | C39 H55 N5 O4 | 657.894 | | 658 | 1.536 | AMAP 2 |
| 126 | C35 H46 F3 N5 O3 | 641.774 | | 642 | 1.568 | AMAP 2 |
| 127 | C33 H53 N5 O2 | 551.815 | | 552 | 1.494 | AMAP 2 |
| 128 | C34 H53 N5 O4 | 595.824 | | 596 | 1.451 | AMAP 2 |
| 129 | C34 H46 Br N5 O2 | 636.674 | | 636 | 1.536 | AMAP 2 |
| 130 | C36 H51 N5 O3 | 601.831 | | 602 | 1.553 | AMAP 2 |
| 131 | C37 H51 N5 O4 | 629.841 | | 630 | 1.616 | AMAP 2 |
| 132 | C36 H51 N5 O2 | 585.832 | | 586 | 1.556 | AMAP 2 |
| 133 | C34 H45 Cl2 N5 O2 | 626.669 | | 626 | 1.583 | AMAP 2 |
| 134 | C34 H45 Cl2 N5 O2 | 626.669 | | 626 | 1.597 | AMAP 2 |
| 135 | C34 H46 Br N5 O2 | 636.674 | | 636 | 1.552 | AMAP 2 |
| 136 | C32 H48 N4 O2 | 520.762 | | 521 | 5.840 | STANDARD |
| 137 | C33 H52 N4 O2 | 536.805 | | 537 | 6.310 | STANDARD |
| 138 | C30 H46 N4 O2 | 494.724 | | 495 | 5.630 | STANDARD |
| 139 | C36 H50 N4 O2 | 570.822 | | 571 | 6.330 | STANDARD |
| 140 | C29 H41 Cl3 N4 O2 | 584.032 | | 583 | 6.540 | STANDARD |
| 141 | C29 H42 Cl2 N4 O2 | 549.587 | | 549 | 5.980 | STANDARD |
| 142 | C37 H50 N4 O2 | 582.833 | | 583 | 6.380 | STANDARD |
| 143 | C35 H54 N4 O2 | 562.843 | | 563 | 6.700 | STANDARD |
| 144 | C34 H52 N4 O2 | 548.816 | | 549 | 6.310 | STANDARD |
| 145 | C32 H44 N4 O3 | 532.729 | | 533 | 5.710 | STANDARD |
| 146 | C33 H46 N4 O2 S1 | 562.817 | | 563 | 6.020 | STANDARD |
| 147 | C41 H48 N4 O3 | 644.860 | | 645 | 6.420 | STANDARD |
| 148 | C36 H50 N4 O3 | 586.821 | | 587 | 6.150 | STANDARD |
| 149 | C31 H46 N4 O4 | 538.733 | | 539 | 5.510 | STANDARD |
| 150 | C33 H45 N5 O2 | 543.756 | | 544 | 5.340 | STANDARD |
| 151 | C41 H52 N4 O2 | 632.893 | | 633 | 6.760 | STANDARD |
| 152 | C31 H46 N4 O4 | 538.733 | | 539 | 5.540 | STANDARD |
| 153 | C43 H64 N4 O2 | 543.196 | | 543 | 6.140 | STANDARD |
| 154 | C31 H47 Cl1 N4 O2 | 543.196 | | 543 | 6.270 | STANDARD |
| 155 | C33 H51 Cl1 N4 O2 | 571.250 | | 571 | 7.540 | STANDARD |
| 156 | C39 H53 Cl1 N4 O2 | 645.332 | | 645 | 6.440 | STANDARD |
| 157 | C37 H52 N4 O3 | 600.848 | | 601 | 6.510 | STANDARD |
| 158 | C36 H46 N4 O2 S1 | 598.850 | | 599 | 6.460 | STANDARD |
| 159 | C35 H45 F3 N4 O3 | 626.764 | | 627 | 6.630 | STANDARD |
| 160 | C37 H49 N7 O2 | 623.846 | | 624 | 6.410 | STANDARD |
| 161 | C33 H43 Cl2 N5 O2 | 612.646 | | 612 | 6.460 | STANDARD |
| 162 | C36 H51 N5 O2 S1 | 617.897 | | 618 | 6.380 | STANDARD |
| 163 | C33 H43 Cl2 N5 O2 | 612.646 | | 612 | 6.440 | STANDARD |
| 164 | C38 H47 Cl1 F1 N5 O3 | 676.277 | | 676 | 6.230 | STANDARD |
| 165 | C34 H43 F3 N4 O2 | 596.738 | | 597 | 7.000 | STANDARD |
| 166 | C37 H49 F3 N4 O3 | 654.818 | | 655 | 6.480 | STANDARD |
| 167 | C40 H51 N5 O2 S1 | 665.941 | | 666 | 6.390 | STANDARD |
| 168 | C39 H48 Cl1 N5 O3 | 670.298 | | 670 | 6.370 | STANDARD |
| 169 | C33 H45 Cl1 N4 O3 S1 | 613.261 | | 613 | 6.490 | STANDARD |
| 170 | C38 H47 F3 N6 O2 | 676.828 | | 677 | 7.210 | STANDARD |
| 171 | C38 H56 N4 O2 | 600.892 | | 601 | 6.560 | STANDARD |
| 172 | C37 H47 F3 N4 O2 | 636.803 | | 637 | 6.180 | STANDARD |
| 173 | C36 H54 N6 O2 | 602.868 | | 603 | 6.300 | STANDARD |
| 174 | C36 H54 N6 O2 | 602.868 | | 603 | 6.400 | STANDARD |
| 175 | C34 H46 Cl1 N5 O3 | 608.227 | | 608 | 7.270 | STANDARD |
| 176 | C37 H51 Cl1 N4 O3 | 635.293 | | 635 | 6.300 | STANDARD |
| 177 | C37 H54 N4 O4 | 618.863 | | 619 | 6.730 | STANDARD |

-continued

| Ex | Mol Formula | Mol Wgt | Melting pt. | (MH+) | Ret. Time | Method |
|---|---|---|---|---|---|---|
| 178 | C30 H48 N4 O3 | 512.734 | | 513 | 3.280 | CURVE 4 |
| 179 | C35 H50 N4 O2 | 558.806 | | 559 | 4.140 | CURVE 4 |
| 180 | C30 H48 N4 O2 | 496.735 | | 497 | 3.450 | CURVE 4 |
| 181 | C30 H47 F N4 O2 | 514.725 | | 515 | 3.710 | CURVE 4 |
| 182 | C36 H51 Cl N4 O3 | 623.277 | | 623 | 4.410 | CURVE 4 |
| 183 | C37 H54 N4 O4 | 618.858 | | 619 | 4.090 | CURVE 4 |
| 184 | C40 H60 N4 O3 | 644.939 | | 645 | 4.980 | CURVE 4 |
| 185 | C33 H54 N4 O3 | 554.815 | | 555 | 3.810 | CURVE 4 |
| 186 | C38 H64 N4 O3 | 624.949 | | 626 | 5.530 | CURVE 4 |
| 187 | C33 H52 N4 O3 | 552.799 | | 553 | 3.800 | CURVE 4 |
| 188 | C34 H56 N4 O3 | 568.841 | | 569 | 4.110 | CURVE 4 |
| 189 | C31 H48 N4 O2 | 508.746 | | 509 | 3.730 | CURVE 4 |
| 190 | C31 H50 N4 O2 | 510.762 | | 511 | 3.570 | CURVE 4 |
| 191 | C35 H56 N4 O2 | 564.853 | | 565 | 4.390 | CURVE 4 |
| 192 | C35 H58 N4 O2 | 566.869 | | 567 | 4.740 | CURVE 4 |
| 193 | C38 H51 N5 O4 | 641.852 | | 642 | 3.980 | CURVE 4 |
| 194 | C34 H56 N4 O3 | 568.841 | | 569 | 3.930 | CURVE 4 |
| 195 | C33 H52 N4 O2 | 536.800 | | 537 | 3.960 | CURVE 4 |
| 196 | C38 H54 N4 O5 | 646.868 | | 647 | 4.180 | CURVE 4 |
| 197 | C35 H52 N4 O4 | 592.820 | | 593 | 3.890 | CURVE 4 |
| 198 | C30 H45 F3 N4 O2 | 550.706 | | 551 | 4.150 | CURVE 4 |
| 199 | C32 H48 F4 N4 O3 | 612.748 | | 613 | 4.150 | CURVE 4 |
| 200 | C34 H55 N5 O3 | 581.841 | | 582 | 3.400 | CURVE 4 |
| 201 | C37 H60 N4 O2 | 592.907 | | 593 | 5.090 | CURVE 4 |
| 202 | C36 H52 N4 O2 | 572.833 | | 573 | 4.060 | CURVE 4 |
| 203 | C32 H50 N4 O2 | 522.773 | | 523 | 4.010 | CURVE 4 |
| 204 | C32 H50 N4 O4 | 554.771 | | 555 | 4.020 | CURVE 4 |
| 205 | C41 H61 Cl N6 O2 | 705.425 | | 706 | 1.344 | AMAP 2 |
| 206 | C33 H54 N4 O2 | 538.815 | | 539 | 1.414 | AMAP 2 |
| 207 | C38 H54 N4 O4 | 630.868 | | 631 | 1.487 | AMAP 2 |
| 208 | C30 H48 N4 O3 | 512.734 | | 513 | 1.282 | AMAP 2 |
| 209 | C39 H66 N4 O2 | 622.976 | | 623 | 1.713 | AMAP 2 |
| 210 | C41 H70 N4 O2 | 651.030 | | 652 | 1.768 | AMAP 2 |
| 211 | C31 H50 N4 O3 | 526.761 | | 527 | 1.318 | AMAP 2 |
| 212 | C43 H74 N4 O2 | 679.083 | | 680 | 1.850 | AMAP 2 |
| 213 | C45 H78 N4 O2 | 707.137 | | 708 | 1.921 | AMAP 2 |
| 214 | C32 H50 N4 O2 | 522.773 | | 523 | 1.327 | AMAP 2 |
| 215 | C38 H54 N4 O5 | 646.867 | | 647 | 1.414 | AMAP 2 |
| 216 | C35 H54 N4 O2 | 562.837 | | 563 | 1.374 | AMAP 2 |
| 217 | C41 H54 N4 O2 | 634.903 | | 635 | 1.483 | AMAP 2 |
| 218 | C40 H52 N4 O | 604.878 | | 605 | 1.315 | AMAP 2 |
| 219 | C38 H50 N4 O | 578.840 | | 579 | 1.251 | AMAP 2 |
| 220 | C40 H52 N4 O2 | 620.877 | | 621 | 1.307 | AMAP 2 |
| 221 | C40 H52 N4 O | 604.878 | | 605 | 1.332 | AMAP 2 |
| 222 | C38 H50 N4 O | 578.840 | | 579 | 1.296 | AMAP 2 |
| 223 | C37 H51 N5 O | 581.844 | | 582 | 1.216 | AMAP 2 |
| 224 | C33 H47 N5 O | 529.768 | | 530 | 1.171 | AMAP 2 |
| 225 | C35 H47 F3 N4 O | 596.777 | | 597 | 1.310 | AMAP 2 |
| 226 | C33 H47 N5 O | 529.768 | | 530 | 1.136 | AMAP 2 |
| 227 | C31 H48 N4 O | 492.747 | | 493 | 1.153 | AMAP 2 |
| 228 | C35 H47 Cl1 N4 O3 | 607.234 | | 607 | 1.273 | AMAP 2 |
| 229 | C35 H47 F3 N4 O2 | 612.776 | | 613 | 1.298 | AMAP 2 |
| 230 | C36 H50 N4 O2 | 570.817 | | 571 | 1.212 | AMAP 2 |
| 231 | C35 H56 N4 O | 548.854 | | 549 | 1.255 | AMAP 2 |
| 232 | C38 H56 N4 O | 584.887 | | 585 | 1.315 | AMAP 2 |
| 233 | C35 H50 N4 O2 | 558.806 | | 559 | 1.217 | AMAP 2 |
| 234 | C35 H47 N5 O | 553.790 | | 554 | 1.245 | AMAP 2 |
| 235 | C33 H49 N5 O2 | 547.783 | | 548 | 1.187 | AMAP 2 |
| 236 | C35 H50 N4 O3 S | 606.871 | | 607 | 1.305 | AMAP 2 |
| 237 | C35 H50 N4 O | 542.807 | | 543 | 1.212 | AMAP 2 |
| 238 | C37 H50 N6 O3 | 626.841 | | 627 | 1.209 | AMAP 2 |
| 239 | C34 H47 F N4 O | 546.770 | | 547 | 1.214 | AMAP 2 |
| 240 | C41 H54 N4 O2 | 634.904 | | 635 | 1.307 | AMAP 2 |
| 241 | C34 H47 Cl1 N4 O | 563.225 | | 563 | 1.251 | AMAP 2 |
| 242 | C48 H60 N4 O3 | 741.027 | | 741 | 1.369 | AMAP 2 |
| 243 | C35 H47 F3 N4 O2 | 612.776 | | 613 | 1.321 | AMAP 2 |
| 244 | C32 H52 N4 O | 508.790 | | 509 | 1.192 | AMAP 2 |
| 245 | C36 H52 N4 O | 556.834 | | 557 | 1.228 | AMAP 2 |
| 246 | C30 H47 N5 O2 | 509.734 | | 510 | 1.099 | AMAP 2 |
| 247 | C32 H46 N6 O3 | 562.754 | | 563 | 1.273 | AMAP 2 |
| 248 | C37 H54 N4 O2 | 586.860 | | 587 | 1.228 | AMAP 2 |
| 249 | C32 H45 Cl1 N4 O S | 569.253 | | 569 | 1.339 | AMAP 2 |
| 250 | C31 H48 N4 O3 | 524.745 | | 525 | 1.144 | AMAP 2 |
| 251 | C36 H52 N4 O | 556.834 | | 557 | 1.237 | AMAP 2 |
| 252 | C29 H43 N5 O | 477.693 | | 478 | 1.392 | AMAP 2 |
| 253 | C34 H47 F N4 O | 546.770 | | 547 | 1.221 | AMAP 2 |
| 254 | C35 H47 F3 N4 O | 596.777 | | 597 | 1.301 | AMAP 2 |

-continued

| Ex | Mol Formula | Mol Wgt | Melting pt. | (MH⁺) | Ret. Time | Method |
|---|---|---|---|---|---|---|
| 255 | C35 H47 N5 O | 553.790 | | 554 | 1.377 | AMAP 2 |
| 256 | C32 H52 N4 O | 508.790 | | 509 | 1.197 | AMAP 2 |
| 257 | C29 H46 N4 O2 | 482.708 | | 483 | 1.103 | AMAP 2 |
| 258 | C34 H47 Cl1 N4 O | 563.225 | | 563 | 1.268 | AMAP 2 |
| 259 | C42 H52 N4 O | 628.900 | | 629 | 1.430 | AMAP 2 |
| 260 | C35 H50 N4 O | 542.807 | | 543 | 1.229 | AMAP 2 |
| 261 | C34 H47 Br N4 O | 607.676 | | 607 | 1.258 | AMAP 2 |
| 262 | C35 H50 N4 O | 542.807 | | 543 | 1.207 | AMAP 2 |
| 263 | C35 H47 N5 O | 553.790 | | 554 | 1.244 | AMAP 2 |
| 264 | C35 H48 N4 O2 | 556.790 | | 557 | 1.226 | AMAP 2 |
| 265 | C29 H45 N5 O2 | 495.707 | | 496 | 1.106 | AMAP 2 |
| 266 | C37 H52 N4 O4 | 616.842 | | 617 | 1.235 | AMAP 2 |
| 267 | C39 H58 N4 O2 | 614.913 | | 615 | 1.298 | AMAP 2 |
| 268 | C38 H52 N4 O4 | 628.853 | | 629 | 1.231 | AMAP 2 |
| 269 | C41 H52 N4 O2 | 632.888 | | 633 | 1.435 | AMAP 2 |
| 270 | C31 H50 N4 O | 494.763 | | 495 | 1.164 | AMAP 2 |
| 271 | C42 H54 N4 O | 630.916 | | 631 | 1.337 | AMAP 2 |
| 272 | C36 H52 N4 O2 | 572.833 | | 573 | 1.227 | AMAP 2 |
| 273 | C34 H47 F N4 O | 546.770 | | 547 | 1.199 | AMAP 2 |
| 274 | C35 H50 N4 O2 | 558.806 | | 559 | 1.209 | AMAP 2 |
| 275 | C33 H47 N5 O | 529.768 | | 530 | 1.167 | AMAP 2 |
| 276 | C35 H50 N4 O2 | 558.806 | | 559 | 1.202 | AMAP 2 |
| 277 | C40 H51 N5 O3 | 649.875 | | 650 | 1.579 | AMAP 2 |
| 278 | C35 H49 N5 O2 | 571.805 | | 572 | 1.441 | AMAP 2 |
| 279 | C40 H51 N5 O2 | 633.876 | | 634 | 1.594 | AMAP 2 |
| 280 | C40 H51 N5 O2 | 633.876 | | 634 | 1.595 | AMAP 2 |
| 281 | C35 H49 N5 O3 | 587.804 | | 588 | 1.503 | AMAP 2 |
| 282 | C34 H46 F N5 O2 | 575.768 | | 576 | 1.479 | AMAP 2 |
| 283 | C35 H46 N6 O2 | 582.788 | | 583 | 1.434 | AMAP 2 |
| 284 | C38 H57 N5 O2 | 615.901 | | 616 | 1.599 | AMAP 2 |
| 285 | C34 H46 F N5 O2 | 575.768 | | 576 | 1.465 | AMAP 2 |
| 286 | C35 H49 N5 O3 | 587.804 | | 588 | 1.449 | AMAP 2 |
| 287 | C35 H46 N6 O2 | 582.788 | | 583 | 1.456 | AMAP 2 |
| 288 | C37 H51 N5 O4 | 629.841 | | 630 | 1.516 | AMAP 2 |
| 289 | C36 H51 N5 O2 | 585.832 | | 586 | 1.484 | AMAP 2 |
| 290 | C40 H53 N5 O2 | 635.892 | | 636 | 1.564 | AMAP 2 |
| 291 | C34 H45 Cl2 N5 O2 | 626.669 | | 626 | 1.465 | AMAP 2 |
| 292 | C34 H46 Cl1 N5 O2 | 592.223 | | 592 | 1.524 | AMAP 2 |
| 293 | C34 H46 Cl1 N5 O2 | 592.223 | | 592 | 1.522 | AMAP 2 |
| 294 | C32 H51 N5 O2 | 537.788 | | 538 | 1.467 | AMAP 2 |
| 295 | C36 H51 N5 O2 | 585.832 | | 586 | 1.490 | AMAP 2 |
| 296 | C32 H51 N5 O2 | 537.788 | | 538 | 1.451 | AMAP 2 |
| 297 | C37 H53 N5 O5 | 647.856 | | 648 | 1.417 | AMAP 2 |
| 298 | C36 H51 N5 O4 | 617.830 | | 618 | 1.482 | AMAP 2 |
| 299 | C35 H47 N5 O3 | 585.788 | | 586 | 1.429 | AMAP 2 |
| 300 | C31 H49 N5 O2 | 523.761 | | 524 | 1.390 | AMAP 2 |
| 301 | C34 H46 N6 O4 | 602.775 | | 603 | 1.464 | AMAP 2 |
| 302 | C35 H49 N5 O2 S | 603.871 | | 604 | 1.532 | AMAP 2 |
| 303 | C32 H49 N5 O4 | 567.770 | | 568 | 1.392 | AMAP 2 |
| 304 | C34 H46 Br N5 O2 | 636.674 | | 636 | 1.535 | AMAP 2 |
| 305 | C38 H55 N5 O2 | 613.885 | | 614 | 1.650 | AMAP 2 |
| 306 | C38 H53 N5 O4 | 643.868 | | 644 | 1.498 | AMAP 2 |
| 307 | C36 H51 N5 O4 | 617.830 | | 618 | 1.510 | AMAP 2 |
| 308 | C35 H49 N5 O2 | 571.805 | | 572 | 1.459 | AMAP 2 |
| 309 | C36 H51 N5 O2 | 585.832 | | 586 | 1.472 | AMAP 2 |
| 310 | C34 H45 Cl2 N5 O2 | 626.669 | | 626 | 1.578 | AMAP 2 |
| 311 | C37 H51 N5 O4 | 629.841 | | 630 | 1.501 | AMAP 2 |
| 312 | C34 H46 N6 O4 | 602.775 | | 603 | 1.489 | AMAP 2 |
| 313 | C36 H45 F6 N5 O2 | 693.773 | | 694 | 1.660 | AMAP 2 |
| 314 | C37 H53 N5 O2 | 599.859 | | 600 | 1.509 | AMAP 2 |
| 315 | C39 H55 N5 O4 | 657.894 | | 658 | 1.591 | AMAP 2 |
| 316 | C33 H51 N5 O4 | 581.797 | | 582 | 1.395 | AMAP 2 |
| 317 | C36 H59 N5 O2 | 593.895 | | 594 | 1.631 | AMAP 2 |
| 318 | C34 H45 F2 N5 O2 | 593.758 | | 594 | 1.465 | AMAP 2 |
| 319 | C34 H45 Cl2 N5 O2 | 626.669 | | 626 | 1.606 | AMAP 2 |
| 320 | C35 H49 N5 O2 | 571.805 | | 572 | 1.497 | AMAP 2 |
| 321 | C31 H47 N5 O2 | 521.745 | | 522 | 1.403 | AMAP 2 |
| 322 | C34 H53 N5 O4 | 595.824 | | 596 | 1.460 | AMAP 2 |
| 323 | C39 H55 N5 O4 | 657.894 | | 658 | 1.536 | AMAP 2 |
| 324 | C35 H46 F3 N5 O3 | 641.774 | | 642 | 1.568 | AMAP 2 |
| 325 | C33 H53 N5 O2 | 551.815 | | 552 | 1.494 | AMAP 2 |
| 326 | C34 H53 N5 O4 | 595.824 | | 596 | 1.451 | AMAP 2 |
| 327 | C34 H46 Br N5 O2 | 636.674 | | 636 | 1.536 | AMAP 2 |
| 328 | C36 H51 N5 O3 | 601.831 | | 602 | 1.553 | AMAP 2 |
| 329 | C37 H51 N5 O4 | 629.841 | | 630 | 1.616 | AMAP 2 |
| 330 | C36 H51 N5 O2 | 585.832 | | 586 | 1.556 | AMAP 2 |
| 331 | C34 H45 Cl2 N5 O2 | 626.669 | | 626 | 1.583 | AMAP 2 |

-continued

| Ex | Mol Formula | Mol Wgt | Melting pt. | (MH+) | Ret. Time | Method |
|---|---|---|---|---|---|---|
| 332 | C34 H45 Cl2 N5 O2 | 626.669 | | 626 | 1.597 | AMAP 2 |
| 333 | C34 H46 Br N5 O2 | 636.674 | | 636 | 1.552 | AMAP 2 |
| 334 | C40 H59 N5 O2 | 641.939 | | 642 | 1.601 | AMAP 2 |
| 335 | C31 H47 N5 O4 | 553.743 | | 554 | 1.363 | AMAP 2 |
| 336 | C36 H51 N5 O2 | 585.832 | | 586 | 1.509 | AMAP 2 |
| 337 | C35 H48 Cl1 N5 O3 | 622.249 | | 622 | 1.551 | AMAP 2 |
| 338 | C35 H45 Cl1 F3 N5 O2 | 660.221 | | 660 | 1.614 | AMAP 2 |
| 339 | C35 H45 Cl1 F3 N5 O2 | 660.221 | | 660 | 1.648 | AMAP 2 |
| 340 | C36 H51 N5 O3 | 601.831 | | 602 | 1.475 | AMAP 2 |
| 341 | C34 H45 Cl1 N6 O4 | 637.221 | | 637 | 1.596 | AMAP 2 |
| 342 | C38 H55 N5 O2 | 613.885 | | 614 | 1.539 | AMAP 2 |
| 343 | C35 H48 Cl1 N5 O2 | 606.250 | | 606 | 1.481 | AMAP 2 |
| 344 | C36 H50 Br N5 O2 | 664.728 | | 664 | 1.543 | AMAP 2 |
| 345 | C36 H57 N5 O4 | 623.877 | | 624 | 1.470 | AMAP 2 |
| 346 | C33 H51 N5 O4 | 581.797 | | 582 | 1.421 | AMAP 2 |
| 347 | C34 H45 N7 O6 | 647.773 | | 648 | 1.575 | AMAP 2 |
| 348 | C40 H56 N6 O4 | 684.920 | | 685 | 1.169 | AMAP 2 |
| 349 | C40 H55 N7 O3 | 681.920 | | 682 | 1.348 | AMAP 2 |
| 350 | C37 H51 N5 O2 | 597.843 | | 598 | 1.476 | AMAP 2 |
| 351 | C32 H47 N5 O2 | 533.756 | | 534 | 1.372 | AMAP 2 |
| 352 | C38 H54 N6 O2 | 626.885 | | 627 | 1.456 | AMAP 2 |
| 353 | C32 H49 N5 O3 | 551.771 | | 552 | 1.320 | AMAP 2 |
| 354 | C37 H53 N7 O2 | 627.873 | | 628 | 1.229 | AMAP 2 |
| 355 | C36 H52 N6 O2 | 600.847 | | 601 | 1.220 | AMAP 2 |
| 356 | C32 H49 N5 O2 | 535.772 | | 536 | 1.357 | AMAP 2 |
| 357 | C40 H55 N5 O4 | 669.906 | | 670 | 1.497 | AMAP 2 |
| 358 | C38 H53 F N6 O2 | 644.875 | | 645 | 1.480 | AMAP 2 |
| 359 | C39 H56 N6 O3 | 656.910 | | 657 | 1.439 | AMAP 2 |
| 360 | C39 H54 Cl1 N5 O3 | 676.341 | | 676 | 1.431 | AMAP 2 |
| 361 | C39 H53 F3 N6 O2 | 694.882 | | 695 | 1.563 | AMAP 2 |
| 362 | C39 H55 Cl1 N6 O2 | 675.357 | | 676 | 1.236 | AMAP 2 |
| 363 | C31 H47 N5 O2 S | 553.811 | | 554 | 1.374 | AMAP 2 |
| 364 | C36 H58 N6 O4 | 638.892 | | 639 | 1.104 | AMAP 2 |
| 365 | C32 H51 N5 O2 | 537.788 | | 538 | 1.414 | AMAP 2 |
| 366 | C35 H53 N5 O4 | 607.835 | | 608 | 1.386 | AMAP 2 |
| 367 | C36 H55 N5 O4 | 621.862 | | 622 | 1.409 | AMAP 2 |
| 368 | C39 H52 N6 O2 | 636.880 | | 637 | 1.466 | AMAP 2 |
| 369 | C39 H55 N5 O3 | 641.896 | | 642 | 1.388 | AMAP 2 |
| 370 | C40 H53 N5 O2 | 635.892 | | 636 | 1.525 | AMAP 2 |
| 371 | C39 H56 N6 O3 | 656.910 | | 657 | 1.423 | AMAP 2 |
| 372 | C36 H52 N8 O2 | 628.861 | | 629 | 1.332 | AMAP 2 |
| 373 | C34 H52 N6 O3 | 592.824 | | 593 | 1.263 | AMAP 2 |
| 374 | C43 H57 N5 O2 | 675.956 | | 676 | 1.616 | AMAP 2 |
| 375 | C34 H55 N5 O4 | 597.839 | | 598 | 1.355 | AMAP 2 |
| 376 | C39 H53 F3 N6 O2 | 694.882 | | 695 | 1.557 | AMAP 2 |
| 377 | C32 H49 N5 O3 | 551.771 | | 552 | 1.271 | AMAP 2 |
| 378 | C34 H53 N5 O3 | 579.825 | | 580 | 1.368 | AMAP 2 |
| 379 | C41 H57 N7 O3 | 695.947 | | 695 | 1.398 | AMAP 2 |
| 380 | C38 H53 F N6 O2 | 644.875 | | 645 | 1.486 | AMAP 2 |
| 381 | C37 H53 N7 O2 | 627.873 | | 628 | 1.145 | AMAP 2 |
| 382 | C33 H51 N5 O3 | 565.798 | | 566 | 1.258 | AMAP 2 |
| 383 | C32 H51 N5 O3 | 553.787 | | 554 | 1.301 | AMAP 2 |
| 384 | C33 H51 N5 O3 | 565.798 | | 566 | 1.272 | AMAP 2 |
| 385 | C32 H51 N5 O2 | 537.788 | | 538 | 1.410 | AMAP 2 |
| 386 | C37 H51 N5 O4 | 629.841 | | 630 | 1.452 | AMAP 2 |
| 387 | C33 H54 N6 O2 | 566.830 | | 566 | 1.122 | AMAP 2 |
| 388 | C37 H53 N5 O2 | 599.859 | | 600 | 1.484 | AMAP 2 |
| 389 | C32 H49 N5 O2 | 535.772 | | 536 | 1.397 | AMAP 2 |
| 390 | C33 H49 N5 O2 | 547.783 | | 548 | 1.393 | AMAP 2 |
| 391 | C33 H50 N6 O3 | 578.797 | | 579 | 1.256 | AMAP 2 |
| 392 | C40 H58 N6 O3 | 670.937 | | 671 | 1.488 | AMAP 2 |
| 393 | C31 H49 N5 O2 | 523.761 | | 524 | 1.378 | AMAP 2 |
| 394 | C38 H60 N6 O2 | 632.932 | | 633 | 1.163 | AMAP 2 |
| 395 | C30 H47 N5 O2 | 509.734 | | 510 | 1.331 | AMAP 2 |
| 396 | C37 H58 N6 O2 | 618.905 | | 619 | 1.123 | AMAP 2 |
| 397 | C34 H45 F2 N5 O2 | 593.758 | | 594 | 1.465 | AMAP 2 |
| 398 | C35 H49 N5 O2 | 571.805 | | 572 | 1.497 | AMAP 2 |
| 399 | C34 H46 N4 O3 | 558.762 | | 559 | 1.985 | AMAP 3 |
| 400 | C32 H50 N4 O3 | 538.772 | | 539 | 2.010 | AMAP 3 |
| 401 | C29 H44 N4 O3 | 496.692 | | 497 | 1.914 | AMAP 3 |
| 402 | C31 H46 N4 O3 | 522.729 | | 523 | 1.950 | AMAP 3 |
| 403 | C35 H48 N4 O4 | 588.788 | | 589 | 1.976 | AMAP 3 |
| 404 | C31 H48 N4 O4 | 540.744 | | 541 | 1.885 | AMAP 3 |
| 405 | C36 H58 N4 O3 | 594.879 | | 595 | 2.206 | AMAP 3 |
| 406 | C31 H48 N4 O3 | 524.745 | | 525 | 1.966 | AMAP 3 |
| 407 | C34 H45 F N4 O3 | 576.753 | | 577 | 2.014 | AMAP 3 |
| 408 | C34 H45 Cl N4 O3 | 593.208 | | 593 | 2.036 | AMAP 3 |

-continued

| Ex | Mol Formula | Mol Wgt | Melting pt. | (MH+) | Ret. Time | Method |
|---|---|---|---|---|---|---|
| 409 | C35 H47 N5 O5 | 617.786 | | 618 | 1.981 | AMAP 3 |
| 410 | C38 H60 N4 O3 | 620.917 | | 621 | 2.249 | AMAP 3 |
| 411 | C35 H48 N4 O3 | 572.789 | | 573 | 2.040 | AMAP 3 |
| 412 | C32 H50 N4 O3 | 538.772 | | 539 | 2.002 | AMAP 3 |
| 413 | C32 H48 N4 O3 | 536.756 | | 537 | 1.995 | AMAP 3 |
| 414 | C30 H46 N4 O3 | 510.718 | | 511 | 1.918 | AMAP 3 |
| 415 | C31 H44 N4 O3 | 520.714 | | 521 | 1.919 | AMAP 3 |
| 416 | C32 H47 ClS N4 O3 | 642.107 | | 641 | 2.137 | AMAP 3 |
| 417 | C34 H45 N5 O5 | 603.760 | | 604 | 2.024 | AMAP 3 |
| 418 | C30 H43 ClS N4 OS | 614.054 | | 613 | 2.043 | AMAP 3 |
| 419 | C38 H60 N4 OS | 620.917 | | 621 | 2.280 | AMAP 3 |
| 420 | C37 H48 N4 OS S | 628.877 | | 629 | 1.519 | AMAP 2 |
| 421 | C31 H44 N4 OS S2 | 584.846 | | 585 | 1.417 | AMAP 2 |
| 422 | C36 H47 N5 OS S | 629.865 | | 630 | 1.428 | AMAP 2 |
| 423 | C39 H50 N4 OS S | 654.915 | | 655 | 1.576 | AMAP 2 |
| 424 | C37 H48 N4 OS S | 628.877 | | 629 | 1.524 | AMAP 2 |
| 425 | C33 H46 N4 OS S | 578.817 | | 579 | 1.427 | AMAP 2 |
| 426 | C33 H45 F N4 OS S | 596.807 | | 597 | 1.439 | AMAP 2 |
| 427 | C36 H52 N4 OS S | 620.898 | | 621 | 1.571 | AMAP 2 |
| 428 | C34 H48 N4 O5 S2 | 656.908 | | 657 | 1.354 | AMAP 2 |
| 429 | C34 H48 N4 O4 S | 608.843 | | 609 | 1.409 | AMAP 2 |
| 430 | C33 H45 F N4 OS S | 596.807 | | 597 | 1.426 | AMAP 2 |
| 431 | C35 H50 N4 O5 S | 638.869 | | 639 | 1.375 | AMAP 2 |
| 432 | C34 H45 F3 N4 O3 S | 646.815 | | 647 | 1.489 | AMAP 2 |
| 433 | C34 H45 N5 O3 S | 603.828 | | 604 | 1.411 | AMAP 2 |
| 434 | C37 H54 N4 O3 S | 634.925 | | 635 | 1.593 | AMAP 2 |
| 435 | C39 H53 N5 O3 S | 671.946 | | 672 | 1.575 | AMAP 2 |
| 436 | C33 H45 Cl1 N4 O3 S | 613.263 | | 613 | 1.502 | AMAP 2 |
| 437 | C35 H49 N5 O4 S | 635.869 | | 636 | 1.327 | AMAP 2 |
| 438 | C31 H43 Cl1 N4 O3 S2 | 619.291 | | 619 | 1.504 | AMAP 2 |
| 439 | C34 H45 F3 N4 O3 S | 646.815 | | 647 | 1.494 | AMAP 2 |
| 440 | C33 H44 N6 O3 S2 | 636.882 | | 637 | 1.433 | AMAP 2 |
| 441 | C33 H48 N6 O4 S2 | 656.912 | | 657 | 1.332 | AMAP 2 |
| 442 | C37 H48 N4 O5 S3 | 725.007 | | 725 | 1.467 | AMAP 2 |
| 443 | C36 H52 N4 O3 S | 620.898 | | 621 | 1.545 | AMAP 2 |
| 444 | C35 H48 N4 O3 S | 604.855 | | 605 | 1.479 | AMAP 2 |
| 445 | C35 H50 N4 O5 S | 638.869 | | 639 | 1.419 | AMAP 2 |
| 446 | C33 H44 Cl2 N4 O3 S | 647.708 | | 647 | 1.563 | AMAP 2 |
| 447 | C33 H44 F2 N4 O3 S | 614.798 | | 615 | 1.454 | AMAP 2 |
| 448 | C34 H48 N4 O3 S | 592.844 | | 593 | 1.465 | AMAP 2 |
| 449 | C33 H45 Cl1 N4 O3 S | 613.263 | | 613 | 1.474 | AMAP 2 |
| 450 | C33 H45 Cl1 N4 O3 S | 613.263 | | 613 | 1.474 | AMAP 2 |
| 451 | C33 H44 Cl2 N4 O3 S | 647.708 | | 647 | 1.480 | AMAP 2 |
| 452 | C33 H44 Cl2 N4 O3 S | 647.708 | | 647 | 1.541 | AMAP 2 |
| 453 | C33 H45 N5 O5 S | 623.815 | | 624 | 1.418 | AMAP 2 |
| 454 | C28 H44 N4 O3 S | 516.747 | | 517 | 1.280 | AMAP 2 |
| 455 | C34 H45 F3 N4 O4 S | 662.813 | | 663 | 1.530 | AMAP 2 |
| 456 | C34 H48 N4 O3 S | 592.844 | | 593 | 1.465 | AMAP 2 |
| 457 | C33 H45 N5 O5 S | 623.815 | | 624 | 1.434 | AMAP 2 |
| 458 | C36 H52 N4 O3 S | 620.898 | | 621 | 1.584 | AMAP 2 |
| 459 | C34 H45 F3 N4 O3 S | 646.815 | | 647 | 1.499 | AMAP 2 |
| 460 | C33 H45 Br N4 O3 S | 657.714 | | 657 | 1.524 | AMAP 2 |
| 461 | C37 H48 N4 O5 S3 | 725.007 | | 725 | 1.498 | AMAP 2 |
| 462 | C34 H48 N4 O5 S2 | 656.908 | | 657 | 1.372 | AMAP 2 |
| 463 | C33 H45 Br N4 O3 S | 657.714 | | 657 | 1.488 | AMAP 2 |
| 464 | C34 H46 N4 O5 S | 622.826 | | 623 | 1.361 | AMAP 2 |
| 465 | C33 H45 N5 O5 S | 623.815 | | 624 | 1.424 | AMAP 2 |
| 466 | C33 H44 Cl2 N4 O3 S | 647.708 | | 647 | 1.596 | AMAP 2 |
| 467 | C31 H42 Cl2 N4 O3 S2 | 653.736 | | 653 | 1.607 | AMAP 2 |
| 468 | C33 H45 Br N4 O3 S | 657.714 | | 657 | 1.527 | AMAP 2 |
| 469 | C37 H54 N4 O4 S | 650.924 | | 651 | 1.594 | AMAP 2 |
| 470 | C33 H45 I N4 O3 S | 704.709 | | 705 | 1.540 | AMAP 2 |
| 471 | C33 H44 Cl2 N4 O3 S | 647.708 | | 647 | 1.559 | AMAP 2 |
| 472 | C38 H56 N4 O3 S | 648.951 | | 649 | 1.679 | AMAP 2 |
| 473 | C34 H47 N5 O5 S | 637.841 | | 638 | 1.500 | AMAP 2 |
| 474 | C35 H44 F6 N4 O3 S | 714.812 | | 715 | 1.630 | AMAP 2 |
| 475 | C35 H50 N4 O3 S | 606.871 | | 607 | 1.541 | AMAP 2 |
| 476 | C31 H42 Cl2 N4 O3 S2 | 653.736 | | 653 | 1.577 | AMAP 2 |
| 477 | C34 H47 Br N4 O4 S | 687.739 | | 687 | 1.531 | AMAP 2 |
| 478 | C33 H44 Cl1 F N4 O3 S | 631.253 | | 631 | 1.490 | AMAP 2 |
| 479 | C34 H47 F N4 O3 S | 610.834 | | 611 | 1.498 | AMAP 2 |
| 480 | C41 H55 N7 O3 S | 725.997 | | 726 | 1.682 | AMAP 2 |
| 481 | C33 H44 N6 O7 S | 668.812 | | 669 | 1.475 | AMAP 2 |
| 482 | C31 H42 Br2 N4 O3 S2 | 742.638 | | 741 | 1.605 | AMAP 2 |
| 483 | C31 H41 Br Cl2 N4 O3 S2 | 732.632 | | 731 | 1.622 | AMAP 2 |
| 484 | C33 H44 Cl2 N4 O3 S | 647.708 | | 647 | 1.552 | AMAP 2 |
| 485 | C33 H43 Cl3 N4 O3 S | 682.153 | | 681 | 1.587 | AMAP 2 |

-continued

| Ex | Mol Formula | Mol Wgt | Melting pt. | (MH+) | Ret. Time | Method |
|---|---|---|---|---|---|---|
| 486 | C34 H47 Cl1 N4 O3 S | 627.289 | | 627 | 1.524 | AMAP 2 |
| 487 | C42 H64 N4 O3 S | 705.059 | | 705 | 1.819 | AMAP 2 |
| 488 | C36 H47 Cl1 N4 O3 S2 | 683.377 | | 683 | 1.654 | AMAP 2 |

Analytical Methods (GC-MS)

Basis Method

API 100 95: MassChrom

Solvents:

| A % | 95% NH$_4$OAc buffer + 5% acetonitrile |
|---|---|
| B % | 100% acetonitrile |
| Flow Ramp | 5.00 |
| Flow (ml/min) | 1.000 |
| Stop Time (mins) | 20.00 |
| Min Pressure (Psi) | 0 |
| Max Pressure (Psi) | 6100 |

LC-200 Quad Pump (Version 1.08)

| Column: | XTerra (2.5 µm, 4.5 × 50 mm) |
|---|---|
| Column Temperature (° C.) | 20 |
| Column Temperature Limit (° C.) | 20 |

Gradient Timetable: 0.00=isocratic, 1.00=linear

| Step | Time(min) | Dura. (min.) | A % | B % | Flow(ml/min) | Grad. |
|---|---|---|---|---|---|---|
| 0 | −0.10 | 0.10 | 100 | 0 | 1.000 | 0.00 |
| 1 | 0.00 | 10.00 | 5 | 95 | 1.000 | 1.00 |
| 2 | 10.00 | 2.00 | 5 | 95 | 1.000 | 0.00 |
| 3 | 12.00 | 0.50 | 100 | 0 | 1.000 | 1.00 |
| 4 | 12.50 | 2.50 | 100 | 0 | 1.000 | 0.00 |

Number of Channels: 2

| Sampling Rate: | 0 points per second per channel |
|---|---|
| Voltage Range: | 0 till 0.1 volt |
| Polarity: | UNIPOLAR |
| Channel A: | (A) UV 225 nm |
| Channel B: | (B) ELS Sedex 75 (Temp. 37° C.) |

Standard Method

Waters Alliance 2790 LC Mobile Phase

Solvents:

| C % | 95% NH$_4$OAc buffer + 5% ACN (pH = ±5) |
|---|---|
| D % | 100% acetonitrile (ACN) |
| Flow Ramp | 5.00 |
| Flow (ml/min) | 1.000 |
| Stop Time (mins) | 11.00 |

-continued

| Min Pressure (Bar) | 0 |
|---|---|
| Max Pressure (Bar) | 300 |
| Degasser OnStroke Length | Auto |

Waters Alliance 2790 LC Column

| Column Position Column 1 Equilibration Time (mins) | 0.00 |
|---|---|
| Column Temperature (° C.) | 20 |
| Column Temperature Limit (° C.) | 20 |

Waters Alliance 2790 LC Rapid Equilibration

| System Path OffSystem Flow (ml/min) | 0.00 |
|---|---|
| System Time (mins) | 0.00 |
| Re-equilibration Time (mins) | 0.00 |
| Pre column volume (µl) | 0.00 |

Waters Alliance 2790 I/O

Switch 1: no change; switch 2: no change; switch 3: no change; switch 4: no change Analog Output Setting: Flow Rate Waters Alliance 2790 LC Gradient Timetable The gradient Timetable contains 6 entries which are:

| Time(min) | C % | D % | Flow(ml/min) | Curve |
|---|---|---|---|---|
| 0.00 | 100.0 | 0.0 | 1.000 | 1 |
| 1.00 | 100.0 | 0.0 | 1.000 | 6 |
| 7.00 | 0.0 | 100.0 | 1.000 | 6 |
| 8.00 | 0.0 | 100.0 | 1.000 | 6 |
| 8.50 | 100.0 | 0.0 | 1.000 | 6 |
| 11.00 | 100.0 | 0.0 | 1.000 | 6 |

| Start Wavelength (nm) | 225.00 |
|---|---|
| End Wavelength (nm) | 260.00 |
| Resolution (nm) | 1.2 |
| Sampling Rate (spectra/second) | 1.000 |
| Filter Response | 1 |
| Exposure Time(ms) Automatic Interpolate | 656 |
| YesAcquisition stop time (mins) | 10.75 |
| Waters996 PDA Analog Channel 1 | |
| ELS PL ELS 1000 (Temp. 80° C.) | |

Curve 4 Method

Waters Alliance 2790 LC Mobile Phase

Solvents

| | |
|---|---|
| C % | 95% NH$_4$OAc buffer + 5% ACN (pH = ± 5) |
| D % | 100% acetonitrile |
| Flow Ramp | 5.00 |
| Flow (ml/min) | 1.000 |
| Stop Time (mins) | 11.00 |
| Min Pressure (Bar) | 0 |
| Max Pressure (Bar) | 320 |
| Degasser   OnStroke Lenqth | Auto |

Waters Alliance 2790 LC Column

| | |
|---|---|
| Column Position Column 1 Equilibration Time (mins) | 0.00 |
| Column Temperature (° C.) | 20 |
| Column Temperature Limit (° C.) | 20 |

Waters Alliance 2790 LC Rapid Equilibration

| | |
|---|---|
| System Path OffSystem Flow (ml/min) | 0.00 |
| System Time (mins) | 0.00 |
| Re-equilibration Time (mins) | 0.00 |
| Pre column volume (µl) | 0.00 |

Waters Alliance 2790 I/O

Switch 1 No Change Switch 2 No Change Switch 3 No Change Switch 4 No Change Analog Output Setting Flow Rate Waters Alliance 2790 LC Gradient Timetable The gradient Timetable contains 6 entries which are:

| Time(min) | C % | D % | Flow | Curve |
|---|---|---|---|---|
| 0.00 | 100.0 | 0.0 | 1.000 | 1 |
| 1.00 | 100.0 | 0.0 | 1.000 | 4 |
| 7.00 | 0.0 | 100.0 | 1.000 | 4 |
| 8.00 | 0.0 | 100.0 | 1.000 | 6 |
| 9.00 | 100.0 | 0.0 | 1.000 | 6 |
| 11.00 | 100.0 | 0.0 | 1.000 | 6 |
| Start Wavelength (nm) | | | | 205.00 |
| End Wavelength (nm) | | | | 350.00 |
| Resolution (nm) | | | | 1.2 |
| Sampling Rate (spectra/s) | | | | 1.000 |
| Filter Response | | | | 1 |
| Exposure Time(ms) AutomaticInterpolate | | | | 656 |
| YesAcquisition stop time (mins) | | | | 10.75 |
| Waters996 PDA Analog Channel 1 | | | | |
| ELS PL ELS 1000 (Temp. 80° C.) | | | | |

AMAP 2 Method

The LC-MS system consists of 2 Perkin Elmer series 200 micro pumps. The pumps are connected to each other by a 50 µl tee mixer. The mixer is connected to the Gilson 215 auto sampler.

The LC method is:

| step | total time | flow (µl/min) | A(%) | B(%) |
|---|---|---|---|---|
| 0 | 0 | 2300 | 95 | 5 |
| 1 | 1.6 | 2300 | 0 | 100 |
| 2 | 1.8 | 2300 | 0 | 100 |
| 3 | 1 | 2300 | 95 | 5 |
| 4 | 2.2 | 2300 | 95 | 5 |

A = 100% Water with 0.025% HCOOH and 10 mmol NH$_4$HCOO pH = ± 3
B = 100% ACN with 0.025% HCOOH The auto sampler has a 2 µl injection loop. The auto sampler is connected to a Phenomenex Luna C18(2) 30*4.6 mm column with 3 um particles. The column is thermo stated in a Perkin Elmer series 200 column oven at 40° C. The column is connected to an Applied biosystems ABI 785 UV meter with a 2.7 µl flowcell. The wavelength is set to 254 nm. The UV meter is connected to a Sciex API 150EX mass spectrometer. The mass spectrometer has the following parameters:

| | |
|---|---|
| Scanrange: | 150–900 Amu |
| Polarity: | positive |
| Scan mode: | profile |
| Resolution Q1: | UNIT |
| Step size: | 0.10 amu |
| Time per scan: | 0.500 sec |
| Nebulizer (NEB): | 10 |
| Curtain gas (CUR): | 10 |
| Ion Source (IS): | 5200 volt |
| Temperature (TEM): | 325° C. |
| Deflector (DF): | 30 volt |
| Focussing potential (FP): | 225 volt |
| Entrance potential (EP): | 10 volt |

The light scattering detector is connected to the Sciex API 150. The light scattering detector is a Sedere Sedex 55 operating at 50° C. and 3 bar N$_2$ pressure. The complete system is controlled by a Dell optiplex GX400 computer operating under Windows NT.

AMAP 3 Method

Identical with the AMAP 2 Method, except for the LC method, the latter being:

| step | total time | flow (µl/min) | A(%) | B(%) |
|---|---|---|---|---|
| 0 | 0 | 2300 | 95 | 5 |
| 1 | 1.8 | 2300 | 0 | 100 |
| 2 | 2.5 | 2300 | 0 | 100 |
| 3 | 2.7 | 2300 | 95 | 5 |
| 4 | 3.0 | 2300 | 95 | 5 |

EXAMPLES OF FORMULATION OF COMPOUND AS USED IN ANIMAL STUDIES

For oral (p.o.) administration the desired quantity (up to 20 µmol) of the solid Example 1 was added to 1 ml of tol % (w/v) methyl hydroxyethyl cellulose and 0.1% (w/v) poloxamer in water. The compound was suspended by vortexing for 10 minutes.

For subcutaneous (s.c.) administration the desired quantity (up to 15 µmol) of the solid Example 1 was dissolved or suspended in 1 ml saline solution.

Pharmacological Data

| | affinity | | In vitro agonism | In vivo agonism | | |
|---|---|---|---|---|---|---|
| | | | | transit Mean | diarrhoea mean | hypersensitivity |
| Ex. | ORL1 pK$_i$ | μ-opiate pK$_i$ | cAMP assay pEC$_{50}$ | retention time % control | score % control | max inhibition % of control |
| 1 | 9.3 | 7.7 | 10.2 | | | 49 (s.c.) |
| 12 | 8.8 | 7.1 | 8.1 | 110 (s.c.) | | |
| 13 | 8.9 | 7.4 | 8.7 | 105 (s.c.) | 59 (s.c.) | |
| 14 | 9.2 | 7.2 | 9.9 | 111 (s.c.) | 64 (s.c.) | |
| 15 | 8.5 | 7.5 | | | | |
| 16 | 9.1 | 7.4 | | | | |
| 17 | 8.6 | 7.0 | | | | |
| 21 | 8.1 | 7.4 | | | | |
| 22 | 8.2 | 7.4 | | | | |
| 28 | 9.2 | 8.0 | | 106 (s.c.) 94 (p.o.) | 78 (s.c.) 58 (p.o.) | 35 (s.c.) |
| 29 | 8.2 | 7.4 | | | | |
| 34 | 8.3 | 7.6 | | | | |
| 37 | 8.8 | 7.7 | 10.6 | | | 34 (s.c.) |
| 39 | 9.4 | 7.2 | | | | |
| 42 | 8.2 | 7.4 | | | | |
| 45 | 8.5 | 8.1 | | | | |
| 51 | 9.1 | 7.9 | | 102 (s.c.) 105 (p.o.) | | 45 (s.c.) 44 (p.o.) |
| 58 | 8.1 | 7.4 | | | | |
| 59 | 8.1 | 7.4 | | | | |
| 61 | 9.2 | 7.7 | | | | |
| 68 | 7.9 | 7.6 | | | | |
| 70 | 8.1 | 7.6 | | | | |
| 83 | 8.6 | 7.8 | | | | |
| 91 | 8.1 | 7.4 | | | | |
| 214 | 8.0 | 7.3 | | | | |
| 219 | 8.2 | 6.7 | | | | |
| 223 | 7.9 | 7.1 | | | | |
| 230 | 8.0 | 7.0 | | | | |
| 233 | 7.6 | 6.8 | | | | |
| 238 | 7.9 | 7.0 | | | | |
| 275 | 8.1 | 7.4 | | | | |
| 277 | 8.1 | 7.0 | | | | |
| 279 | 7.7 | 6.8 | | | | |
| 285 | 7.9 | 7.1 | | | | |
| 292 | 8.2 | 7.1 | | | | |
| 293 | 7.9 | 7.0 | | | | |
| 298 | 8.1 | 7.1 | | | | |
| 313 | 7.8 | 6.9 | | | | |
| 315 | 8.0 | 6.8 | | | | |
| 327 | 7.9 | 7.1 | | | | |
| 328 | 7.7 | 6.9 | | | | |
| 346 | 8.0 | 6.9 | | | | |

The invention claimed is:

1. A compound of the general formula

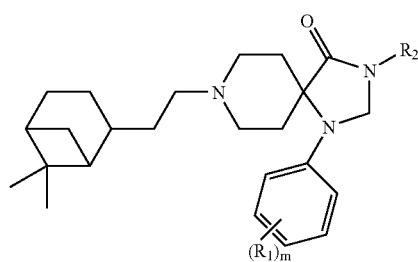

(1)

wherein:

R$_1$ is a hydrogen, a CF$_3$ group, a C$_{1-6}$alkyl group, a C$_{3-6}$cycloalkyl group, a phenyl group, an amino group, a C$_{1-3}$alkylamino group, a C$_{1-3}$dialkylamino group, a hydroxyl group, a C$_{1-3}$hydroxyalkyl, a C$_{1-3}$alkoxy group, an OCF$_3$ group, a carboxyl group, an aminocarbonyl group, or a C$_{1-3}$alkylsulphonyl group;

m is an integer from 1 to 4, with the proviso that when m is 2, 3 or 4, the R$_1$ substituents may be either the same or different;

R$_2$ represents is a hydrogen, an optionally substituted C$_{1-6}$alkyl group, a C$_{3-6}$ cycloalkyl group, a —CH$_2$OH group, a —CH$_2$OCH$_3$ group, a carboxyl group, an acetyl group, an optionally substituted benzyl group, or a group Q, wherein group Q has the following structure (2),

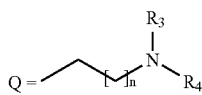 (2)

wherein
   n is an integer from 0 to 7,
   $R_3$ is a hydrogen or a $C_{1-3}$alkyl,
   $R_4$ is a hydrogen, an optionally substituted $C_{1-6}$alkyl, a saturated, unsaturated or partially saturated mono-, di- or tricyclic optionally substituted cycloalkyl ring, and a $C_{1-3}$alkyl group substituted with a saturated, unsaturated or partially saturated optionally substituted five or six-membered cycloalkyl ring which optionally contains one or more heteroatoms; or
   ($R_3$+$R_4$) together with the nitrogen atom to which they are bonded, form a saturated, unsaturated or partially saturated mono-, di- or tricyclic optionally substituted cycloalkyl ring, or
   a stereoisomer, or pharmacologically acceptable salt, thereof.

2. The compound of claim 1; wherein
   $R_1$ is a hydrogen, a $CF_3$ group, a $C_{1-6}$alkyl group, a hydroxyl group, a $C_{1-6}$alkoxy, or an $OCF_3$ group, and wherein m=1.

3. The compound of claim 2 wherein
   $R_2$ is the group Q.

4. The compound of claim 3; wherein
   $R_3$ is a methyl group;
   $R_4$ is a $C_{1-3}$alkyl group substituted with a saturated, optionally substituted six-membered cycloalkyl ring which optionally contains one or more heteroatoms.

5. The compound of claim 4; wherein
   $R_4$ is a methylene group substituted with an optionally substituted piperidine ring.

6. A pharmaceutical composition comprising a pharmacologically effective amount of at least one compound according to claim 1 as an active ingredient.

7. A method of treating a diarrhoea or visceral pain comprising administering to a patient in need thereof an effective amount of at least one compound according to claim 1.

* * * * *

UNITED STATES PATENT AND TRADEMARK OFFICE
CERTIFICATE OF CORRECTION

PATENT NO. : 7,241,770 B2  
APPLICATION NO. : 11/007255  
DATED : July 10, 2007  
INVENTOR(S) : Mentzel et al.

Page 1 of 1

It is certified that error appears in the above-identified patent and that said Letters Patent is hereby corrected as shown below:

Column 71, line 50, after "formula" insert --(1)--.

Column 72, line 61, delete "represents".

Signed and Sealed this

Second Day of October, 2007

JON W. DUDAS  
*Director of the United States Patent and Trademark Office*